United States Patent
Savage

(10) Patent No.: US 7,682,345 B2
(45) Date of Patent: Mar. 23, 2010

(54) MEDICAL INJECTOR SYSTEMS HAVING AN INJECTOR PLUNGER THAT RELEASABLY ENGAGES A SYRINGE HUB UPON RETRACTION OF THE PLUNGER

(75) Inventor: Rodney Brian Savage, West Pennant Hills (AU)

(73) Assignee: MEDRAD, Inc., Indianola, PA (US)

( * ) Notice: Subject to any disclaimer, the term of this patent is extended or adjusted under 35 U.S.C. 154(b) by 948 days.

(21) Appl. No.: 10/380,188

(22) PCT Filed: Jul. 10, 2001

(86) PCT No.: PCT/AU01/00830

§ 371 (c)(1),
(2), (4) Date: Mar. 10, 2003

(87) PCT Pub. No.: WO02/04049

PCT Pub. Date: Jan. 17, 2002

(65) Prior Publication Data

US 2004/0158205 A1   Aug. 12, 2004

(30) Foreign Application Priority Data

Jul. 10, 2000 (AU) .................................. PQ8679
Jul. 24, 2000 (AU) .................................. PQ8908
Jul. 24, 2000 (AU) .................................. PQ8909

(51) Int. Cl.
*A61M 1/00* (2006.01)
*A61M 5/315* (2006.01)
(52) U.S. Cl. ...................... 604/228; 604/151

(58) Field of Classification Search ................... 604/65, 604/67, 151, 153–156, 131, 218, 207–211, 604/228, 229; 128/DIG. 1, DIG. 12
See application file for complete search history.

(56) References Cited

U.S. PATENT DOCUMENTS 2,392,196 A   1/1946 Smith
3,348,545 A   10/1967 Sarnoff et al.

(Continued)

FOREIGN PATENT DOCUMENTS

EP   0567945   11/1993

(Continued)

OTHER PUBLICATIONS

Supplementary Partial European Search Report for EP 01949108 dated Apr. 13, 2007.

(Continued)

*Primary Examiner*—Matthew F Desanto
(74) *Attorney, Agent, or Firm*—Jill Denesvich; Gregory L. Bradley

(57) ABSTRACT

A medical injector system for injecting fluid from a syringe (300) into a patient, the syringe (300) having a barrel (300) and a plunger (310), the plunger (310) comprising an inner surface having an engaging portion (311) adapted to be releasably engaged by a plunger handle (130) which has a retention member (142) adapted to releasably engage the engaging portion (311) of the plunger (310); and a syringe holder comprising a cradle member (200) adapted to receive a barrel (300) of the syringe (300) and a pivotable catch (500) to releasably lock the syringe (300) in the cradle member (200).

19 Claims, 37 Drawing Sheets

U.S. PATENT DOCUMENTS

| | | | |
|---|---|---|---|
| 4,465,473 A * | 8/1984 | Ruegg | 604/154 |
| 4,677,980 A | 7/1987 | Reilly et al. | |
| 5,007,904 A | 4/1991 | Densmore et al. | |
| 5,106,379 A | 4/1992 | Leap | |
| 5,300,031 A | 4/1994 | Neer et al. | |
| 5,383,858 A | 1/1995 | Reilly et al. | |
| 5,429,611 A | 7/1995 | Rait | |
| 5,433,712 A | 7/1995 | Stiles et al. | |
| 5,545,140 A | 8/1996 | Conero | |
| 5,738,655 A * | 4/1998 | Vallelunga et al. | 604/110 |
| 5,779,675 A | 7/1998 | Reilly et al. | |
| 5,807,334 A | 9/1998 | Hodosh et al. | |
| 5,808,203 A * | 9/1998 | Nolan et al. | 73/700 |
| 5,947,929 A | 9/1999 | Trull | |
| 6,080,136 A | 6/2000 | Trull et al. | |
| 6,196,999 B1 * | 3/2001 | Goethel et al. | 604/131 |
| 6,652,489 B2 | 11/2003 | Trocki et al. | |
| 6,958,053 B1 * | 10/2005 | Reilly | 604/154 |
| 2003/0009133 A1 * | 1/2003 | Ramey | 604/155 |
| 2004/0064041 A1 | 4/2004 | Lazzaro et al. | |
| 2004/0116861 A1 | 6/2004 | Trocki et al. | |
| 2005/0113754 A1 | 5/2005 | Cowan | |

FOREIGN PATENT DOCUMENTS

| | | |
|---|---|---|
| EP | 0900573 | 3/1999 |
| GB | 2108852 | 5/1983 |
| WO | WO/97/07841 | 3/1997 |
| WO | WO 9736635 A1 * | 10/1997 |
| WO | WO 01/37903 * | 5/2001 |

OTHER PUBLICATIONS

Supplementary Partial European Search Report for EP 01949108 dated Apr. 25, 2007.

* cited by examiner

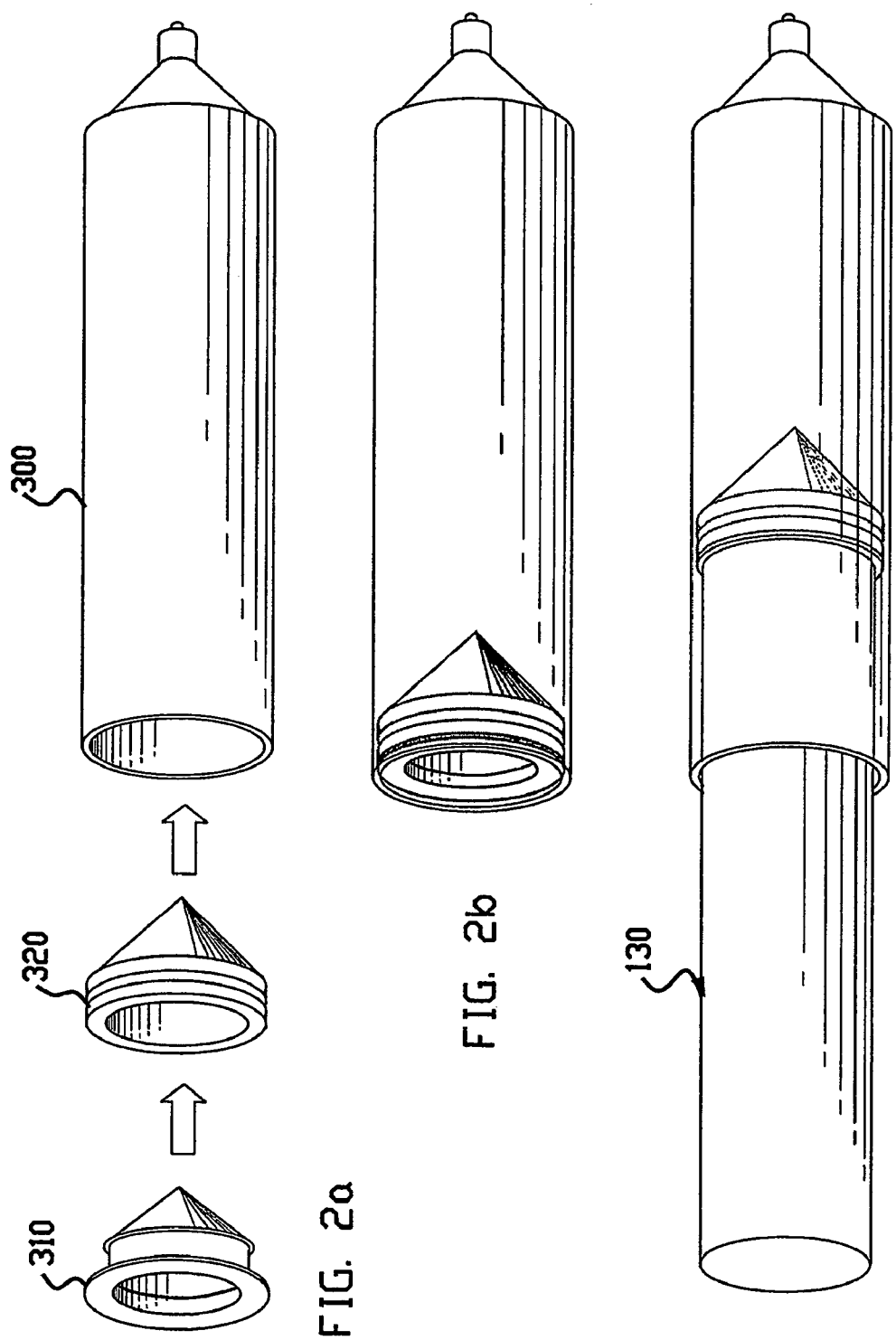

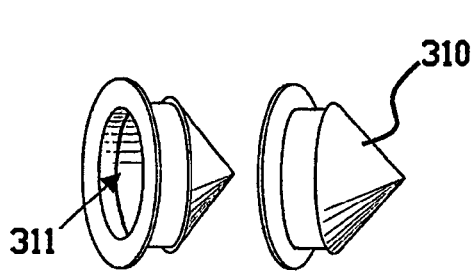
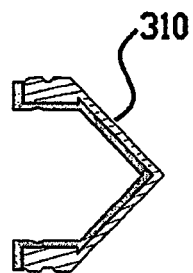
FIG. 3a  FIG. 3b  FIG. 3c
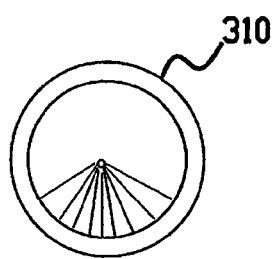
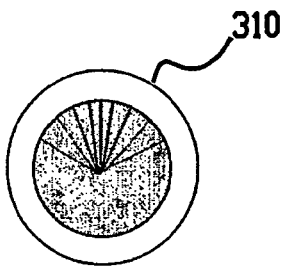
FIG. 3d  FIG. 3e
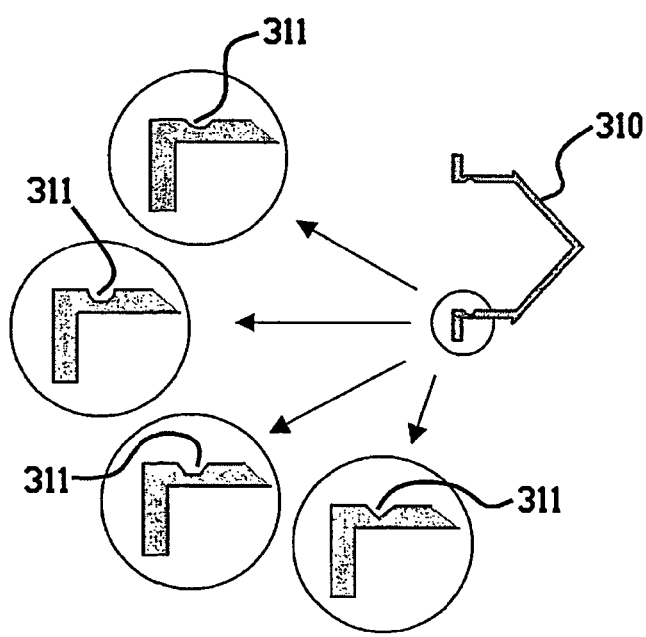
FIG. 4a
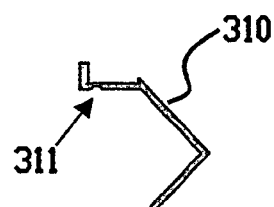
FIG. 4b
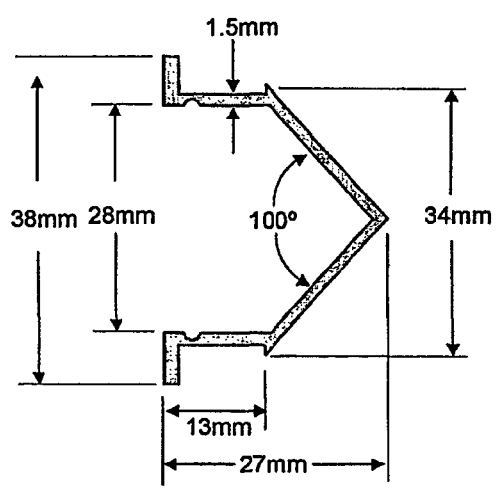
FIG. 5

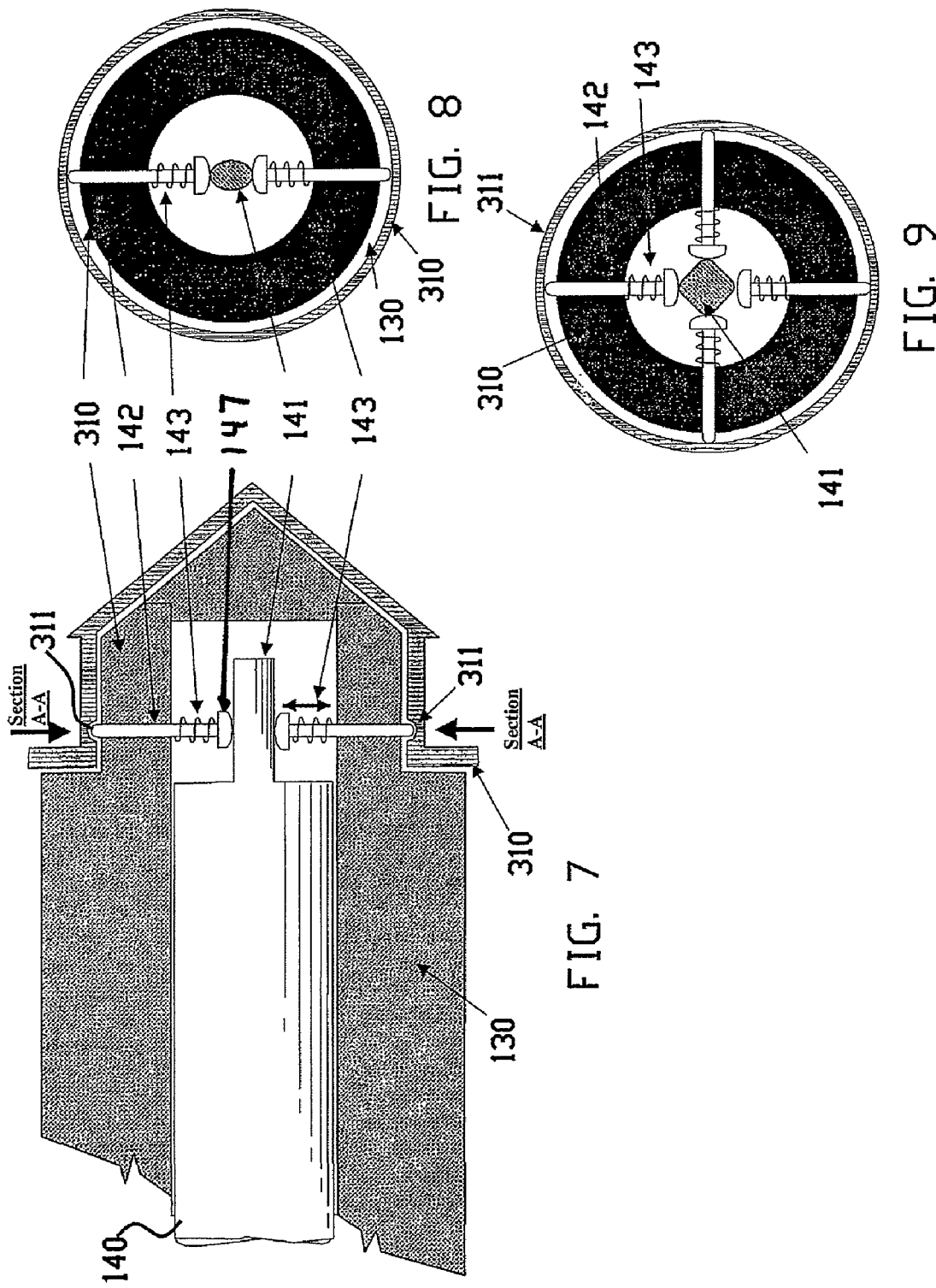

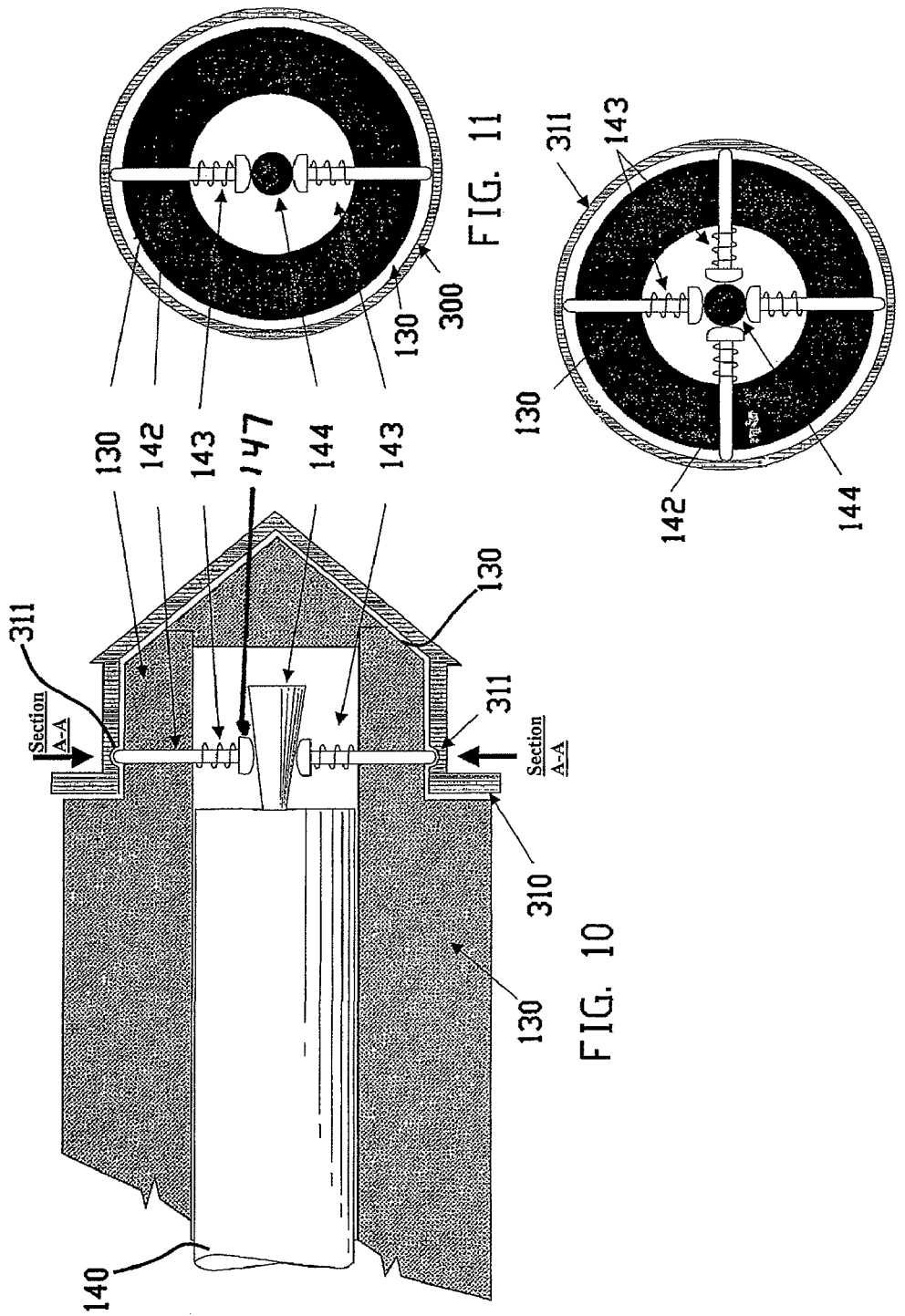

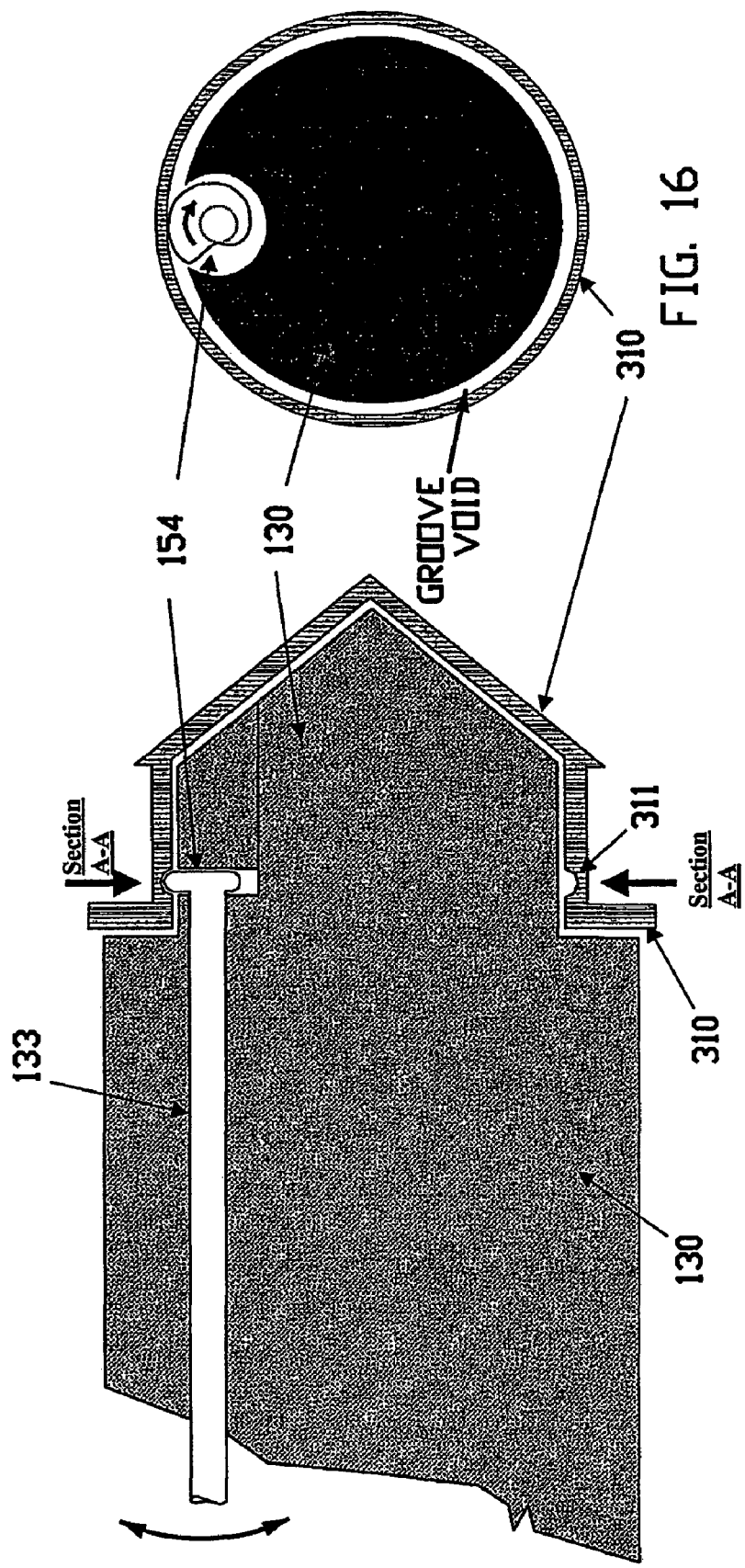

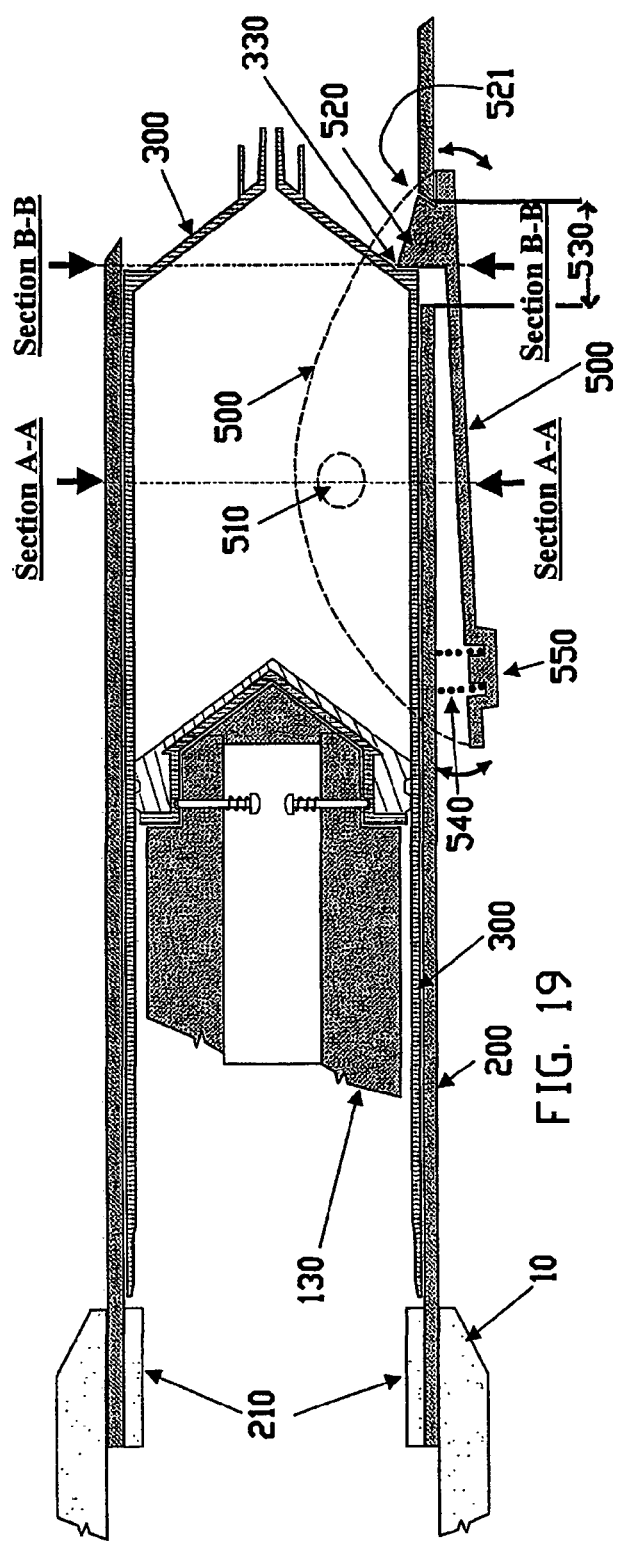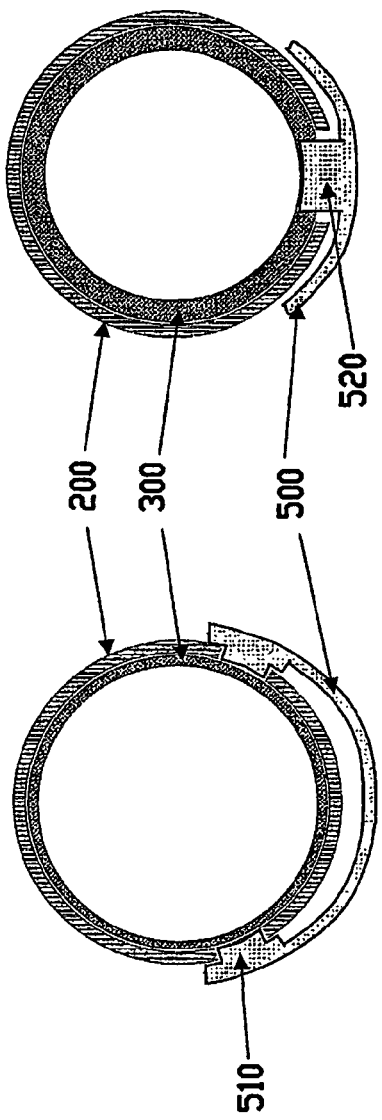

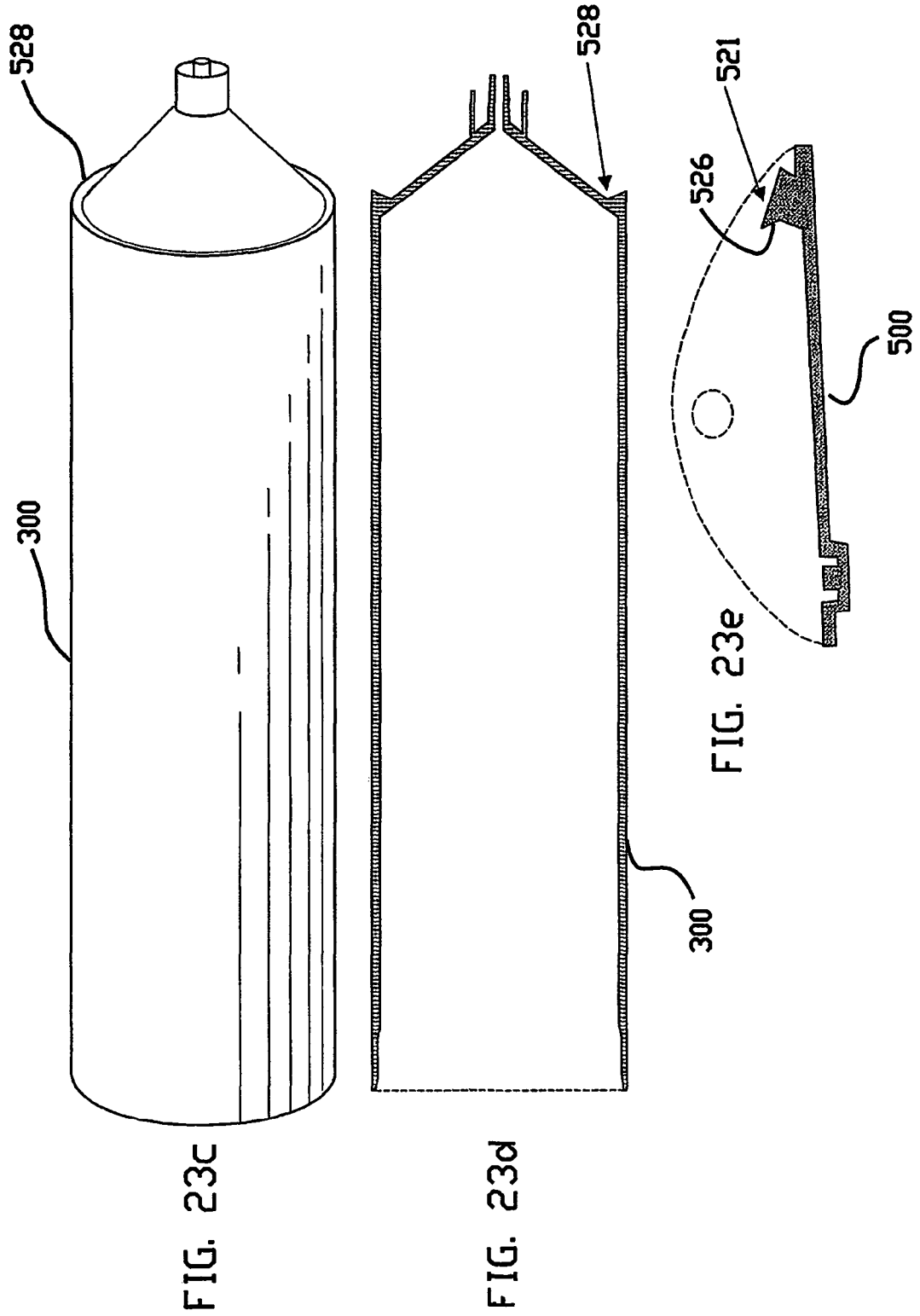

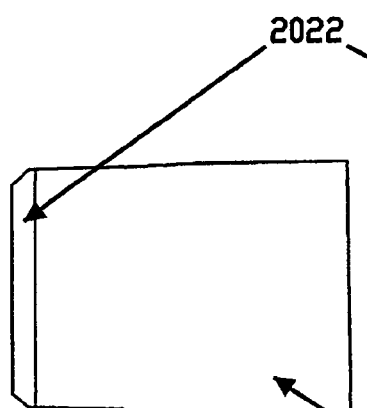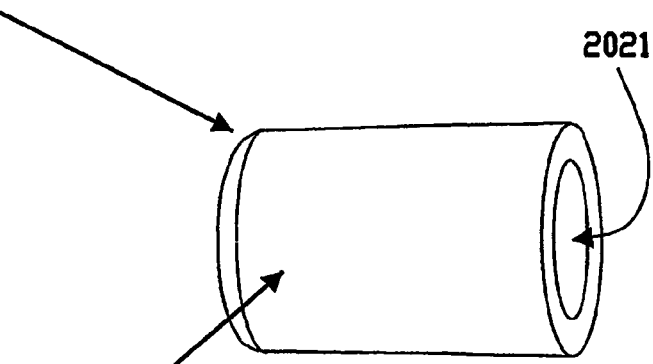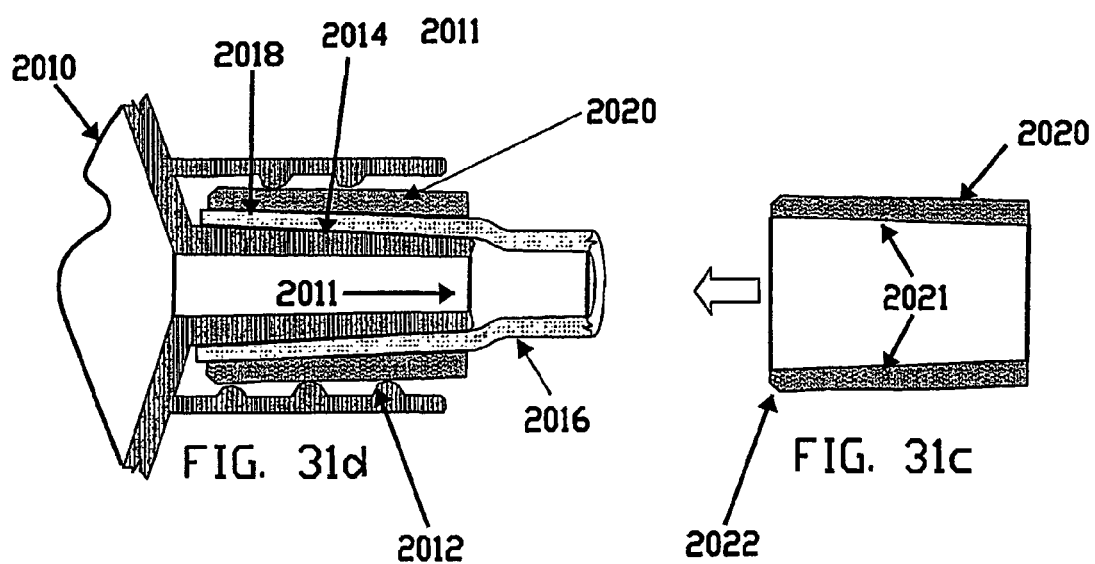

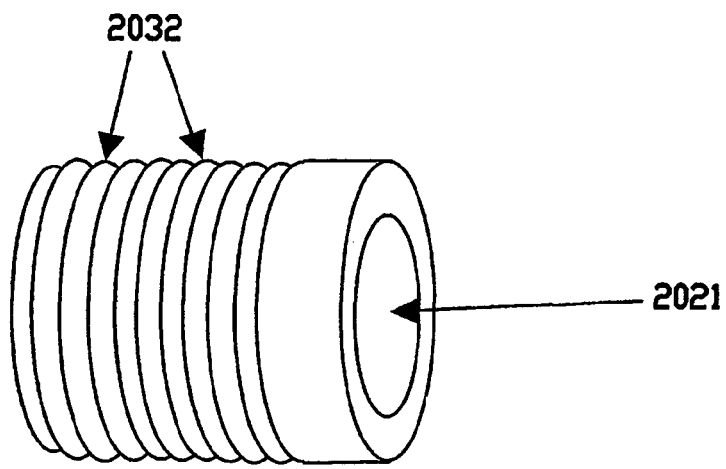
FIG. 32a
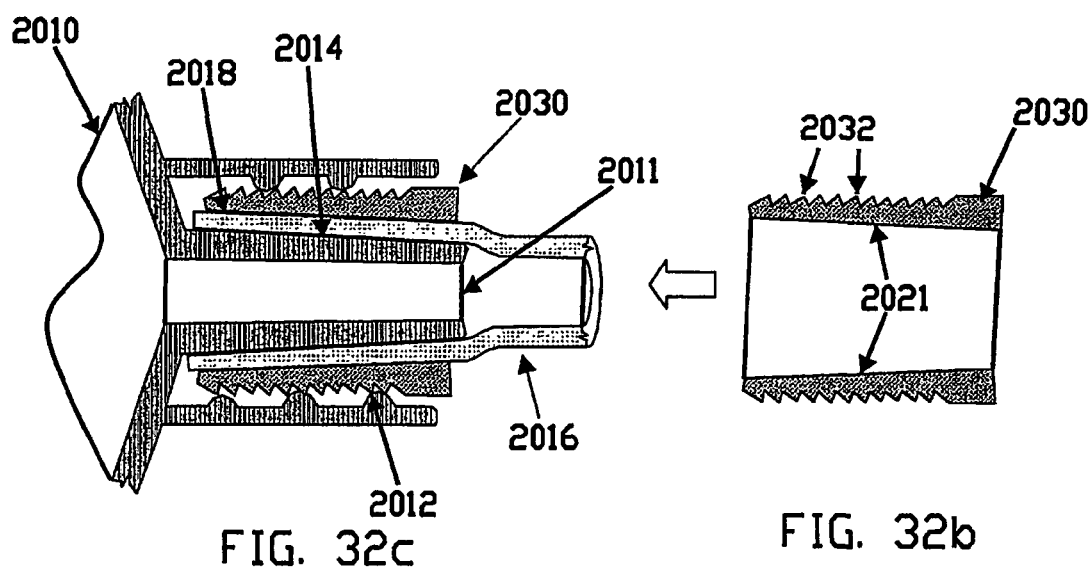
FIG. 32c
FIG. 32b

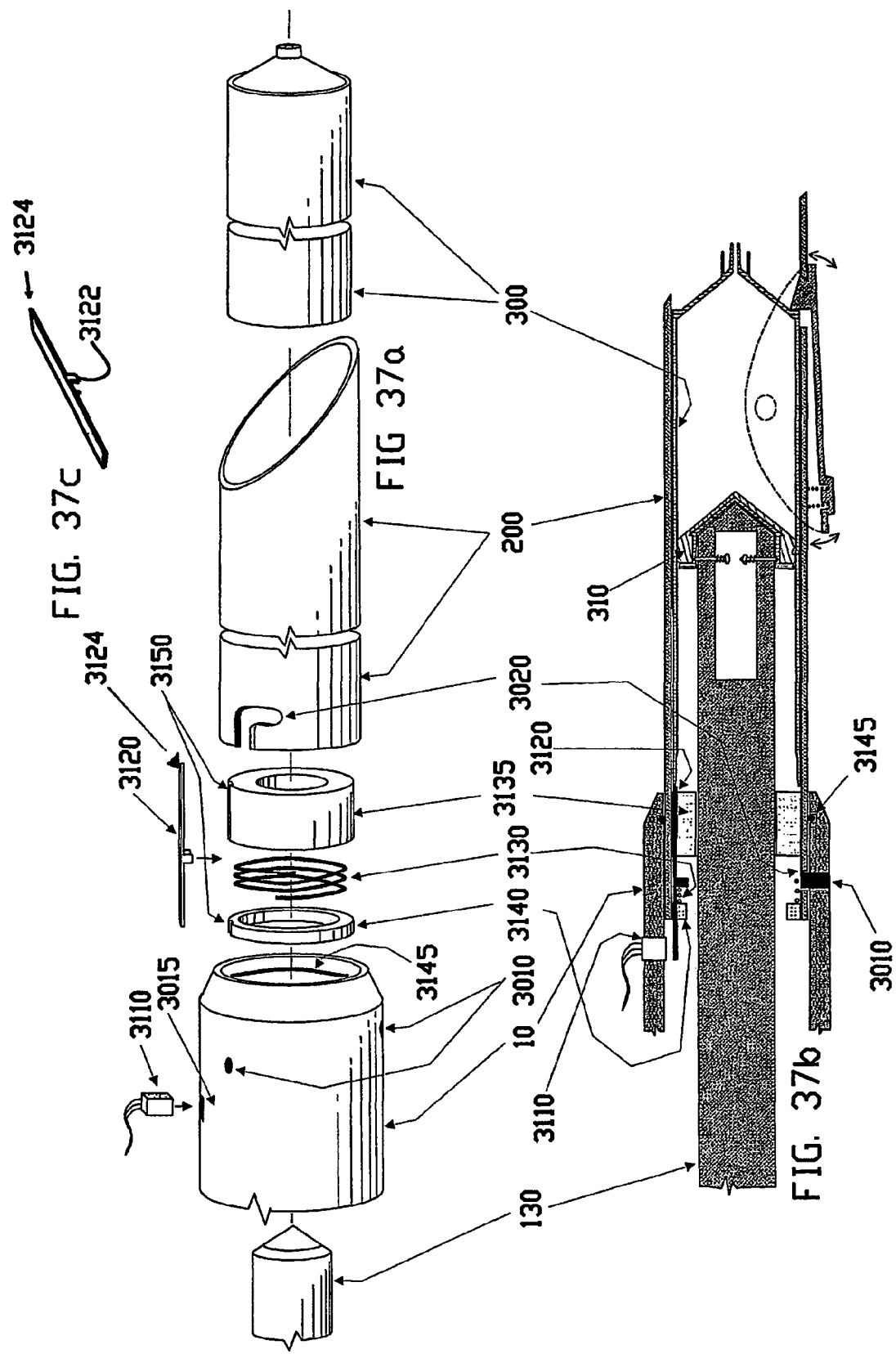

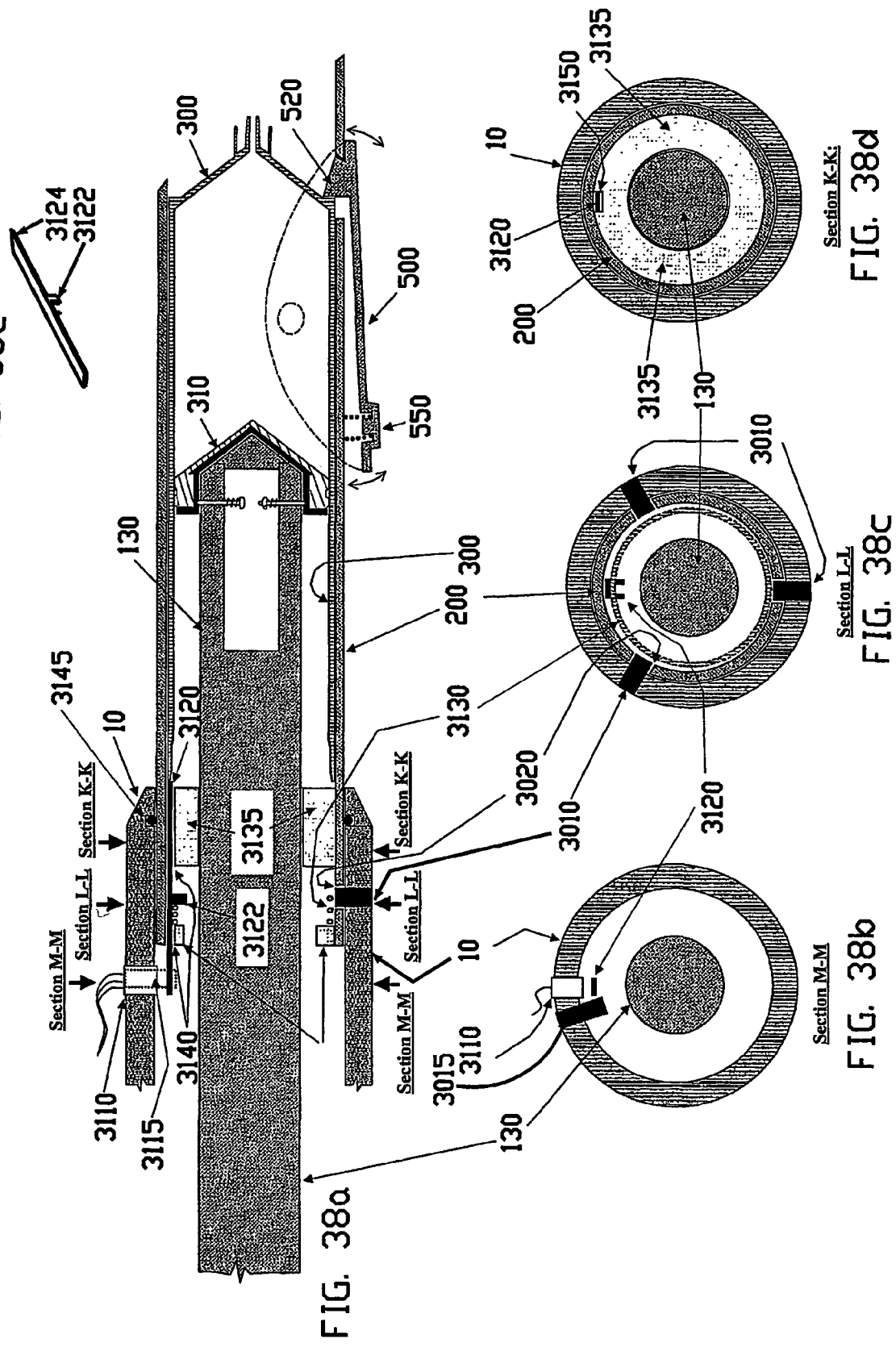

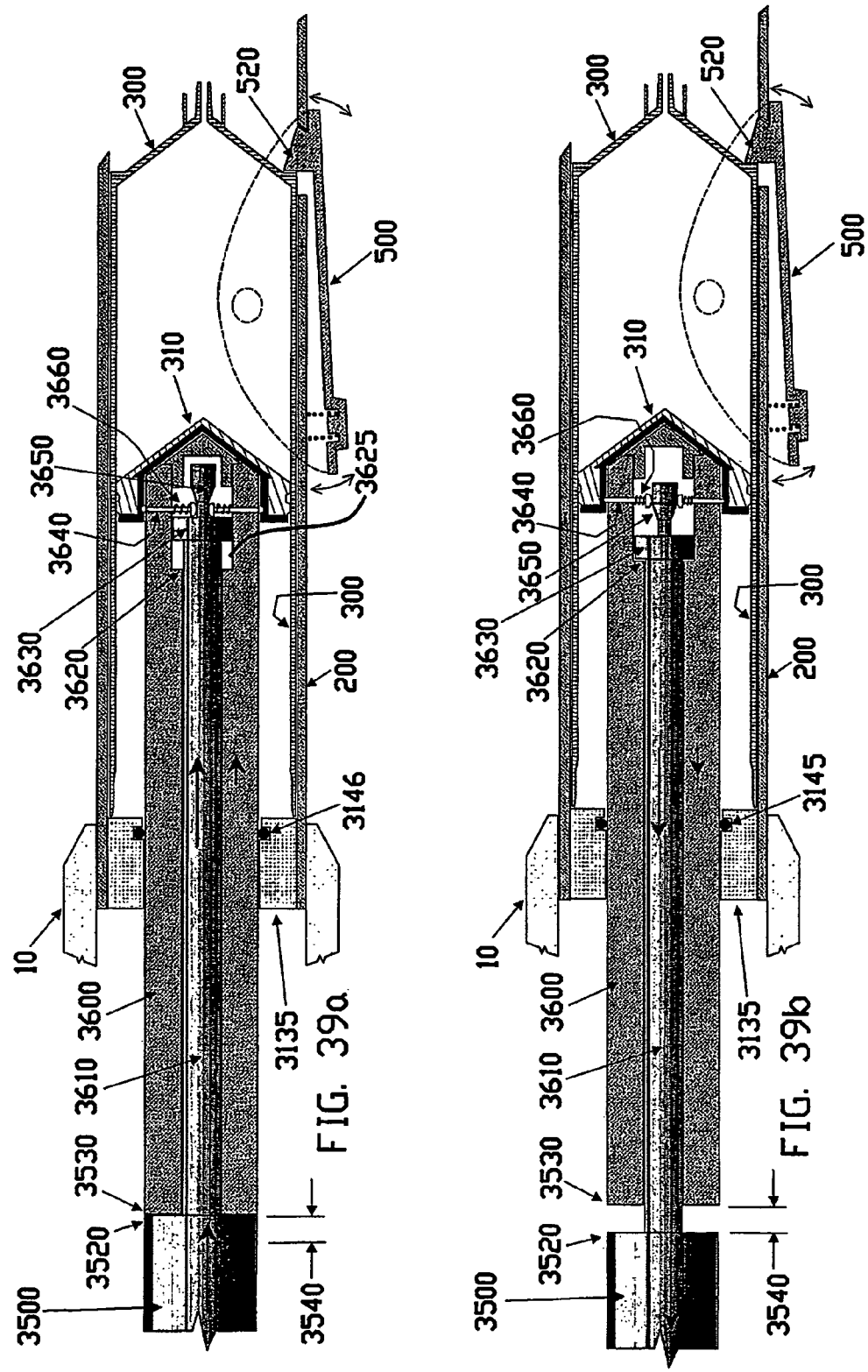

MEDICAL INJECTOR SYSTEMS HAVING AN INJECTOR PLUNGER THAT RELEASABLY ENGAGES A SYRINGE HUB UPON RETRACTION OF THE PLUNGER

FIELD OF THE INVENTION

The present invention relates to medical injector systems for injecting medical fluids into a patient's vascular system.

BACKGROUND OF THE INVENTION

Medical injectors and syringes for injecting contrast media into a patient for imaging biological structures are known in the art. For example, U.S. Pat. No. 4,677,980, issued to D. M. Reilly et al. on Jul. 7, 1987, and entitled "Angiographic Injector and Angiographic Syringe for Use Therewith," which is assigned to the same Assignee as the subject application, discloses an angiographic injector apparatus. The apparatus is designed for injecting contrast media into the vascular system of an animal, in which syringes are rear-loaded into a pressure jacket of the injector. More specifically, the apparatus comprises a rotatable turret which carries a pair of the pressure jackets and which is rotatable so that when one of the pressure jackets, into which a syringe has been rear-loaded, is in an injection position, the other pressure jacket is in a position in which an associated syringe can be rear-loaded. Subsequently, when injection of contrast media from the first syringe is completed, the turret is rotated to move the first syringe to an unloading-loading position, with the second pressure jacket and the syringe concurrently being moved into the injection position.

In the apparatus disclosed in the '980 patent, a drive member of the angiographic injector can be drivingly connected to, or disconnected from, a plunger of a syringe at any point along the path of travel of the syringe plunger by a releasable mechanism. However, for the releasable mechanism to correctly operate, the syringe plunger must be properly oriented to mate with the injector piston. Further, during loading of the syringe on the injector, the syringe must be correctly aligned within a respective pressure jacket to allow the syringe plunger and the injector piston to connect to and disconnect from each other.

An improved apparatus over the '980 patent apparatus is disclosed in U.S. Pat. No. 5,383,858, issued to D. M. Reilly et al. on Jan. 24, 1995, and entitled "Front-Loading Medical Injector and Syringe for Use Therewith," which is also assigned to the same Assignee as the present application. In the apparatus described in the '858 patent, the syringe is front-loaded onto, in at least one embodiment, a pressure jacket-less injector, overcoming one of the drawbacks of the '980 patent injector apparatus.

The injector described in the '858 patent has a first release mechanism for attaching and releasing the syringe from the injector. In addition, the apparatus includes a second release mechanism that engages and disengages the injector piston from the syringe plunger. Upon rotation of the syringe, the syringe is attached to or released from the injector and, simultaneously, the plunger is attached to or released from the piston. The structure disclosed requires that the syringe be installed on the injector in a specific orientation so that the syringe can releasably engage the injector and, simultaneously, the plunger can releasably engage the piston. In addition, as with the syringe disclosed in the '980 patent, during assembly the syringe plunger must be correctly oriented within the syringe.

Another injector apparatus is disclosed in U.S. Pat. No. 5,300,031, issued to C. Neer et al. on Apr. 5, 1994, and entitled "Apparatus for Injecting Fluid into Animals and Disposable Front Loadable Syringe Therefor." The '031 patent discloses various embodiments of a pressure-jacketed injector wherein a syringe is loaded into and removed from an injector pressure jacket through an opening provided in the front end of the pressure jacket. To retain the syringe within the pressure jacket, for example, during an injection operation, the front end of the syringe is locked to the front end of the pressure jacket. To correctly connect the syringe to the pressure jacket, the syringe may only be inserted into the pressure jacket in one orientation.

In each example discussed above, the syringe must be connected to the injector in a specific orientation to assure proper syringe mounting. Proper alignment is required to assure that the syringe may be operated properly during a medical imaging procedure. The required orientation, however, hinders rapid attachment and replacement of the syringe. The required orientation may also increase the manufacturing assembly cost and complexity of the syringe.

Accordingly, while the above injector and syringe apparatuses have proven effective, a need has arisen for a simpler front-loading medical injector. More specifically, to facilitate further the loading operation, a need has arisen for a syringe that can be easily connected to the injector without regard for the specific orientation of the syringe and/or syringe plunger. In addition, to simplify assembly of the syringe components, a need has arisen for a syringe with a plunger that does not need to be oriented in a specific relation to the barrel or base of the syringe. Furthermore, to minimize the time required to prepare an injector for an injection procedure, a need has arisen for injectors providing automated features. There is a further need to add automated features which contribute to the safety of the patient, for example, by decreasing the chances of cross-contamination.

Medical fluids are normally packaged in containers or bottles, which have an elastomer bung (or cork) in the top. The bung can be pierced with a conventional needle or a plastic spike to draw fluid from the bottle into the syringe. However it is common practice to simply remove the bung, and draw up fluid into the syringe using a plastic cannula. This practice exposes the fluid to ambient microbes, and allows contamination, and thus increases the risk of undesirable infection of the patient. Certain vented spikes with special microbe filters have been developed to address this problem. However in use, the filling procedure is very tedious, and some fluid is often lost through the filter. Where large volumes are drawn into the syringe according to known methods, it can be very difficult to simultaneously hold the bottle inverted, and draw back the syringe.

Another important requirement when using syringe pumps to inject patients is to ensure that all air is purged from the system, including the tube, before it is connected to the patient. If this is not done, then it is possible that a bubble of air may be injected into the patient which can cause serious illness.

It has also been found that existing injector apparatus and injectors do not have features which discourage inadvertent re-use of syringes and associated tubes and spikes, which can result in the serious hazard of cross infections from one patient to the next.

Luer connectors are found on the outlet of most syringes used in medicine, and are well defined in International Standard IS0594. A locking thread is sometimes found associated with luer connectors, termed "luer locking", and are particularly used for higher pressure applications, where the thread assists closure and retention of the connections.

Flexible plastic tubing is used in many medical applications for conveying drugs, fluid, contrast etc between syringes and patients. The tubes are normally manufactured from flexible plastic, with luer connectors bonded to each end to facilitate secure and releasable male and female connections. Connectors are normally moulded from rigid plastic, having a luer outlet, with an cylindrical inlet sized to accept a close interference fit with the relatively soft tube. The tubing is forced over (or inside) the cylindrical inlet end, and is traditionally bonded using solvent or cement adhesive. For higher pressure applications the bond must be very certain and secure to avoid bursting.

On occasions, the tubing may be attached permanently to the syringe, for example to reduce manufacturing costs, reduce the chances of spilling contaminated fluids, or to protect the tip of the syringe from contamination. However bonding directly to syringes is rarely successful or certain because syringes are usually moulded from polypropylene. Some tubing materials are also difficult to bond. Moreover, bonding normally requires the use of powerful solvent cements such as cyclohexanone, or cyanoacrylates, both of which release harmful vapours, and can leave unwanted residues.

In this specification, unless the contrary is expressly stated, where a document, act or item of knowledge is referred to or discussed, this reference or discussion is not an admission that the document, act or item of knowledge or any combination thereof was at the priority date:
(a) publicly available;
(b) known to the public;
(c) part of common general knowledge; or
(d) known to be relevant to an attempt to solve any problem with which this specification is concerned.

SUMMARY OF THE INVENTION

According to a first aspect of the invention, there is provided a syringe holder for a medical injector system comprising a cradle member adapted to receive a barrel of the syringe; and a pivotable catch to releasably lock the syringe in the cradle member wherein the catch is biased towards a first position and engages the syringe at the first position and disengages the syringe at a second position.

By providing a pivotable catch to releasably lock the syringe, it is possible to enable front-loading of syringes into the syringe holder by removing the requirement of a front wall on the cradle. A person skilled in the art will appreciate that the catch surface can be varied in length to engage a larger (or smaller) amount of the syringe surface.

According to a particularly preferred embodiment, the syringe holder further comprises a positioning device located on the cradle member to locate one end of the syringe in a predetermined location in the cradle member.

According to one preferred embodiment, the cradle member is a sleeve and surrounds the barrel of the syringe. Preferably such a sleeve is adapted to support the syringe against expansion under pressure to provide support against internal pressure during expulsion of fluid. This allows the wall thickness of the barrel to be reduced, thereby saving manufacturing costs.

According to another preferred embodiment, the catch mechanism engages a front shoulder of the syringe. Preferably the catch engages the syringe through a hole defined in the cradle or sleeve.

According to another preferred embodiment, upon insertion of the syringe barrel into the cradle or sleeve, a front portion of the catch engages a corresponding front portion of the syringe, to thereby retain the syringe within the cradle or sleeve. To remove the syringe from the cradle or sleeve, a rear portion of the catch is depressed, causing the front portion to disengage from the syringe barrel.

The syringe may be loaded through the front end of the pressure sleeve by simply sliding until the catch locks automatically. This manner of loading from the front is simple, requiring no twisting or conscious locking action by the operator. The syringe may also be simply released by pressing the syringe release button, and withdrawing the syringe forward. The catch may be part of the cradle member to enable assembly and replacement to/from the sleeve, for cleaning or renewal.

The syringe holder is preferably fabricated from transparent hard plastic, and comprises a plain cylinder having an open end, cut off at an angle of approximately 50 degrees to enable easy insertion of the syringe. Construction from transparent material provides unobstructed vision of the syringe and its contents, particularly of the forward end where all air must be purged following filling. Typically the sleeve is of one piece construction (optionally including a spring), and low cost to manufacture by fabricating from plain stock tubing, or moulding process.

The rear end of the sleeve is preferably fixed (preferably releasably for cleaning) to the injector, aligned co-axially with the injector plunger—this enables the syringe to be removed from the injector at any time without fear of the plunger touching the inside of the syringe (and thereby possibly contaminating it). Volume graduations may be printed onto the sleeve of the holder, and are thereby not required on the syringe.

The syringe is loaded rear first into the front of the holder, which forms a close fitting sleeve supporting the syringe against expansion under the high pressures endured with injectors. The holder preferably has a square notch towards the front which allows access for, and supports the syringe catch whilst under load. Two round holes in the sleeve are preferable to act as hinge sockets for the catch.

Preferably the catch is moulded as a partial cylinder shape from a hard flexible plastic, and has 2 opposing hinge posts which snap into corresponding holes in the sleeve. For replacement or cleaning purposes the catch assembly can be removed by simply spreading the sides apart until the hinge posts clear their respective holes.

According to another preferred embodiment, the cradle member has a biasing member to partially eject the syringe from the cradle member upon release of the catch. Preferably the biasing member upon insertion of the syringe barrel is actuated, thereby biasing the barrel towards a partially ejected position so that the barrel is partially ejected from the sleeve upon release of the catch. Preferably the self-ejecting mechanism (created by the biasing member) comprises a spring and is preferably located at the rear of the sleeve, which upon insertion of the syringe barrel is compressed.

According to another preferred embodiment, the biasing member is adapted to engage and minimize rotation of the syringe.

According to another preferred embodiment, the biasing member is adapted to operate or engage an optical sensor or switch, which advises the injector control unit of the presence of a syringe.

According to one embodiment, the cradle member may be permanently attached to the injector, rather than removed each time the syringe is replaced, thereby improving convenience, and reducing the chance of dropping and soiling the sleeve.

An extension tube can be permanently attached to the syringe. Being front loaded, the associated connecting tube need not be disconnected from the syringe following injection, reducing the risk of spilling contaminated blood.

The catch may be of any suitable shape. According to a particularly preferred embodiment, the front shoulder of the syringe is of a complimentary shape to an engaging portion of the catch. The catch surface may be longer (such as about half of the syringe circumference or substantially co-extensive with the cradle) to more easily retain the syringe on the injector.

The engaging portion of the catch may be of any suitable shape. According to certain preferred embodiments, it is wedge shaped, concave or convex. Optimally the catch mechanism is wedged against the forward edge of an associated notch in the syringe sleeve, transferring most of the load onto the notch (and thus the sleeve and injector), and not on the catch hinges.

As the syringe is loaded into the sleeve the syringe catch is pushed aside. Once the syringe is fully home the front of the syringe clears the catch, and the catch latches due to tension from the spring under the button, forming a fixed stop in front of the front rim of the syringe. If the catch is a dovetail shape, then it is unlikely to partially close, and even if it were to, any tension from the syringe would draw the dovetail catch closed.

During injection the forward force of the syringe is borne by the catch. Such a catch forms a dovetail between the syringe and the notch in the sleeve, so that the catch cannot be released, nor slip whilst under load.

According to another preferred embodiment the holder or the injector system comprises an illumination member to illuminate the syringe holder. The illumination member may be mounted, engaged or attached to any suitable component of the holder or injector system. Preferably it is mounted to the holder. According to another preferred embodiment, it is mounted to the injector and preferably in the nose of the injector. The illumination member may be of any suitable type or light source. It may be a lamp, or globe, it may be a Light. Emitting Diode (LED). Preferably the illumination member is placed at the exposed rear end of the holder cradle member or sleeve so that some of the light is received and transmitted along the walls of the cradle member or sleeve. As with any thin, dense, transparent material, most of the received light is internally reflected longitudinally, as well as laterally, producing a diffused glow at the front end of the cradle member or sleeve. Preferably the cradle member or sleeve has a bevelled front end of the sleeve which is preferably frosted (for example, it may be sanded) to achieve maximum diffusion, and is therefore visible form a wide angle. Any suitable light source may be used, but they are preferably focused or reflected so that most of their output is projected towards the sleeve. The provision of an illumination member has a variety of useful benefits. In particular it will assist visualisation of the holder and other components in radiography rooms which are dimly lit for certain procedures.

According to another preferred embodiment, the syringe holder comprises an engagement portion to enable simple releaseable engagement with a medical injector. Preferably the engagement portion comprises a locking member and preferably the locking member comprises a slot or a pin.

Such a removable syringe holder provides benefits including:
(a) Allows the syringe holder to be easily removed by the operator for cleaning;
(b) Allows easy replacement if worn or damaged;
(c) Enables the injector to accept a different size or type of syringe; and
(d) Removal for shipment reduces the overall packaging size.

To engage a syringe holder according to the present embodiment with the injector (or injector nose), the sleeve is first inserted into the nose and with gentle inwards pressure, rotated until the bayonet grooves engage the bayonet posts. At this point the holder fully enters the nose, and the holder is rotated clockwise to lock. The bayonet groove and post sets may be spaced evenly around the circumference, or they could also be oriented at matching odd angles so that the holder can only engage in a particular orientation. Preferably there is also provided a Fluid Seal & Friction Device. It may be a simple O-ring or wiper ring, and has two important roles:
(a) prevent fluids from entering the injector;
(b) provide a friction means to decrease the possibility of inadvertent removal of the syringe holder.

According to a particularly preferred embodiment, the syringe holder comprises a blocking member to regulate disengagement of the holder with the medical injector. Preferably the blocking member stops disengagement of the holder with the medical injector if a syringe is present in the holder. According to a particularly preferred embodiment, the blocking member stops disengagement of the holder with the medical injector if the plunger is not in a particular position. According to another particularly preferred embodiment, the blocking member stops disengagement of the holder with the medical injector if the plunger is not in a sufficiently retracted state.

A blocking member according to the present invention if in the form of a lock post is preferably positioned adjacent to the syringe sensor and therefore the syringe holder cannot be removed whilst a syringe is installed, nor during an injection. Additionally, a syringe cannot be installed unless the holder is locked fully (for example by clockwise rotation). This embodiment is particularly useful in the absence of a sensor to verify syringe presence. It will be appreciated that the holder according to this embodiment could not be attached if a syringe were already installed.

Preferably a lock post according to this embodiment is of similar width to, and mounted on the same axis as the syringe flag form of the sensing system according to this invention (discussed below). As the holder is attached, the flag almost touches it when the bayonet slots are fully engaged with the bayonet posts (without rotating). According to this embodiment, in the mounted position, with a syringe installed and the flag pushed back, the holder cannot be rotated the wrong way (in the present case anti-clockwise).

According to a further aspect of the invention, there is provided a hub for a syringe for use with a medical injector system, comprising an outer surface adapted to slidingly engage with a barrel of the syringe, and an inner surface having a substantially annular engaging portion adapted to be releasably engaged by a plunger to permit the hub to be selectively withdrawn along the barrel by the plunger.

By providing a hub with these features, a number of benefits can be obtained which relate to the efficiency of use and safety of the patient to be injected as set out below. Since the plunger remains on the injector, then a syringe having a hub according to the present invention can be fitted over it and thus enable front loading which is much quicker. In addition, front loading avoids the requirement of detaching any extension tubing from the front (nearest the patient) of the syringe and thus decreases the chance of spilling blood which may be contaminated.

The engaging portion may be of any convenient conformation for example, it may be a cavity, a groove or a ridge. Where the engaging portion is a groove, the groove may define a semi-circular cross-section or the groove may extend at least partially along the circumference of the inner surface of the hub. Preferably there are no protrusions from the rear of the hub to impede its movement along the barrel of a syringe.

A hub of this type has many advantages. The thin and uniform wall thickness is ideally suited to injection moulding and provides economies of manufacture in light of the reduced material volume required, the reduced moulding cycle time and the requirement for only simple tooling.

According to one preferred embodiment, the inner surface of the hub is complementary in shape to an outer surface of the plunger. Preferably the inner surface of the hub comprises an interior hollow that contacts the plunger. Such an arrangement allows for a form fit which has the advantage of providing a reinforcing effect to the hub. This allows the wall thickness of the hub to be reduced as compared with hubs of the prior art, thus contributing to the abovementioned economies of manufacture. Preferably the plunger has a tapered front end, which is inherently "self centering" as it engages the hub. This also provides uniform, coaxial support of any seal associated with the hub and improved sealing as compared with hubs of the prior art—particularly at the high pressures used in certain medical injectors. At high pressures the hub can be forcibly expanded to improve its seal against the syringe barrel.

The preferred resilient nature of the hub advantageously provides for positive-fit or force-locking of the retention members at the engagement portion and enables considerable force to be applied when the contents of the syringe are expelled at high pressures.

The hub may also be adapted to engage a seal associated with at least a portion of an outer surface of the hub, or alternatively, the hub may perform the function of a seal. The hub or seal may be used in combination with an o-ring. Preferably the seal, whether it is separate from the hub or not, has an extended leading edge to increase the efficiency of the seal under pressure.

According to a further aspect of the invention there is provided a plunger for a syringe for use with a medical injector system, the syringe having a barrel and a hub slidingly engaging the barrel, the plunger comprising a retention member adapted to releasably engage a substantially annular engaging portion on an inner surface of the hub to permit the hub to be selectively withdrawn along the barrel by the plunger.

As discussed above, by providing a plunger disposed within the housing and comprising a retention member to releasably engage the engaging portion of the hub, it is possible to utilize a single plunger associated with the injector system with multiple syringes, each with a hub according to the present invention. The retention member enables the plunger to engage and lock onto the hub and thereby drive it either backwards or forwards along the syringe barrel to draw fluid into or out of the syringe. Preferably there is more than one retention member.

A retention member according to the present invention may be of any suitable type. Preferably the retention member is mechanically and/or electrically releasably engaged with the hub. According to this embodiment, it is possible to cause the plunger to engage the hub by actuation (as opposed to automatic engagement by pushing or forcing the plunger into the hub). This creates greater control over locking and release of the hub by the plunger, which is important for applications where the plunger movement is controlled electronically. For example, it is particularly advantageous to be able to release the hub at the most front (outlet) portion of the syringe after expulsion of fluid since this will minimize the possibility of re-use of the syringe. According to another preferred embodiment, the releasable engagement is at least partly actuated by a weight mechanism.

According to one preferred embodiment, the releasable engagement is actuated by retraction of the plunger. According to another embodiment, the plunger may be adapted with a weight mechanism such that the retention members are activated (for example, they may protrude from the plunger) when the plunger is in a particular orientation.

According to another preferred embodiment, the releasable engagement occurs automatically on retraction of the plunger and automatically releases the hub during and following forward movement of the plunger, leaving the syringe unlocked following an injection, free to be removed safely. Such an embodiment operates as follows:

The nose portion of the actuation member (the Cone) is attached to the actuation member, which in turn is fixed to the plunger drive. The plunger is driven backward to draw up (fill) a syringe, then forward to expel the syringe. It should be noted that the plunger is slidingly engaged with the actuation member, but with a limited free play. Note also that free sliding of the plunger may also be somewhat reduced by a Friction Seal. According to this embodiment, whenever the plunger drive and actuation member reverse direction, the plunger does not move until the actuation member has traveled some millimeters, and the hub lock mechanism changes state.

The actuation member slides inside the momentarily stationary plunger. The drive and actuation members move forward relative to the plunger and lock pins, allowing them to retract and unlock the syringe. The plunger does not move (due to friction of the Seal) until the shoulder of the plunger drive strikes the rear of the plunger, at which point the hub begins advancing, expelling the syringe. The purpose of unlocking the hub is to allow removal of the used syringe following an injection.

When the plunger begins to retract again the plunger (and hub) is momentarily stationary—the Cone retracts relative to the Lock Pins, extending them to lock the hub onto the Plunger. A shoulder on the actuation member then strikes the Inner Shoulder of the Plunger, retracting it and the hub back for filing etc.

Hence this system automatically ensures that the hub is either locked or unlocked at the appropriate time, avoiding inconvenience and enhancing safety of the injector—for the operator and the patient. Of course, a controller associated with the injector may be programmed to allow for the inherent "free play" whenever the plunger reverses direction.

Benefits of this embodiment include:
(a) Whenever the plunger is advanced the lock pins automatically immediately retract, allowing the plunger to freely enter the hub, regardless of whether the hub had already engaged the plunger. With a gravity operated lock system the piston has to engage the plunger before the head is tilted up (and locked).
(b) With a gravity operated system the head has to be tilted downward to unlock, and the syringe can then be removed.
(c) The syringe hub can be retracted at any time, including to test the patency of a needle. Previously pre-filled syringes can easily be "topped up" at any time. Previously pre-filled syringes can now be purged with the head oriented upwards (This was not possible with the gravity lock system because the lock pins automatically extend when oriented vertically, but the plunger will not yet have engaged the hub).

(d) The hub is always left unlocked following an injection, allowing safe removal of the syringe at this logical point in the injector sequence.
(e) The hub is automatically and immediately locked whenever the plunger is retracted, ensuring the hub will be pulled back.
(f) New syringes may have the plunger assembled and left in any position along the barrel (for the previously described Gravity Lock system the hub must be located at the very rear of the barrel).
(g) This concept is robust and reliable.

According to another preferred embodiment, the retention mechanism is biased to lock only when the syringe is oriented vertically (as necessary when filling & purging), and is automatically unlocked in the injection position. This is desirable to prevent drawing up blood into the syringe, or its re-use. Given certain controls over plunger movement this mechanism can form part of an injection system which can minimise or prevent re-use of a syringe, thereby helping prevent cross infection from one patient to the next. For example, given the following scenario:

New syringes are usually supplied with the retention members and hub in the fully retracted position. Syringes are loaded through the front end of a fixed retaining sleeve (which is part of the holder) of the injector, which aligns the syringe and hub with the plunger of the injector. The injector can only inject following filling, and with the syringe oriented such that its front (outlet) portion is at the same level or below its back (furthest from the patient) portion, that is, the syringe is in a horizontal or down orientation to avoid injecting any residual small amounts of air. With this system the plunger is automatically retracted immediately after completion of an injection, thereby leaving the used hub in the expelled position. The plunger can only be retracted on demand if the syringe is oriented vertically. For the injector plunger to lock into the hub, the plunger must be fully engaged with the hub before the retaining members are extended (this system extends the retaining members as the plunger is tilted from the horizontal to the vertical). As a new syringe is loaded, the hub will, by default, engages the plunger of the injector and as the injector is subsequently tilted up a weight mechanism, such as a weighted rod slides backward due to gravity, and thereby actuates the retention member to secure the hub onto the plunger. The injector can now retract the plunger, and fill the syringe by drawing fluid down into it.

If a used (even partially expelled) syringe were loaded into the injector, its hub would, by default, be positioned forward of the retracted plunger and cannot engage with it. When the injector is tilted up (thus tilting the front of the syringe up), the retention members extend, but do not secure the hub. Hence the hub cannot be drawn back and the syringe can not be re-filled.

As syringes for use with and according to the present invention do not have their own plunger, there is no protrusion from the rear of the syringes. Therefore there is little danger of dislodging the hub in transit and during handling. (As described above, the syringe is best assembled with the hub as far back as possible).

According to another preferred embodiment, the retention member is biased away from engagement with the hub.

In another preferred embodiment, the retention member comprises an actuation member disposed at least partially within a bore defined in the plunger and a locking member is located at or adjacent one end of the retention member and/or plunger, the locking member being movable by the retention member into or out of engagement with the engaging portion of the hub.

The retention member may comprise any suitable member, but preferably it is a cam or a cone. Preferably the cam or cone is moved into and out of the bias position by a weight mechanism which causes the protrusion of the retention member in accordance with a given orientation of the plunger.

According to another preferred embodiment, the actuation member has a rod portion and a nose portion and the locking member is, in the unlocked position, located between the plunger and the nose portion. Preferably the actuation member is movable longitudinally along the bore in the plunger and preferably the retention member comprises a pin. In a particularly preferred embodiment, there is more than one pin.

According to a still further preferred embodiment, the plunger is adapted for manual filling of the syringe. By adapting the plunger for manual filling of the syringe, it is possible to hand fill syringes without the need to load them in the injector. This has the benefit of allowing a number of syringes to be pre-filled and thereby speed up the process of changing from one syringe to the next, and allows filling of a new syringe when the injector is injecting a previous patient. In addition a plunger according to this aspect of the invention can be used to hand fill a series of syringes and then be placed into the injector for injection of patients, thereby minimizing the need for separate hand filling devices.

Preferably the plunger according to this aspect of the invention is sufficiently shorter than the barrel of the syringe such that it can not reach the hub when the hub is located at the front most portion of the syringe barrel. In other words, the plunger is slightly shorter than the full syringe stroke, thereby is incapable of engaging the hub after the syringe has been used (assuming the syringe was fully expelled). A plunger/plunger device according to this aspect of the invention will decrease the chances of re-use of syringes (and thus cross-contamination) by being incapable of grasping and retracting the hub within the syringe. Preferably the plunger is sufficiently shorter than the barrel of the syringe such that it can not reach the hub when the hub is located at the front most portion of the syringe barrel.

According to a further aspect of the invention, there is provided a plunger for a syringe for use with a medical injector system, the syringe having a barrel and a hub slidingly engaging the barrel, the plunger comprising a retention member adapted to releasably engage an engaging portion of the hub to permit the hub to be selectively withdrawn along the barrel by the plunger; and a sensor to detect a level of engagement between the plunger and the hub.

A sensor according to this aspect of the invention may be any suitable sensor, such as a mechanical, electromagnetic or light sensor. Preferably the sensor detects full engagement between the plunger and hub. Where the sensor is a light sensor, then preferably it comprises a fibre optic cable.

According to one preferred embodiment, an optic fibre is embedded inside the plunger having one end exposed and flush with the surface of the plunger, and carefully positioned so that the end is masked by the hub just as the plunger fully engages the hub. The flexible fibre is routed out the rear end of the plunger, and via a suitable slack loop the other end of the fibre is connected to a photo detector which can respond to light transmitted through the fibre. Note that the plunger moves back and forth often, and so the fibre is a convenient and reliable means for communicating with the plunger. For the present invention the hub is made from opaque material, whilst the syringe barrel is transparent.

The injector is always used in a normally illuminated environment, and hence the fibre normally "sees" light (in the absence of a syringe hub). Of course, if the room lights are inadequate, the plunger can be illuminated by the injector with visible or infrared light. As the plunger engages the hub, the ambient light is cut off from the tip of the fibre, signalling the photo detector and Control Unit.

This device detects when the plunger has entered the piston, and when connected to the Injector Control Unit, provides the following benefits and enhancements:

(a) where the syringe has been pre-filled, the plunger must be engaged with the hub prior to initiating the injection, so that when the injector is started the hub begins expelling immediately. This device enables the injector to safely and accurately engage the hub and plunger, without pushing the hub (which could cause unwanted waste and mess).

(b) If used in association with the syringe sensing system described below, where the syringe has been pre-filled or the hub is not fully retracted, the plunger can automatically advance to engage the hub, then stop accurately.

(c) Where an automatically (for example, electronically) controlled hub and plunger engagement mechanism is employed, this sensor can be used to indicate that the piston retention mechanism is ready for locking.

(d) If used in association with a gravity locked plunger and a syringe presence sensor, this device can signal whether the hub is fully retracted when the syringe is first loaded, thereby confirming whether the syringe is new, or alerting the operator that the syringe has been used and may be contaminated.

(e) The device can also generate a signal if the piston becomes detached during retraction or filling.

According to a still further aspect of the invention there is provided a device for manually fling a syringe for use with a medical injector system, the syringe having a barrel and a hub slidingly engaging the barrel, the device comprising a plunger and a retention member adapted to releasably engage an engaging portion of the hub to permit the hub to be selectively withdrawn along the barrel by the plunger.

Such a device enables the operator to hand fill syringes without the need to load them in the injector. This has the benefits of allowing a number of syringes to be pre-filled and thereby speed up the process of changing from one syringe to the next, and allows filling of a new syringe when the injector is injecting a previous patient. In addition a device according to this aspect of the invention can be used to hand fill a series of syringes and then be placed into the injector for injection of patients, thereby minimizing the need for separate hand filling devices.

Preferably a device according to this aspect of the invention is sufficiently shorter than the barrel of the syringe such that it can not reach the hub when the hub is located at the front most portion of the syringe barrel. In other words, the device is slightly shorter than the full syringe stroke, thereby is incapable of engaging the hub after the syringe has been used (assuming the syringe was fully expelled). A device according to this aspect of the invention will decrease the chances of re-use of syringes (and thus cross-contamination) by being incapable of grasping and retracting the hub within the syringe. Preferably the device is sufficiently shorter than the barrel of the syringe such that it can not reach the hub when the hub is located at the front most portion of the syringe barrel.

Preferably the retention member is mechanically and/or electrically releasably engaged with the hub.

According to another preferred embodiment, the releasable engagement is at least partly actuated by a weight mechanism. According to another preferred embodiment, the releasable engagement is actuated by retraction of the plunger. Preferably the retention member is biased away from engagement with the hub.

According to a further preferred embodiment the retention member comprises an actuation member disposed at least partially within a bore defined in the plunger and a locking member is located at or adjacent one end of the retention member and/or plunger, the locking member being movable by the retention member into or out of engagement with the engaging portion of the hub. The retention member may be of any suitable form, it may be a cam, it may be a cone.

According to another preferred embodiment the actuation member has a rod portion and a nose portion and the locking member is, in the unlocked position, located between the plunger and the nose portion. Preferably the retention member comprises a pin.

According to another aspect of the invention, there is provided a method for hand filling a syringe comprising a hub according to the present invention and a device for hand filling according to the present invention comprising the steps of, (i) introducing the device into the syringe barrel and engaging the device with the inner surface of the hub (ii) activating the device such that the retention member engages the engaging portion of the hub; and (iii) withdrawing the engaged hub along the syringe barrel whilst drawing liquid into the syringe.

According to a further aspect of the invention, there is provided a syringe for use with a medical injector system including a hub as described above.

According to a further aspect of the invention, there is provided a syringe for use with a medical injector system including a plunger as described above.

In a particularly preferred embodiment of a syringe according to this aspect of the invention, it comprises a plunger as described above and a hub as described above.

According to another aspect of the invention, there is provided a sensing system for use with a medical injector system comprising a sensing member to detect the presence of a syringe holder associated with the medical injector system. The sensor may be of any suitable type such as a light sensor, mechanical sensor or electromagnetic sensor. Preferably it is a light sensor. Where the sensor is a light sensor, then preferably the sensing system further comprises a reflecting member to reflect light to the sensing member. The reflecting member may be associated with any suitable component, such as the syringe, or the injector system. The sensor system may alternatively comprise a light interruptor, contacts, or mechanical switch component.

According to one preferred embodiment, during assembly of the holder a syringe stop (or bush) and spring stop are normally fixed in place inside the holder by any suitable means sch as cement, screws, or pins. Both stops have a small longitudinal groove in their outer surface to support a slidable syringe flag, which, together with the flag spring are held in place by the two stops. The compression spring is lodged between the rear fixed spring stop and the flag tabs, thereby biasing the flag forward. With no syringe loaded the flag protrudes forward of the syringe stop, and its tabs lodge against the rear of the syringe stop. A secondary function of the syringe stop is to bear and centre the plunger, and prevent stray fluid around and/or from the syringe from entering the injector.

In brief, a sensing system according to this aspect of the invention can perform at least three functions:

1 Syringe ejector: According to one embodiment, the sensing system comprises a flag which is slidingly mounted in a groove, and is biased forward by a flag spring. As the syringe is loaded into the holder the rear rim of the syringe strikes the flag, pushing it rearward and compressing the flag spring until the tip of the flag is flush with the syringe stop. When the syringe catch is opened the syringe is partially ejected forward by the flag, making the syringe easier to grasp and remove.

2 Anti Rotation Device: Unlike most other syringe/holder arrangements, with the present invention the syringe can be rotated about its axis. When a tube is attached to the syringe (after it has been loaded), the operator needs to twist the connection clockwise to engage and lock the connection to the syringe thread. To restrain the syringe from rotating it would ordinarily need to be held with the other hand, however the flag may perform this role. The forward tip of the flag is bevelled & sharpened, and thus can dig into the syringe and thereby decrease rotation of the syringe.

3 Syringe Sensor: In association with the sensing system the flag detects the presence of a syringe in the holder. Reflective infrared sensors such as Sharp GP2L24 are readily available examples of sensors that may be used as part of the system. As the flag is pushed back by the syringe the reflective rear end of the flag is detected by the sensor, which in turn may signal a controller associated with the injector system.

Electronic sensing of the syringe, coupled to a controller associated with the injector system enhances the functionality and safety of the injector. For example:

(a) To avoid cross infection from patient to patient it is important that the syringe is replaced before the injector can allow a subsequent filling or injection.

(b) Where a gravity operated plunger/hub locking mechanism is employed, the syringe should only be removed when the injector head is oriented horizontally (ie when the piston is unlocked)—if removal is attempted in the vertical orientation, the injector controller can alert the operator.

(c) In the case of an electrically operated piston lock, the injector controller can automatically lock following loading of a syringe.

(d) As with any injector, the syringe should not be removed unless the hub is unlocked from the plunger (otherwise the hub could be separated from the syringe barrel, potentially spilling contaminated fluid or drug). In the case of certain of the described embodiments the syringe is only able to be removed at the end of a forward (inject) stroke. Hence the controller must not allow retraction of the plunger until the sensor advises that the syringe has been removed following an injection.

(e) With all syringe holders, to avoid accidental opening or failure during an injection it is important that the device is fully locked in position before it can be used. If a syringe holder is not fully engaged with the injector system, it should be noted that the flag will not intersect the proximity sensor (preventing operation of the injector) until the holder is fully rotated to the locked position, and a syringe is present Similarly, a person skilled in the art will appreciate that configurations which do not utilize a flag but instead utilize some other form of sensing mechanism will have the same and other benefits. Other benefits of a sensor system according to the present aspect of the invention include:

(a) The sensitive electronic proximity sensor is fully protected from stray injection fluids which could damage or interfere with the sensor.

(b) Because the holder according to certain embodiments is able to be removed for washing, the sensor is not exposed to washing fluids.

(c) The system is solid state (apart from the flag) and therefore robust & reliable.

According to a further aspect of the invention, there is provided a medical injector system for injecting fluid from a syringe into a patient, the syringe having a barrel and a hub slidingly engaging the barrel, the hub comprising all inner surface having an engaging portion adapted to be releasably engaged by a plunger, the injector system comprising: (i) a plunger for driving the hub, the plunger comprising a retention member adapted to releasably engage the engaging portion of the hub; and (ii) a syringe holder comprising: a cradle member adapted to receive a barrel of the syringe; and a pivotable catch to releasable lock the syringe in the cradle member. Preferably there is also provided a positioning device located on the cradle member to locate one end of the syringe in a predetermined location in the cradle member According to a preferred embodiment, the syringe holder comprises an engagement portion to enable simple releaseable engagement with a medical injector. Preferably the engagement portion of the syringe holder comprises a locking member. The locking member of the syringe holder may comprise any suitable means of locking. Preferably it comprises a slot or a pin.

According to a further preferred embodiment, the medical injector system further comprises (i) a tube adapted to be connected to syringe to conduct fluid into or out of the syringe; and (ii) a connector to connect the tube to a vessel containing medical fluid and thereby enable withdrawal of the fluid from the vessel into the syringe wherein the connector comprises a hollow spike to create an aperture through a bung in the vessel upon piercing of the bung by the spike.

Preferably the connector further comprises (i) a male luer portion having a locking collar; and (ii) a disengagement portion to enable permanent disengagement of the spike from the male luer portion. Preferably the disengagement portion comprises a frangible neck. Preferably the spike comprises a barbed portion to resist removal of the spike from the vessel.

It will be readily appreciated that the connections may comprise any convenient connection means known in the art such as bayonet, snaplock or screw connections. The spike may be broken off to leave a male luer tip on the end of an associated tube.

The combination spike, optionally a frangible (vented or sealed) spike, and male luer connector device may be permanently connected to a tube and syringe. Using this combination, optimally the device can only be filled once, and thereby cannot possibly infect a multi-dose bottle of medical fluid or cross infect another patient.

If the spike connector is made as a frangible part of the connector, and is permanently attached to the tube and syringe, it is very difficult for the syringe to be refilled, and thereby cross infect the bottle or another patient. In addition, such an arrangement further reduces material costs. The syringe, spike connector means and frangible spike may be supplied as one set. Preferably, the spike connector can be snapped off prior to attachment of the tube to an intravenous catheter and hence to a patient.

According to another preferred embodiment, the medical injector system further comprises a clamp between the tube and a male luer connector of the syringe, the clamp being moveable into a locking thread of the male luer connector thereby clamping the tube to the male luer connector. Preferably the clamp comprises a gripping portion to increase the grip between it and the tube. The gripping portion may be of any suitable type, such as barbed rings, barbed teeth, a screw thread, serrated grip, a ridge (for example an annular ridge), a rear flange or an internal taper. In a particularly preferred embodiment the clamp is tamper evident.

According to a particularly preferred embodiment, the medical injector system further comprises a base member and a sensor to detect orientation of the syringe holder with respect to the base member. Preferably the sensor detects the angle between the syringe holder and base member.

According to another preferred embodiment, there is provided a switch to automatically initiate or inhibit movement of the plunger in the barrel depending on its orientation. The switch may be activated by any suitable mechanism. According to one preferred embodiment, it is activated by a weight mechanism.

According to a particularly preferred embodiment, there is further provided a controller to control the plunger. Preferably at least some of the injector operation may be automated by electronics or software. For example, the injector may have one or more gravity or syringe angle operated tilt switches to automatically initiate or inhibit movement of at least the syringe during operation of the injector.

According to another preferred embodiment, the system has a controller and a sensor to detect orientation of the syringe holder with respect to the base member. The sensor may sense any suitable feature, but preferably it detects the angle between the syringe holder and base member.

Preferably the controller is operable to move the plunger to test patency of an intravascular catheter connected via a tube to the syringe. At present this has to be checked manually, with great care being exercised so as to avoid damaging, and possibly rupturing the vein.

Preferably a medical injector system according to this embodiment will utilize a hub, plunger, syringe holder, 1 or more sensor(s) and/or syringe as herein described.

Where there is a sensor, then preferably it communicates with a controller associated with the injector system to further control the movement of the plunger. Preferably the communication enables engagement of the plunger and the hub without thereby moving the hub. According to one preferred embodiment, the communication enables releasable locking of the hub to the plunger. According to another preferred embodiment, the communication causes releasable locking of the hub to the plunger. According to a still further preferred embodiment, the communication enables detection of used syringes.

According to yet another preferred embodiment, a signal is created if the sensor detects the hub at a position forward of its most retracted state. According to another preferred embodiment, the communication enables detection of errors. Preferably a signal is created if the hub and plunger disengage prematurely.

According to another preferred embodiment, the communication enables movement of the plunger to either fill or expel fluid from the syringe. For example, the communication may either enable or disable movement of the plunger. This may occur for a variety of reasons, or based on a variety of stimuli. For example, movement of the plunger may be disabled after use, if the syringe has not been removed, or before use if the syringe has not been engaged to a specified level.

According to another preferred embodiment, a signal is created if removal of the syringe is attempted at certain orientations of the syringe. Preferably the signal is created if removal is attempted while the syringe is in a substantially vertical orientation.

According to another preferred embodiment, a signal is created indicating the syringe has not been removed. Preferably the signal is created if the syringe is not removed immediately following use.

According to a particularly preferred embodiment of the invention, there is provided method of filling a syringe with medical fluid from a sealed vessel the syringe for use with a medical injector system comprising the steps of: (i) elevating the front portion of the syringe relative to the back portion; (ii) advancing a plunger to a position within the syringe corresponding to a predetermined patient dose; (iii) controlling movement of the plunger in a sequence of forward and backward movements to expel air from the syringe and any attached tube into the vessel bottle, and draw the desired dose of fluid into the syringe.

According to a still further aspect of the invention, there is provided a method of filing a syringe with medical fluid from a sealed vessel, the syringe for use with a medical injector system as herein described, comprising the steps of: (i) elevating the front portion of the syringe relative to the back portion; (ii) advancing the plunger to a position within the syringe corresponding to a predetermined patient dose; and (iii) controlling movement of the plunger in a sequence of forward and backward movements to expel air from the syringe and any attached tube into the vessel bottle, and draw the desired dose of fluid into the syringe.

According to these methods, all outside air is excluded in order to substantially reduce the chances of introducing microbes to the fluid and patient. Furthermore, the method provides a convenient and expedient way of filling and purging both the syringe and the tube in one operation, and as well as reducing costs of materials used and speed of syringe filling as compared with traditional methods. Filling and purging of the syringe and associated extension tube may be carried out in one combined operation. According to another preferred embodiment, all elements of the fluid path are connected as one sealed system.

According to this embodiment, the combined forces of air pressure in the bottle with partial vacuum in the syringe generate a greater pressure difference between the two vessels than conventional vented systems, thereby resulting in a faster syringe filling time.

In a preferred embodiment of the method of filling, after driving of the spike connector into the bung and selection of an automatic "FILL" function on the injector, the injector then performs a sequence of controlled forward and back movements of the piston, such that all air in the syringe and tube is transferred to the bottle, and the desired dose of fluid is drawn into the syringe.

According to another preferred embodiment of the method, it further comprises the step of automatically restricting the direction of movement of the plunger depending on the orientation of the syringe. Preferably the plunger may move either forward or backward when oriented with its front portion elevated with respect to its back portion and only in the forward direction when oriented with the back portion elevated with respect to its front portion. This reduced the chance of an air bubble being injected into a patient by ensuring that air bubbles will be at the back of the syringe. Preferably this step may be enabled by a tilt switch or sensor so that the syringe is inclined with the front portion elevated when expelling air and filling so to minimise trapping of air in the syringe.

According to another aspect of the invention there is provided a method of injecting a patient using a medical injector system as herein described comprising the steps of (i) engaging the plunger with the hub, (ii) driving the hub along the syringe barrel; and (ii) expelling fluid from the syringe into a patient.

According to a further aspect of the invention, there is provided a method for engaging a syringe holder as herein described with a medical injector according to claim [ind], comprising the steps of: (i) aligning the engaging portion of the syringe holder with a complimentary portion on the medical injector; and (ii) engaging the syringe holder with the medical injector.

According to one preferred embodiment, there is the further step of detecting a level of engagement between the syringe holder and the medical injector system.

According to a still further aspect of the invention, there is provided a method for disengaging a syringe holder as herein described from a medical injector as herein described comprising the steps of: (i) disengaging the engaging portion of the syringe holder from the medical injector; and (ii) removing the syringe holder from the medical injector.

Preferably there is the further step of detecting a level of disengagement between the syringe holder and the medical injector system.

According to a further aspect of the invention, there is provided a method for loading a syringe into a syringe holder associated with a medical injector system as herein described, comprising the steps of: (i) inserting the syringe barrel in the cradle member such that the catch is displaced; and (ii) allowing the catch mechanism to return into its biased position to engage the syringe and thereby retain the syringe in the cradle member.

According to a still further aspect of the invention there is provided a method for removing a syringe from a syringe holder associated with a medical injector system as herein described comprising the steps of: (i) releasing the catch to unlock the syringe; and (ii) withdrawing the syringe from the cradle member.

According to a further aspect of the invention, there is provided a method for loading a syringe into a syringe holder of a medical injector system as herein described comprising the steps of: (i) inserting the syringe barrel in a cradle of the syringe holder; and (ii) sensing the presence of the syringe in the holder with a sensing member associated with the sensing system.

According to a further aspect of the invention, there is provided a method for removing a syringe from a syringe holder of a medical injector system as herein described comprising the steps of: (i) withdrawing the syringe from the cradle member; and (ii) sensing the absence of a syringe in the holder with a sensing member associated with the sensing system. Preferably there is the further step of automatically retracting the plunger after withdrawal of the syringe. Preferably there is a still further step of restricting retraction of the plunger until the syringe has been withdrawn. According to one preferred embodiment, there is a further step of prompting retraction of the plunger after the syringe has been withdrawn.

According to another aspect of the invention, there is provided a method of connecting a syringe hub to a plunger using a medical injector system as herein described comprising the steps of: (i) introducing the plunger into a syringe barrel within which the hub is slidingly engaged and engaging the plunger with the inner surface of the hub; and (ii) activating the plunger such that a retention member engages the engaging portion of the hub. Preferably there is the further step of detecting a level of engagement between the plunger and the hub.

According to a further aspect of the invention, there is provided a method for modifying a medical injector system comprising a syringe holder, comprising the steps of: (i) replacing the syringe holder with a syringe holder as herein described; and (ii) attaching a plunger as herein described.

According to another aspect of the invention, there is provided a method for modifying a medical injector system comprising a syringe holder, comprising the steps of: (i) replacing the syringe holder with a syringe holder as herein described; and (ii) attaching a plunger as herein described.

According to a further aspect of the invention, there is provided a method for modifying a medical injector system comprising the steps of: (i) replacing the syringe holder with a syringe holder as herein described; and (ii) attaching a plunger as herein described.

According to another aspect of the invention, there is provided a method for modifying a medical injector system comprising the step of adding a sensing system as herein described.

BRIEF DESCRIPTION OF THE DRAWINGS

FIG. 2a shows various components of the syringe as used in the present invention;

FIG. 2b shows an assembled syringe;

FIG. 2c shows the assembled syringe of FIG. 2b in conjunction with a plunger;

FIG. 3a shows oblique side views of the hub;

FIG. 3b shows a side view of the hub;

FIG. 3c shows a cross sectional view of the assembled hub and seal;

FIG. 3d shows a front view of the hub;

FIG. 3e shows a rear view of the hub;

FIG. 4a shows alternative conformations of the engaging portion of the hub, in the form of grooves;

FIG. 4b shows a cross section of the hub and engaging portion;

FIG. 5 shows example dimensions of the hub;

FIG. 7 shows a cross sectional side view of one possible embodiment of the plunger/hub interlocking arrangement;

FIG. 8 shows a front cross-section along the line A-A of FIG. 7;

FIG. 9 shows an alternative arrangement of FIG. 8;

FIG. 10 shows an alternative example of the plunger/hub interlocking arrangement;

FIG. 11 shows a front cross-section along the line A-A of FIG. 10;

FIG. 12 shows an alternative arrangement of FIG. 11;

FIG. 15 shows yet another alternative of the plunger/hub interlocking arrangement;

FIG. 16 shows a front cross-section along the line A-A of FIG. 15 showing the cam in detail;

FIG. 18c shows a side oblique view of the syringe holder and catch of FIG. 18a;

FIG. 19 shows a cross section side view of the syringe holder/syringe combination within the sleeve of the injector, with the syringe retained by a catch;

FIG. 20 shows a cross-section along the line A-A of FIG. 19;

FIG. 21 shows a cross-section along the line B-B of FIG. 19;

FIG. 23c shows a perspective view of a syringe with a concave front flange;

FIG. 23d shows a cross-sectional view of a syringe with a concave front flange;

FIG. 23e shows a cross-sectional view of a dovetail catch according to the present invention;

FIG. 26 shows various views of an example of a combination male luer connector and frangible spike;

FIG. 27 shows an example of a male Luer Connector with barbed frangible spike, and locking collar, as follows:

FIG. 29 illustrates a typical syringe male Luer lock connector;

FIG. 31 demonstrates various views of the basic or Plain form of a clamp according to the present invention;

FIG. 31a demonstrates a side view of the Plain clamp;

FIG. 31b demonstrates an oblique view of the Plain clamp;

FIG. 31c depicts the Plain Clamp in longitudinal axial cross-section;

FIG. 31d depicts a longitudinal axial cross-sectional view of a soft plastic tube pushed over the tip of a luer, and the plain clamp pressed into the female locking thread of a luer locking syringe;

FIG. 32 depicts a clamp with barbed rings;

FIG. 32a depicts an oblique outer view of a clamp having annular barbed rings added to the outer surface;

FIG. 32b depicts a longitudinal axial cross-sectional view of a clamp having annular barbed rings added to the outer surface;

FIG. 32c depicts a longitudinal axial cross-sectional view of a barbed clamp pressed into the female locking thread of a luer locking syringe, and clamping a tube onto the associated male luer tip;

FIG. 33 depicts a clamp with male threads;

FIGS. 34 & 35 illustrate flanges added to the rear end of clamps;

FIG. 37a illustrates an exploded perspective view of a syringe holder with a bayonet attachment, loaded syringe and sensing system to detect the presence of a syringe;

FIG. 37b illustrates a cross-sectional view of the holder and syringe of FIG. 37a;

FIG. 37c illustrates a syringe flag for use with the syringe sensing system;

FIG. 38a illustrates a longitudinal cross-sectional view of a syringe holder with a bayonet attachment, loaded syringe and sensing system to detect the presence of a syringe;

FIG. 38b illustrates a lateral cross sectional view of the syringe holder and syringe of FIG. 38a through the line MM;

FIG. 38c illustrates a lateral cross sectional view of the syringe holder and syringe of FIG. 38a through the line LL;

FIG. 38d illustrates a lateral cross sectional view of the syringe holder and syringe of FIG. 38a through the line KK;

FIG. 38e illustrates a syringe flag for use with the syringe sensing system;

FIG. 39a illustrates a cross sectional view of a syringe in a syringe holder demonstrating a particularly preferred embodiment of the engagement mechanism between the hub and plunger during movement of the plunger to expel fluid from the syringe;

FIG. 39b illustrates the syringe and syringe holder of FIG. 39a during movement of the plunger to draw fluid into the syringe;

DESCRIPTION OF PREFERRED EMBODIMENTS

Figure 1:
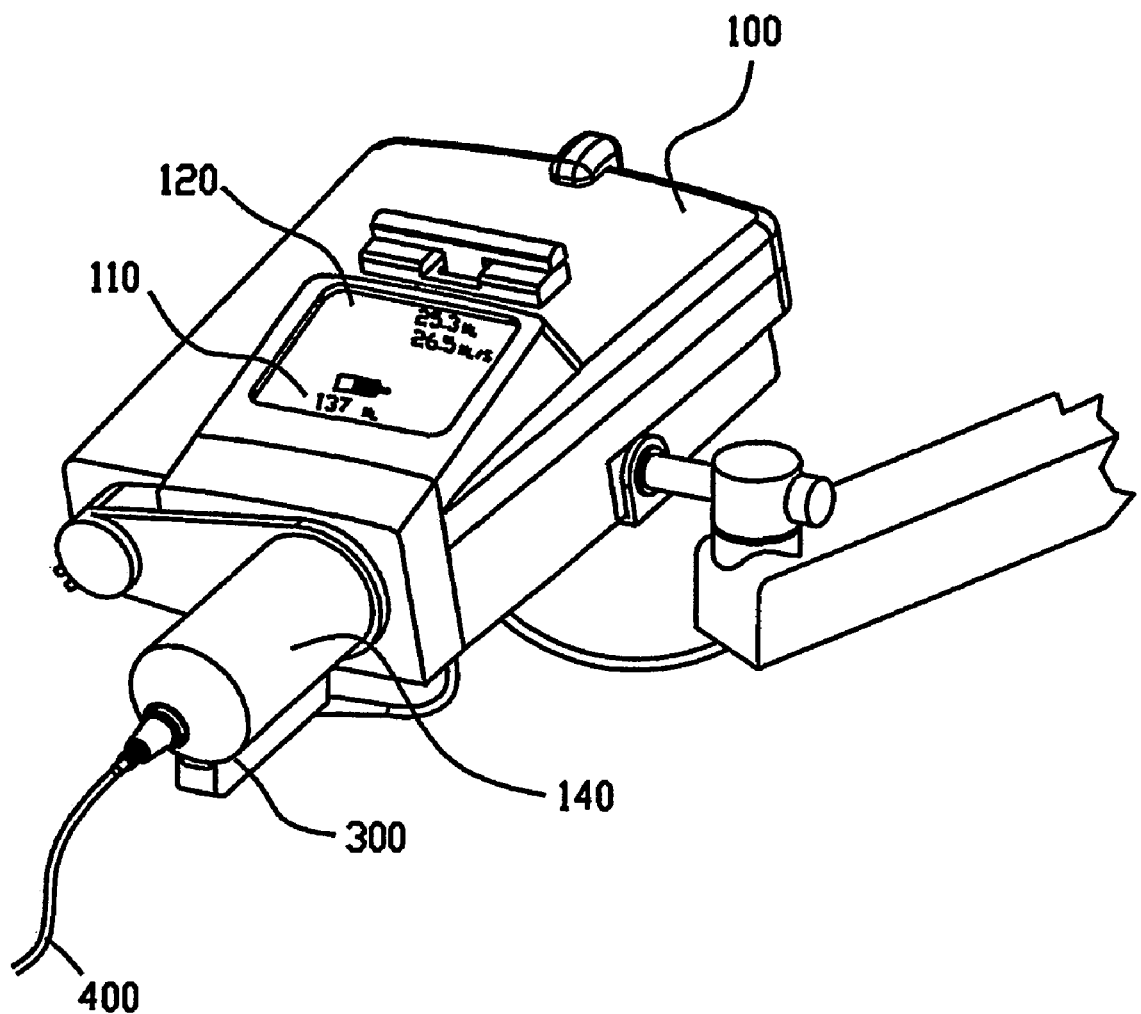
FIG. 1 shows a prior-art injector with a syringe loaded.

A typical injector system used for similar applications as the present invention includes an automatic injector device 100. The injector will normally have a data entry pad 110 together with a display 120 for entering data and viewing data respectively. The type of data that may be entered into the system includes injecting rates and volumes. The system according to the prior art includes a pressure jacket or sleeve 140 which is connected to injector 100 for retaining an appropriate syringe 300. Tube 400 connects syringe 300 to the patient (not shown). The prior-art arrangement of the injector as shown in FIG. 1 suffers from a number of disadvantages. Firstly, to install syringe 300 into injector 100, sleeve 140 must first be removed or opened to allow syringe 300 to be rear- or breech-loaded into the sleeve 140 and fixed therein by reattaching or closing sleeve 140. In some cases, sleeve 140 is completely closed, like that shown in FIG. 1, requiring that tube 400 be attached after loading and removed before unloading the syringe 300. This increases the amount of time required to load the syringe, and increases the risks of spillage of contaminated blood. These disadvantages are addressed by the system of the present invention, which allows the syringe 300 to be loaded into the injector 100 directly from the front and does not require sleeve 200 to be removed, loaded and re-inserted into injector 100.

To allow syringe 300 to be inserted easily from the front, the syringe itself may be flangeless. That is, the outer cylindrical surface of the syringe may be free of any interfering projections which normally exist on syringes.

A syringe in accordance with the present invention is shown in FIG. 2a wherein there is shown the barrel of the syringe 300, into which are inserted a hub 310 and corresponding seal 320. Upon assembly of hub 310 and barrel 300, the syringe appears as shown in FIG. 2b. The hub and seal can be manufactured as one component [illustrated in FIG. 4d]. For the preferred embodiment the hub is made from semi-rigid plastic, whilst the seal is made from elastomer. In practice, manufacturers of the syringe could sell the syringe barrel either empty, or pre-filed with the required amount of medical fluid to be injected into the patient, which is retained inside the barrel by the hub and seal combination.

To inject the drug contained within the syringe, a plunger 130, which is operatively connected to the injector 100, engages the inner surface of the hub 310 and it is actuated by the injector 100 in accordance with the required controlled motion. As plunger 130 is driven into syringe barrel 300, this causes hub 310 and seal 320 to be driven relatively towards the other end of barrel 300, thereby injecting the drug through tube 400 into the patient (not shown). The hub according to the present invention may be made of any suitable semi-rigid plastic such as polypropylene or styrene, whilst the seal could be made from an elastomeric substance such as Santoprene, Kraton, Improflex, Kraiburg etc.

Figure 4C:
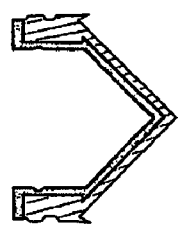
FIG. 4c shows a cross section of the hub and engaging portion, having a conventional seal, with an extended leading edge.
Figure 4D:
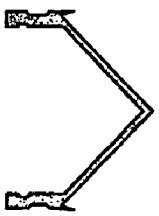
FIG. 4d shows a cross section of the hub and engaging portion, having a seal integral to the hub.
Figure 4E:
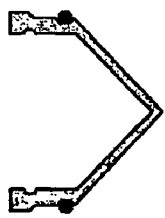
FIG. 4e shows a cross section of the hub and engaging portion, having an o-ring seal.
Figure 4F:
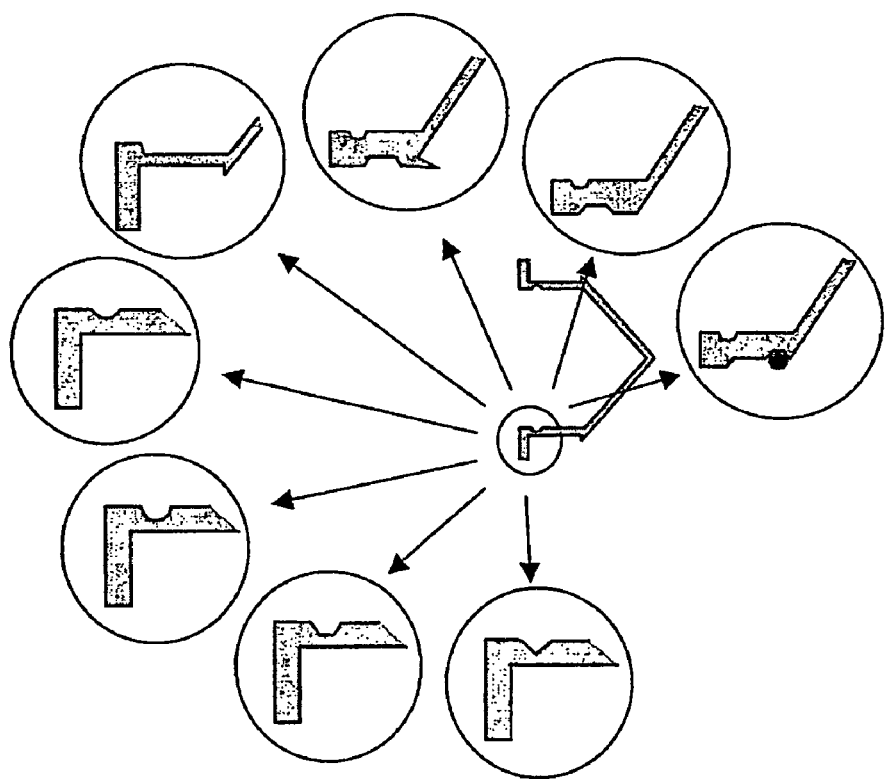
FIG. 4f shows further alternative conformations of the engaging portion of the hub.

The hub 310 is shown from various angles in FIG. 3. In particular, annular groove 311 is shown on the inside surface of hub 310. The cross-section of the groove may take on any appropriate shape as shown in FIG. 4a including, semi-circular, squared and triangular cross-sections. In addition, FIG. 4c shows a hub assembled with a seal 320 having an extended leading edge on the seal lip to improve sealing under pressure. FIG. 4d shows a hub and seal combined in one piece which provides the benefits of reduced manufacturing costs. Other advantages of this arrangement are also apparent such as (1) increased lubricity if a low friction material such as polypropylene is used, (2) elimination of silicone or other lubricants, (3) reduction of particles in syringe; and (4) reduced/eliminated assembly costs. The purpose of this groove will be described in more detail below. FIG. 4e further depicts a hub having an annular seal 312 seen in cross section.

The dimensions of the hub will obviously be made in accordance with the particular syringe being used. By way of example, it is envisaged that they will typically be of the order of the dimensions shown in FIG. 5.

Figure 6:
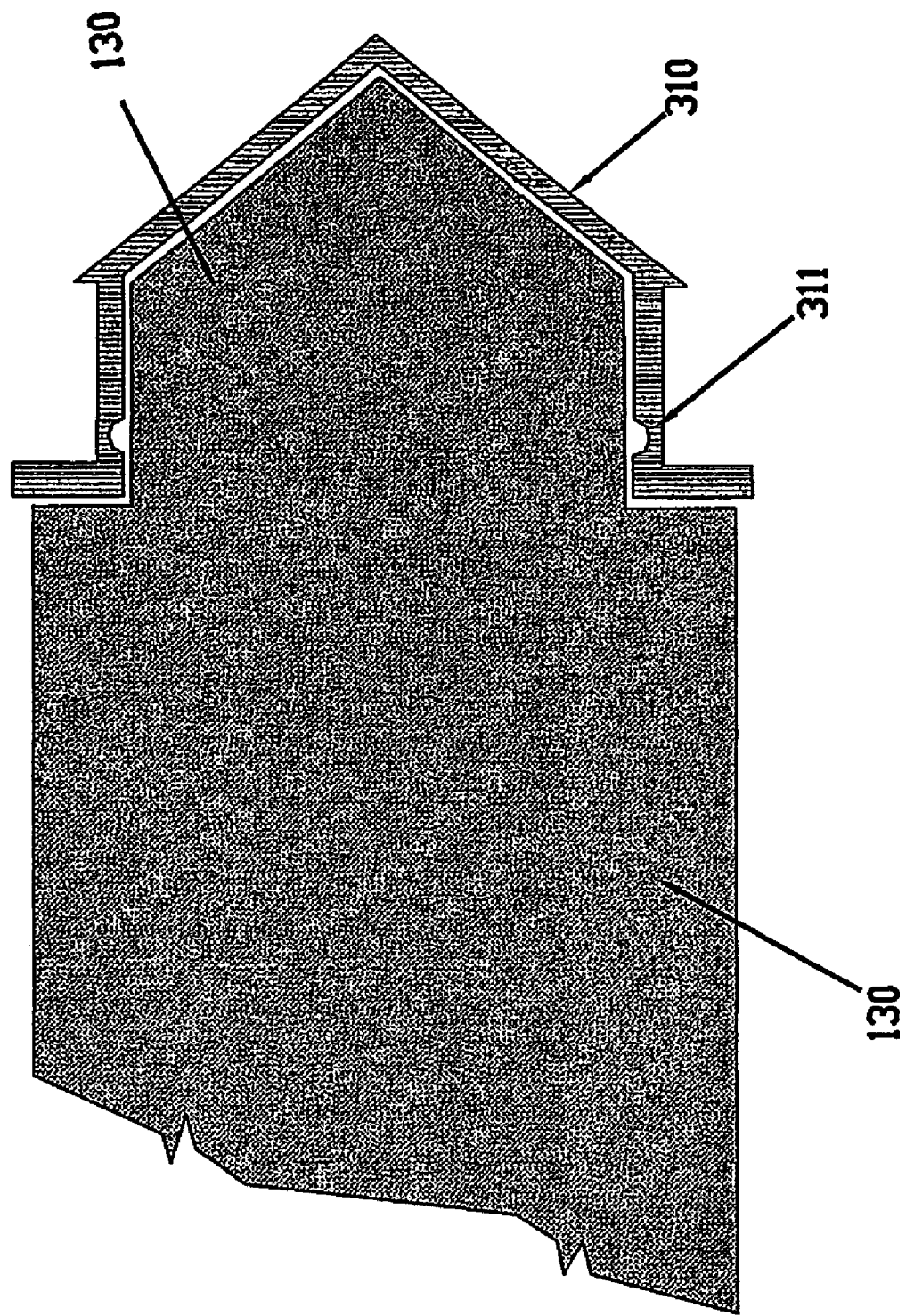
FIG. 6 shows a cross-section of the plunger engaging the hub.

The tip of injector plunger 130 is formed so as to effectively engage with the inner surface of hub 310 as clearly shown in FIG. 6. Annular groove 311 is also clearly seen as defining a space between the wall of the hub 310 and the surface of the tip of injector plunger 130. This engagement between plunger 130 and hub 310 is such as to provide a form fit so that the force actuated by injector plunger 130 is efficiently imparted to hub 310, causing the hub and associated seal 320 (not shown in FIG. 6) to travel forward along the inner surface of syringe 300, and thereby expel the contents of the syringe.

It is envisaged that injector plunger 130 will be useful for emptying a pre-filled syringe.

However, empty new syringes are often filled just prior to use within such injectors, which requires the hub and seal to be retracted by plunger 130. It will be seen that by itself, plunger 130 does not grip or retain hub 310. Therefore another mechanism is required to allow plunger 130 to effectively grip hub 310 and enable it to withdraw the hub and seal from the syringe barrel. Groove 311 provides such a mechanism.

As can be seen in FIG. 7, upon retraction of the plunger, pins 142 protrude from plunger 130 at the location of groove or recess 311. Pins 142, filling groove or recess 311, act as retention members allowing hub 310 to be withdrawn from the syringe barrel 300 as injector plunger 130 is withdrawn. The mechanism by which pins 142 are caused to enter groove or recess 311 may take on many forms as now discussed in further detail in FIGS. 7 to 16.

In one embodiment as shown in FIG. 7, plunger 130 may include actuating rod 140 with a cam element 141 projecting from a nose end of actuating rod 140. Cam element 141 is an oval-shaped rod, which upon insertion of plunger 130 into syringe barrel 300, lies in a horizontal plane. Pins 142 terminate at an inwardly projecting end with curved contacting surface 147. Pins 142 rest against the outer surface of cam element 141 and are biased towards cam element 141 via springs 143. In this position, the outer ends of pins 142 lie within or below the surface of plunger 130. Once the plunger/hub/seal arrangement has reached the end of syringe barrel 300, and is required to be retracted from the barrel, actuating rod 140 may be rotated about its axis, such that cam element 141 now lies in a vertical plane as shown in FIG. 8. As cam element 141 rotates, pins 142, which are biased against the surface of cam element 141, are caused to be pushed out towards the surface of plunger 130 such that their outer ends protrude from plunger 130 and are received in groove or recess 311 as shown in FIG. 7. In this position, hub 310 is retained by plunger 130 and is able to be withdrawn from syringe barrel 300. As discussed above, this mechanism may take on many forms, a further one of which is shown in FIG. 9. In this case, cam element 141 may have a square cross-section which allows the four pins 142 to be extended from plunger 130 to be received in groove or recess 311. The heads of pins 142 are biased against the four sides of cam element 141 and upon rotation of cam element of 141, are caused to be biased against the four corners of cam element 141, resulting in pins 142 protruding from the surface of plunger 130.

Figure 13:
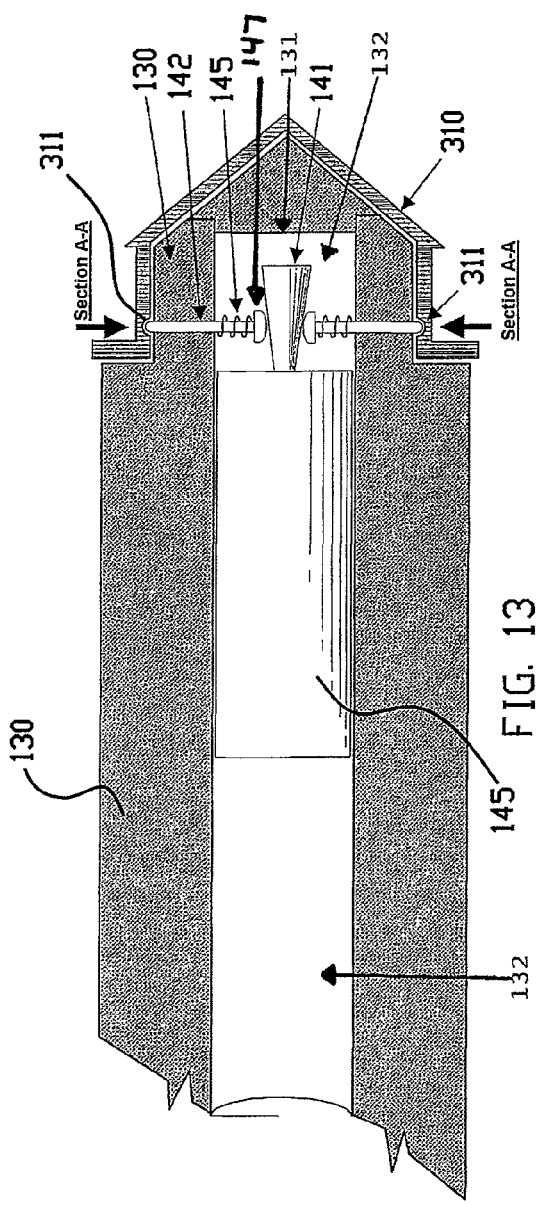
FIG. 13 shows an alternative arrangement for the plunger/hub interlocking arrangement.
Figure 14:
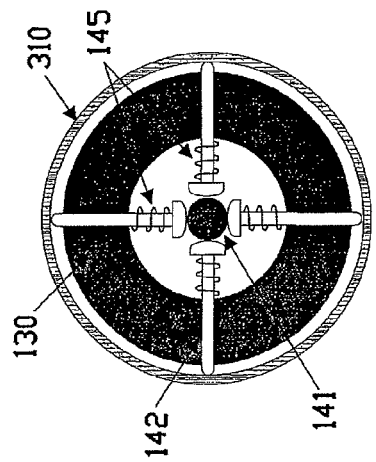
FIG. 14 shows a front cross-section along the line A-A of FIG. 13.

In another embodiment of a mechanism for actuating pins 142 shown in FIGS. 10 to 12, cam element 141 is replaced by a cone element 144. Pins 142 terminate at an inwardly projecting end with curved contacting surface 147. In this embodiment, curved contacting surface 147 of pins 142 are biased against the outer surface of cone element 144 by springs 143 as in the previous embodiment. In use, plunger 130 is inserted into syringe barrel 300 and hub 310, whilst actuating rod 140 is pressed as far as possible against the forward surface 131 of plunger element 130. In this position, pins 142 rest against the narrowest portion of cone element 144 and are biased away from the outer surface of plunger 130 by springs 143. Before or upon retraction of plunger 130, actuating rod 140 is pulled away from surface 131 causing pins 142 to slide along cone element 144 up the cone surface. This causes pins 142 to be pushed out and to protrude from the outer surface of plunger 130 to be received in groove or recess 311. Hub 310 is thereby retained by plunger 130 and able to be moved along the syringe barrel 300. This arrangement also allows for four pins to be used to be received in groove or recess 311 as shown in FIG. 12. The cone arrangement of FIGS. 10-12 may also be used in a "gravity operated" locking mechanism whereby plunger 130 only retains hub 310 when the syringe assumes a particular orientation. Such an arrangement (as shown in FIGS. 13 and 14) is particularly useful when it is desired to prevent re-use of a syringe between patients. This is desirable to reduce the risks of cross-patient infection or contamination.

It will be appreciated that it is advisable to tilt the injector upward during syringe filling in order to ensure that air is kept at the syringe outlet for subsequent removal prior to injection. Additionally, it is advisable to tilt the injector downward during injection (to keep any remaining air in the syringe by the hub so that any air will remain in the tubing between the syringe and the patient after the injection, and therefore not enter the patient.

Generally, new syringes are supplied with the hub and seal arrangement placed in a fully retracted position, ie near the back of syringe barrel 300. It is also customary to retract the plunger following each use. In one embodiment, with the injection unit 100 oriented down, the syringe is loaded through the front end of the cylindrical sleeve in the injector unit, which aligns the syringe with the plunger. As a consequence, hub 310 engages plunger 130. It should be noted that if a used syringe had been loaded, the hub would not engage the fully retracted plunger (i.e., because the hub would not be in the fully retracted position within the syringe barrel). To fill the syringe, the injector with the syringe loaded therein is then tilted vertically. As the injector unit is tilted vertically weight rod element 145 drops down within a cylindrical cavity 132 in plunger 130 as shown in FIG. 13. As weight rod element 145 drops, cone element 144 causes pins 142 to be pushed out to protrude from the outer surface of plunger 130 to be received in groove or recess 311 of hub 310. Thus, hub 310 is retained by plunger 130. Upon tilting up, plunger 130 is able (through an automatic tilt switch and controls) to push hub 310 and associated seal 320 (not shown) towards the top end of syringe barrel 300 until the plunger cannot advance any further and seal 320 rests up against the front end of syringe barrel 300, expelling the unwanted air.

Upon actuating the plunger in the reverse direction, hub 310 and seal 320 are retracted and the syringe is able to be filled. To inject the contents of the syringe into the patient, the injector unit is returned to a downward position and plunger 130 is once again advanced along syringe barrel 300, expelling the contents of the syringe. As the injector assembly assumes a downward orientation, weight rod element 145 returns to a forward-most position within cavity 132. This causes pins 142 to be retracted below the outer surface of plunger 130 due to springs 143 and due to the fact that the heads of pins 142 are now allowed to rest against the narrow portion of cone element 144. Upon completion of the injection procedure, plunger 130 is automatically retracted from syringe barrel 300 and, because pin elements 142 have been retracted into plunger 130, hub 310 is no longer retained by the plunger and therefore remains at the front-most portion of syringe barrel 300. Accordingly, the used syringe (whether just used, or later reloaded) cannot be reused because given that hub 310 has been advanced (at least partially) along the syringe barrel 300, the hub will not be engaged with the fully retracted plunger 130, and cannot be retained when the injector is tilted up.

If the injector unit was raised to assume a vertical position again, weight rod element 145 drops down due to gravity, causing pins 142 to extend beyond the top surface of plunger 130. If plunger 130 were advanced into the barrel 300, it will not be able to proceed past the back end of hub 310 due to the protrusion of the pins. This will alert the unit operator that the syringe has been used and prompt them to obtain an unused syringe.

Yet a further possible implementation of the locking mechanism involves the use of cam element 154 connected to an actuating rod 133 which is contained within the body of plunger 130. This arrangement is shown in FIGS. 15 and 16. During the advancement of plunger 130/hub 310/seal 320 combination into the barrel 300 of the syringe, actuating rod 133 is orientated such that cam element 134 is positioned with its nose pointed downwards from the point of view of FIGS. 15 & 16, such that no part of cam element 134 protrudes from plunger 130. Once hub 310 with seal 320 (not shown in FIG. 15 or 16) is then required to be retracted, actuating rod 133 is rotated in the direction of the curved arrows such that the nose of cam element 134 protrudes from the surface of plunger 130 and is received in groove or recess 311. In this manner, hub 310 and connected seal 320 are retained by plunger 130 and may be retracted within the syringe barrel upon retraction of plunger 130.

It will also be appreciated that pin elements 142 (FIGS. 7 to 14) need not be individual pins but may take the form of a unitary ring within plunger 130 which may lie flush with or below the surface of plunger 130 during the advancing stage and which may be caused to expand to protrude from the surface of plunger 130 to be received in groove or recess 311.

Figure 17:
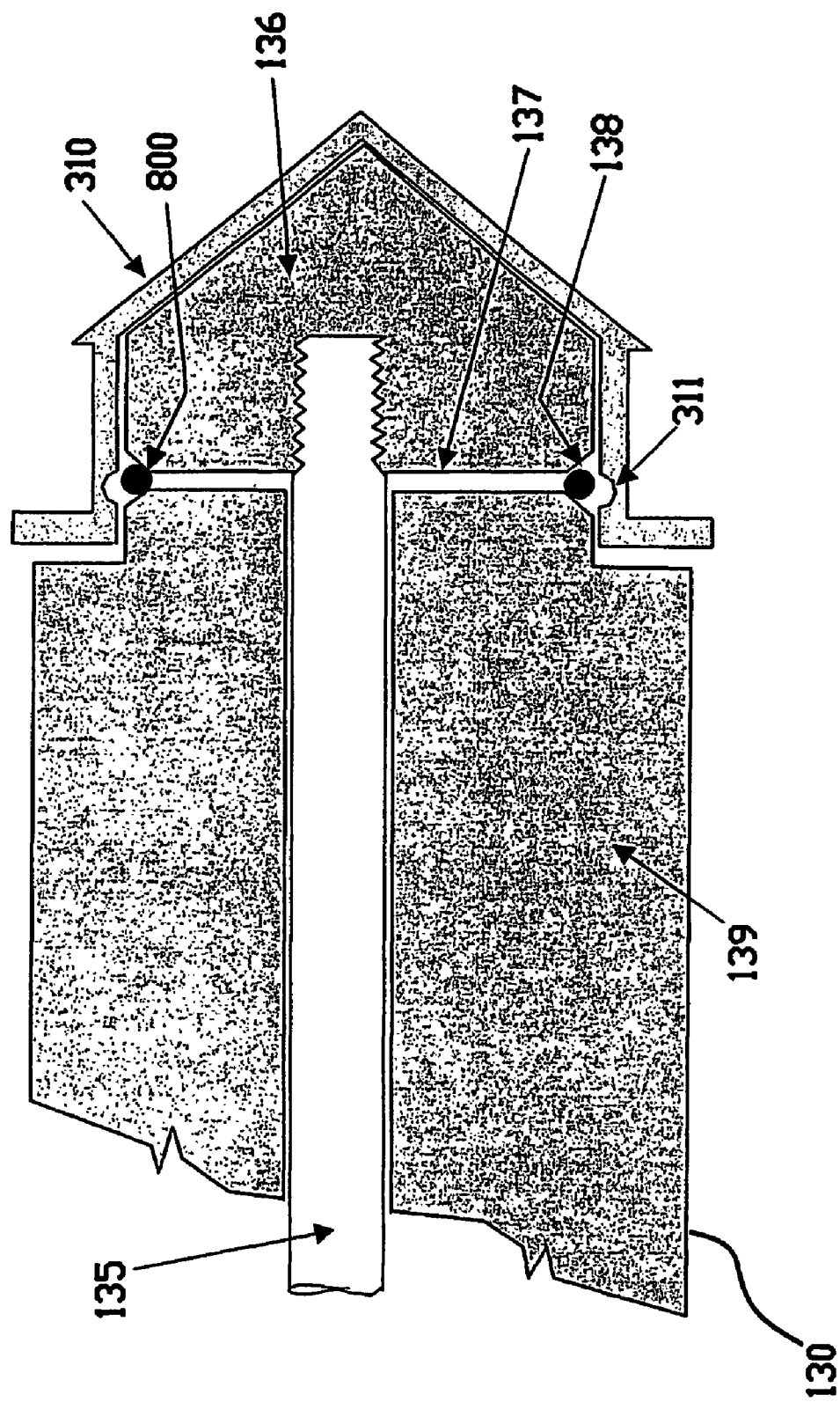
FIG. 17 shows yet another alternative example of the plunger/hub interlocking arrangement, having a ring actuated hub locking mechanism.

Such an arrangement is shown in FIG. 17, in which plunger 130 is divided into two sections—a main body portion 139 and a nose portion 136. Connecting these two portions is an actuating rod 135, a front end of which is embedded in nose portion 136. By pushing actuating rod 135 forward, nose portion 136 is caused to be longitudinally displaced by a small amount, forming gap 137 between main body portion 139 and nose portion 136. The radial ends of gap 137 are chamfered, creating void 138, the size of which is dependent on the size of gap 137. Within void 138, lies an expandable ring 800. This may be a rubber o-ring, a metal circlip, or any other suitable ring element. Ring 800 is biased towards its centre, such that it will tend to lie as deep as possible within void 138, and below the surface of plunger 130. This will be the position assumed when plunger 130 is moving forward along the syringe.

To retract hub 310, actuating rod 135 is moved backwards to cause gap 137 to close, in turn causing void 138 to become smaller. This in turn pushes ring 800 radially outwards, to protrude from plunger 130, and to be received in groove or recess 311, thereby retaining hub 310 to plunger 130.

It will be understood that groove or recess 311 need not in fact encompass the fill circumference of the inner surface of hub 310, but may take the form of individual recesses or depressions within the surface of hub 310 to receive individual pins from plunger 130. It will be understood that if rod 135 were the driving member of the injector, and plunger body 139 were restrained by a friction feeding system such as that described in FIGS. 39a and 39b, the hub retention function described above will operate automatically.

Figure 18A:
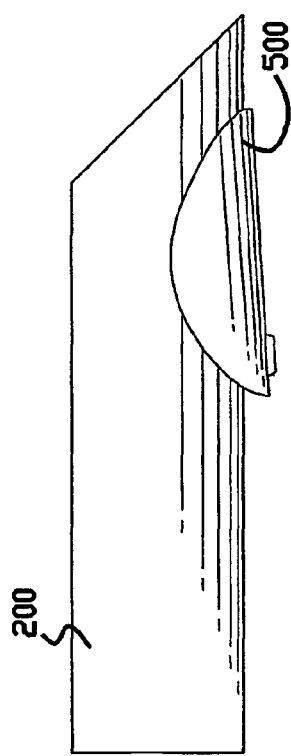
FIG. 18a shows a side view of the syringe holder with catch.
Figure 18B:
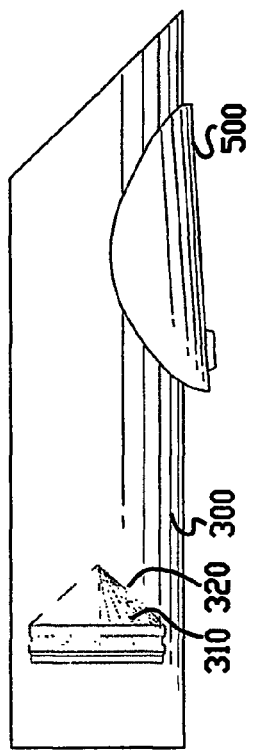
FIG. 18b shows the syringe holder and catch of FIG. 18a with the syringe and hub located in the syringe holder.
Figure 18C:
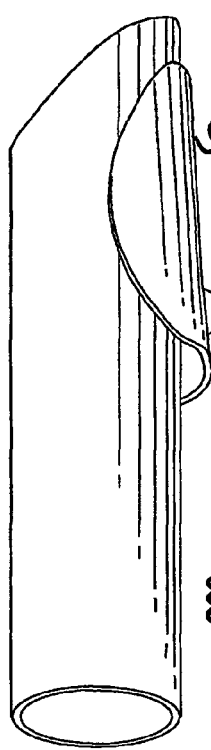
Figure 18D:
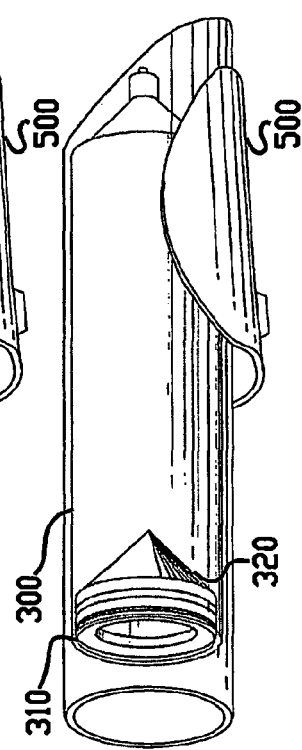
FIG. 18d shows a side oblique view of the syringe holder, catch and syringe of FIG. 18b.
Figure 18E:
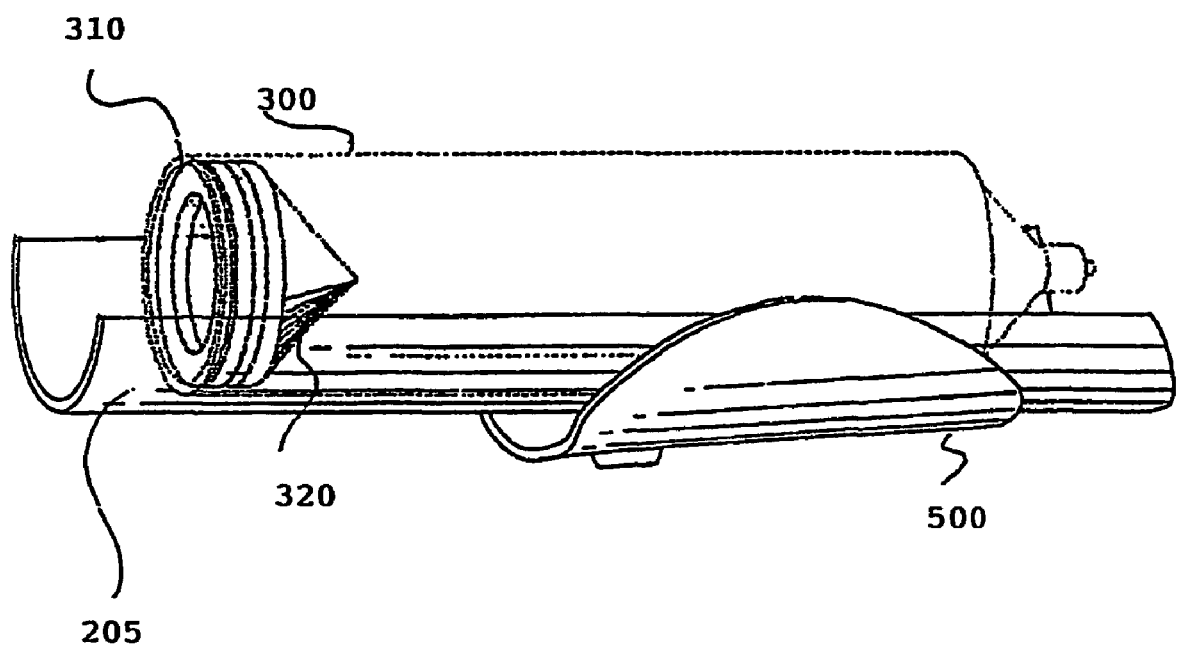
FIG. 18e shows a side oblique view of a syringe holder, catch and syringe according to the present invention.

The loading and retention of syringe barrel 300 inside injector unit 100 will now be described with reference to FIGS. 18a-e to 21. FIGS. 18a to 18d show various views of a syringe cradle member in the embodiment wherein the cradle member is a sleeve 200 and associated catch 500. FIG. 18e depicts the embodiment wherein the cradle member is a cradle 205 containing syringe barrel 300.

The left-most (rear) end of sleeve 200 (from the view of the depictions) is inserted into a receiving opening in the injection unit, while syringe barrel 300 is slipped rear first into sleeve 200 via the oblique opening appearing on the right hand side of sleeve 200 as seen from the figures. FIGS. 18b and d show various views of the embodiment wherein the cradle member is a sleeve 200 containing syringe barrel 300. Also visible are hub 310 and connected seal 320 which are positioned at the base end of syringe 300 as described previously. Catch 500 is pivotally connected to sleeve 200 as can be seen in FIGS. 19, 20 and 21. Syringe holder 200 is engaged in nose 10 of the injector (not shown). The connection between catch 500 and holder 200 is via catch hinges 510. Spring 540 biases one end of catch 500 away from the body of sleeve 200 such that syringe catch 520 is biased upwards and through sleeve aperture 530 as seen in FIG. 19. Upon insertion of syringe barrel 300 into sleeve 200, syringe catch 520 is displaced downwards by a downward force caused by the syringe sliding across the sloped top surface of syringe catch 520 (actuated by a human operator). Once syringe barrel 300 has been fully inserted into sleeve 200 (determined by syringe stop ring 210), spring catch 520 snaps back to assume its steady state position to engage a front portion 330 of syringe barrel 300, thereby retaining it within sleeve 200. This retention is strong enough to withstand the pressure experienced by the syringe upon actuation of the injector forcing plunger 130 into the barrel 300 to expel the contents of the syringe. In fact, the upright front edge 521 of catch 520 is angled so that it lies parallel to the front edge of sleeve aperture 530, which is itself similarly angled. This angle is chosen carefully to be greater than 90 degrees to the moment of force exerted by flange 330 on forward edge of aperture 530. In this way, the engagement forms a wedge or "dove-tail", which prevents catch 520 from being released when the syringe is forced forward by the plunger, thereby providing a highly secure retention means.

Furthermore, syringe sleeve 200 is close-fitting to the inserted syringe barrel 300. This helps to support the syringe against expansion under the high pressures caused in injectors, thereby enabling a thinner walled, lower cost syringe. Sleeve 200 is also preferably transparent, to allow an unobstructed view of the contents of the syringe (e.g., to determine is air is present in the syringe), which itself is transparent.

As discussed previously, this arrangement allows the syringe to be loaded into the injector unit in a single action by simply sliding it into a receiving sleeve from the front and without having to remove any part of the injecting unit. Further, the syringe and the hub need not be oriented in a particular manner. This saves a great deal of time and effort in syringe assembly and everyday use of the injector, and results in a simpler construction of the injector.

Figure 22A:
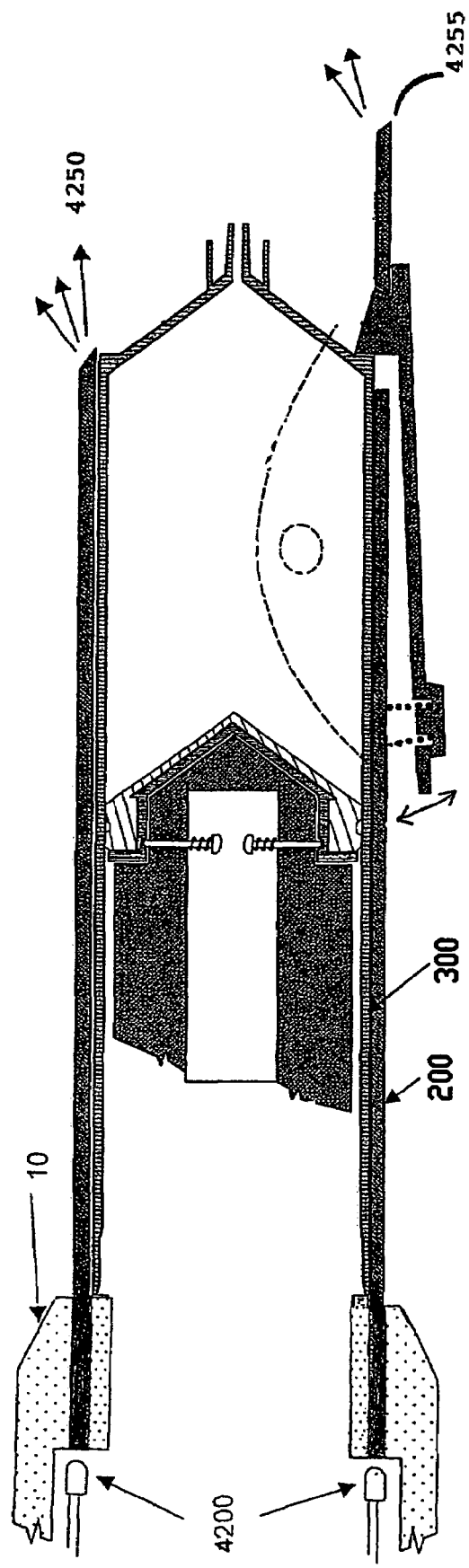
FIG. 22a shows a cross section side view of the syringe holder/syringe combination within the sleeve of the injector, with the syringe retained by a catch depicting the illumination member.

FIG. 22a demonstrates another preferred embodiment whereby there is an illumination member in the form of Light emitting diodes (LEDs) 4200 which are placed at the exposed rear (left-most) end of syringe sleeve 200 so that some of the light is received and transmitted along the walls of the sleeve. As with any thin, dense, transparent material, most of the received light is internally reflected longitudinally, as well as laterally, producing a diffused glow at the front end of the sleeve as depicted by arrows 4250. The beveled front end of the sleeve 4255 is preferably frosted (eg sanded) to achieve maximum diffusion, and is visible form a wide angle. Any suitable light source may be used, but they are preferably focused or reflected so that most of their output is projected towards the sleeve. Thus, in the embodiment depicted, they are LEDs.

The illumination sources may be various colours, and/or pulsed to provide many attractive effects, and may be used to remind the operator, for example, to remove the syringe.

It should be noted that the patient's blood may sometimes find its way into tube 400 and syringe 300 by virtue of the fact that, on occasion, while connected to the patient, the hub is retracted to draw blood back through tube 400 and into the syringe, for example to verify that the needle has properly entered the patient's vein. Since the syringe can be loaded from the front, tube 400 (as depicted in the FIG. 1 in relation to the prior art), may be permanently fixed to the syringe, and need not be connected and disconnected after use.

Figure 22B:
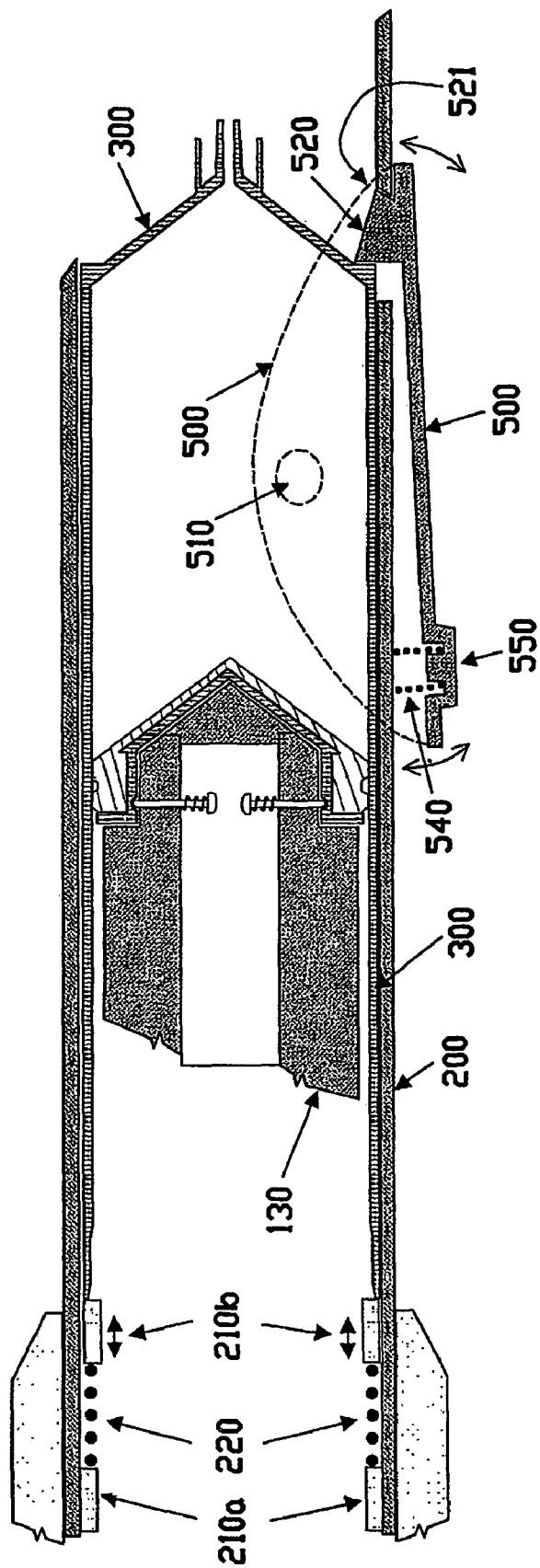
FIG. 22b shows the arrangement of FIG. 19 with a self-ejecting mechanism.

This reduces the risk of spilling contaminated blood. To further increase the efficiency of the system, syringe stop ring 210 may consist of 2 parts, separated by a spring element 220, as shown in FIG. 22b. The first part is a fixed part 210a which is essentially a portion of stop ring 210 in FIG. 18 and is fixed to syringe sleeve 200. The second part is a sliding ring 210b, which is able to slide over the inner surface of sleeve 200. Coil Spring element 220 biases sliding ring 210b away from fixed ring 210a and towards the front end of sleeve 200. When the syringe 300 is loaded into sleeve 200, its rear rim will engage slide ring 210b and force it towards fixed ring 210a, compressing spring element 220 there between, until spring catch 520 snaps back to retain syringe 300 as described above. In this state, syringe 300 is biased against catch 520 by the force of spring element 220 acting on sliding ring 210b. Accordingly, when syringe catch 520 is disengaged from syringe 300 (by pushing on syringe catch release button 550), syringe 300 is automatically partially ejected from sleeve 200 to facilitate removal thereof from the injector.

Some injector users prefer to manually fill syringes without the use of an injector. This ability is also of great benefit when users wish to pre-fill syringes, particularly when the injector is in constant use.

Figure 23A:
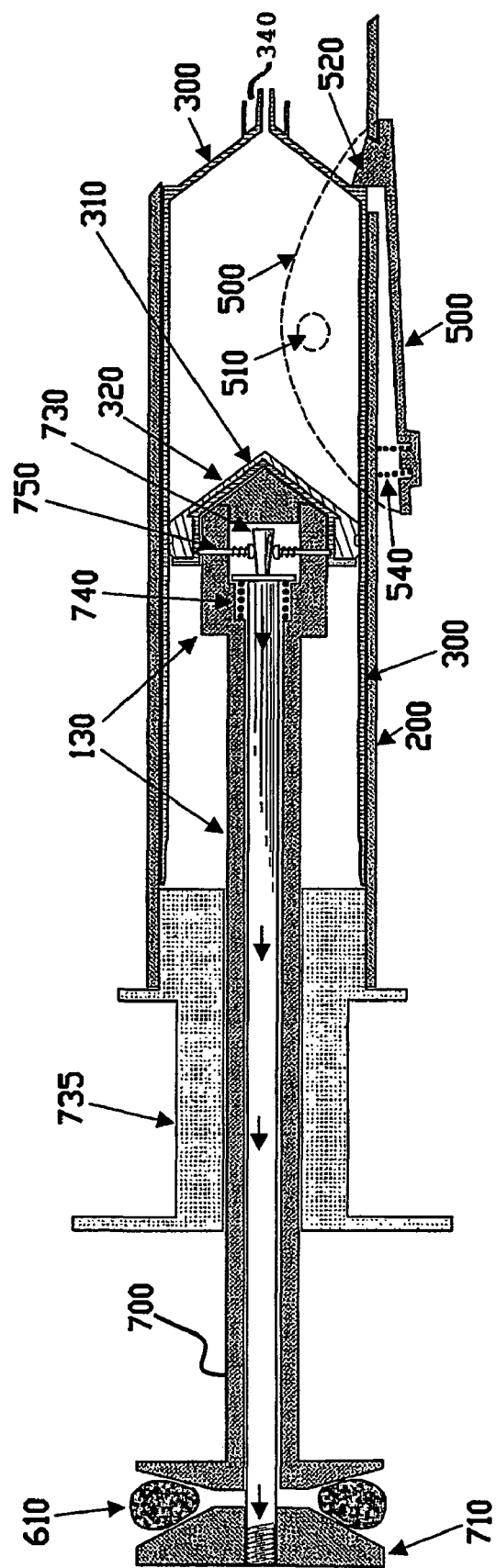
FIG. 23a shows a plunger adapted to be a syringe hand filler and associated holder.
Figure 23B:
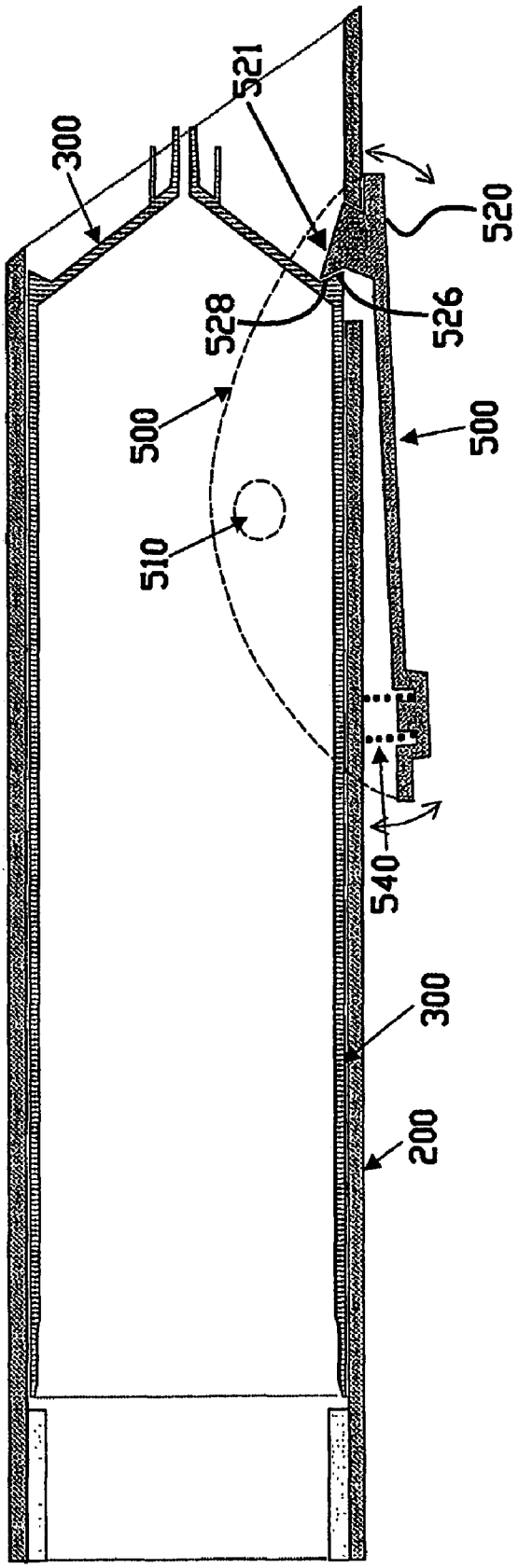
FIG. 23b shows a syringe and syringe holder comprising a concave syringe front flange and corresponding dovetail catch.

On the occasions where a syringe is desired to be manually filled, the present invention also provides for easy filling of the syringe. This is accomplished by way of a hand filler 700 as shown in FIG. 23a. This device is effectively a hand-held version of the plunger 130 described in detail above, and works in a similar manner. In use, the hub 310 and seal 320 could be located anywhere along the syringe. To fill the syringe, the hub/seal must be drawn back towards the rear of the syringe. To do this, hand plunger 700 is introduced into the syringe barrel 300, and pushed into the hollow of hub 310. In this position, pins 750 within the head of the hand filler do not protrude beyond the surface of the hand plunger 700. This is because cone element 730, inside the hand filler, is biased forward by spring elements 740, causing pins 750 to rest against the narrowest portion of cone element 730. Upon retraction by hand (with the fingers 610 of the operator engaging the handle 710 of the plunger), cone element 730 is pulled back with the head of hand plunger 700, forcing pins 750 outwards to be received in groove or recess 311, thereby engaging hub 310 and seal 320. Thus engaged, the hub and seal are drawn back through syringe 300 with the hand plunger 700, at the same time drawing in liquid through hole 340 and filling the syringe. When the hub 310 and seal 320 have reached the back of the syringe, hand plunger 700 is disengaged from hub 310 by reducing backward force on the plunger, allowing cone element 730 to move forward under the force of springs element 740, and allowing pins 750 to withdraw from recess or groove 311 as previously described. The filled syringe is then ready to be loaded into the injector 100 as described above. It should be noted that no part of the device can, at any stage touch the inner bore of the syringe, which could contaminate the sterility of the syringe. It should also be noted that the mechanism retaining the hub to the plunger can take many forms, including those described in FIGS. 7 to 17.

In another embodiment, the filled syringe may be left connected with the hand filler, and the combination may be connected at the neck 735 to the front end of a suitably modified injector. In this application, the hand filler becomes a syringe holder and pressure sleeve. The complete hand filler device is used to firstly fill the syringe, then the filler device (with syringe) is placed into the injector. The injector pushes on the rear end 710 to expel fluid from the syringe.

Where the hand filler device illustrated is provided only for filling (in association with an injector made for injecting the syringe), then as long as all syringes are fully expelled (as is the convention), then if the length of the plunger 700 were shortened by only a few millimetres, it could not fill a used (fully expelled) syringe because it can not reach the hub.

In a further embodiment, the contents of syringe 300 can be expelled by hand force on plunger knob 710 (i.e., an injector syringe such as 300 could be used as a more conventional hand-held syringe).

As with most injector syringes, syringes as used in the present invention are preferably supplied with the hub/seal in the fully retracted position.

The various mechanisms for retaining the hub to the plunger of the present invention are preferably arranged such that they can be actuated whilst the plunger is in the fully retracted position, and thereby preferably engage, retain, and fill a new syringe. However, the invention contemplates that the plunger can be arranged to engage the hub at any suitable location within the syringe.

Following use, the hub and seal of a used (or partially used) syringe will typically be left somewhere forward of the fully retracted position, and, hence the devices of the present invention usually do not engage, retain, fill or operate a used syringe, thereby eliminating, or drastically reducing, instances of cross-patient contamination. However, the invention broadly contemplates arrangements wherein the hub can be left at any position within the syringe.

Figure 23F:
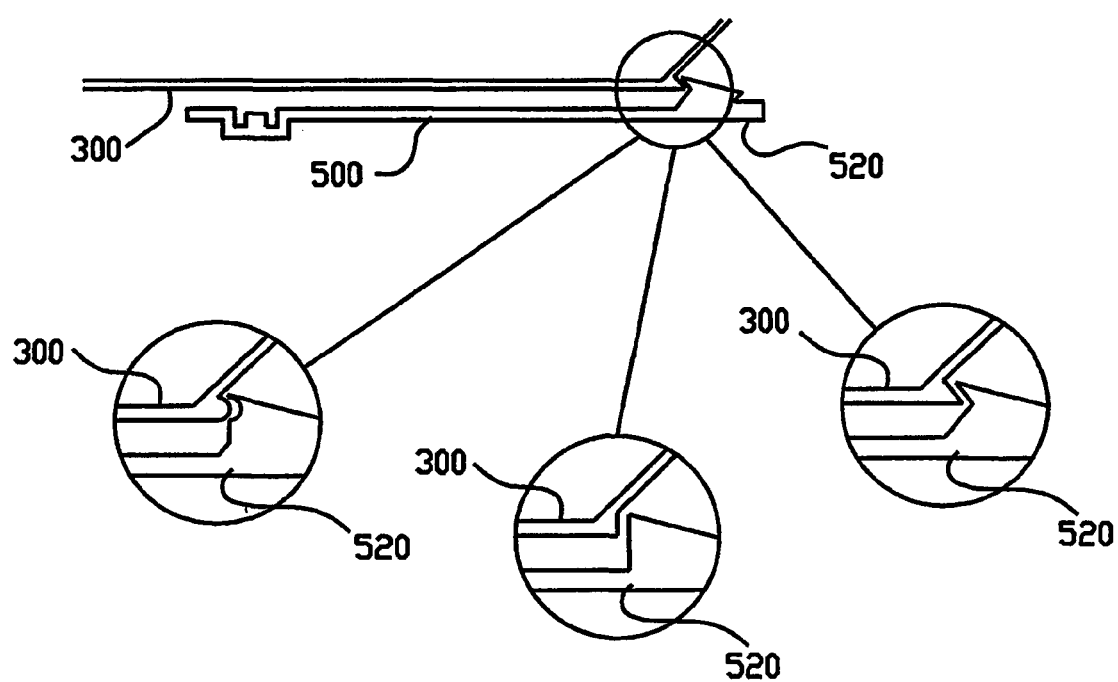
FIG. 23f demonstrates in cross-section, various alternative arrangements of catches according to the present invention.

It will readily be appreciated that there are a number of possible designs for the catch for retaining the syringe within the cradle member/sleeve. FIGS. 23b to 23e illustrate a syringe 300 and syringe holder 200, catch 500 and catch member 520. The inner edge 526 of the catch 520 is of complementary shape to a concave front flange on the syringe 300. FIG. 23f shows three embodiments of the interface between the inner edge of the catch 520 and the front of the syringe 300.

Figure 24:
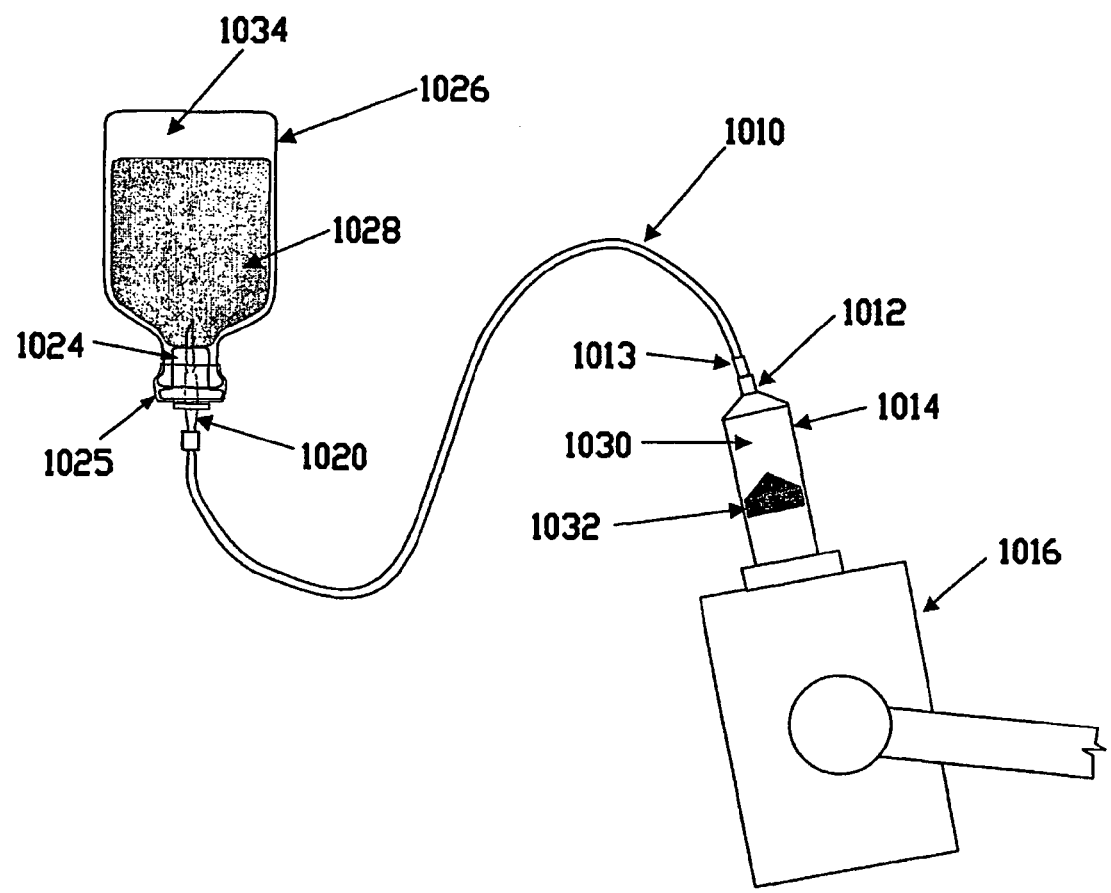
FIG. 24 shows the connection and orientation of certain key elements in the system, as oriented during the filling sequence.
Figure 25:
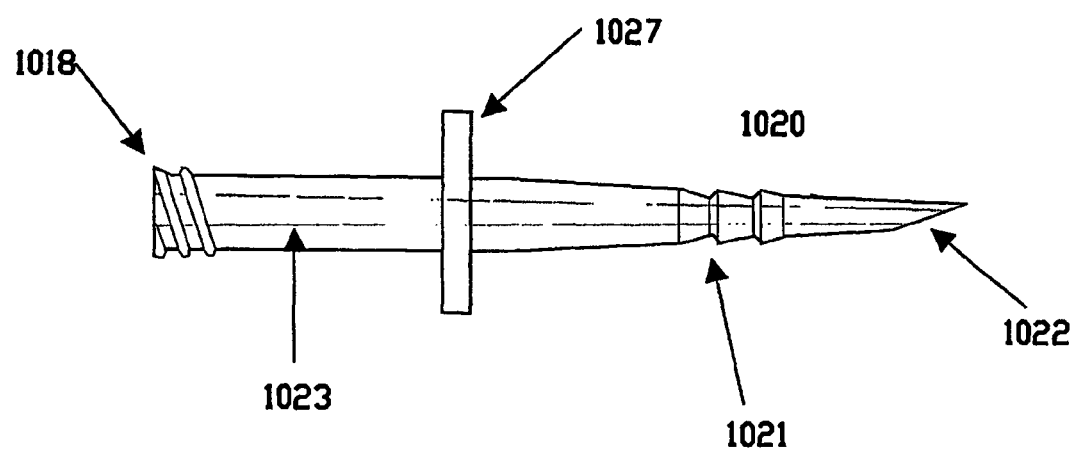
FIG. 25 shows an example of a Barbed Spike for tapping the bung of a medical fluid bottle.

The preferred embodiment of an additional embodiment of the invention comprises the essential elements illustrated and oriented as shown in FIG. 24. An extension tube 1010 is firstly fitted to the tip 1012 of an injector syringe 1014. The syringe 1014 is then fitted to an injector (or syringe pump) 1016. The system operator (not shown) then programs the desired patient injection volume on the injector control panel (not shown), and then the operator tilts the combined injector 16 and syringe 1014 unit upwards as illustrated in FIG. 24, at which point a position or angle sensing tilt switch in the injector preferably causes the piston 1032 of the syringe 1014 to advance automatically by the injector to the desired volume. It will be appreciated by those familiar with the art that such programming and automatic control of the injector is quite known, although not in response to the tilting operation, or means of triggering. Of course, the operator could also initiate some or all of these actions. As the combined injector 1016 and syringe 1014 unit is tilted upwards, any subsequent fluid 1028 from bottle 1026 will fall to the bottom of syringe 1014, and air 1030 in the syringe 1014 will rise to the syringe tip 1012, and be expelled through tube 1010 when the piston is advanced. The free end of tube 1010 is then connected to the socket end 1018 of a special non-vented spike 1020 which is shown in FIG. 24, and in more detail in FIG. 25. The sharp end 1022 of spike 1020 is then driven into the soft rubber bung 1024 of the fluid bottle 1026. The sharp tip 1022 of spike 1020 pierces the bung 1024 of the bottle 1026, creating a path from the bottle contents 1028 through the spike 1020 and tube 1010 to the syringe. It should be noted that at this point the system is sealed from outside air, and pressure in the system will be neutral. It should also be noted that spike 1020 has a barbed neck 1021 as shown in FIG. 25 to ensure it will not be forced out of the bung 1024 when the system is later pressurised. The bottle 1026 is then mounted or hung inverted (as illustrated in FIG. 24) so that fluid 1028 can be drawn out through the spike 1020 and tube 1010 etc.

The "FILL" button (not shown) is now selected on the injector 1016 by the operator, and preferably performs the following sequence automatically:

The syringe piston 1032 is driven fully forward to the tip 1012 of the syringe 1014, compressing the air 1030 in the syringe, tube, and bottle. Much of the sterile air 1030 in the syringe and tube 1010 will be driven into the bottle 1026, and rise to the air space 1034 in bottle 1026. It will be appreciated by those familiar with the art that such air 1030 will be sterile as long as the syringe 1012 was manufactured and sterilised with the hub 1032 fully retracted (i.e. filled with air) as illustrated in FIG. 2b. Without delay, the piston 1032 is then automatically retracted to slightly over (eg 130%) the programmed volume, and fluid 1028 is transferred quickly from the bottle 1026 via spike 1020 and tube 1010 into the syringe 1014, aided by both air pressure 1034 in the bottle 1026, plus a partial vacuum in the syringe due to retraction of piston 1032. Following a short delay to allow the pressure to equalise and fluid to fully transfer, the syringe 1014 is filled to more than the programmed fluid volume, plus some residual air. The piston 1014 is then immediately and automatically advanced back to the desired programmed volume, purging any residual air and surplus fluid back to the bottle 1026, leaving the syringe 1014 entirely filled with the programmed volume of fluid, with no air in either the syringe 1014, or tube 1010.

At this stage the "FILL" sequence is complete, and it is important to note that the system has neutral pressure (because the piston has been returned back to the position at which the system was sealed) so that when the tube is disconnected from the bottle (or the spike is removed), the system neither sucks air, nor drips fluid.

The bottle 1026 is now righted, and the tube 1010 is disconnected or detached from the spike connector 1018, and may now be connected to the patient, ready for injection.

It will be appreciated by those familiar with the art that the following facts and arrangements are normal procedure in this field, and may not be well illustrated or described in this document, however are important to the implementation and operation of the invention:

- Components used in the fluid path, and air contained within each is sterilised during manufacture.
- There is usually a small void of air or gas in bottles of medical fluid.
- Before tapping, the protective cap over the bung centre is removed (to allow access to for the spike), however the bung retainer 1025 (shown in FIG. 24) is left on the bottle (otherwise the bung may be dislodged by air pressure during filling).
- Injector syringes are typically supplied fitted with the plunger retracted (i.e. it is filled with sterile air)
- The syringe, tube, and spike would have standard luer locking connectors to ensure they are secure and sealed under pressure.

Figure 28:
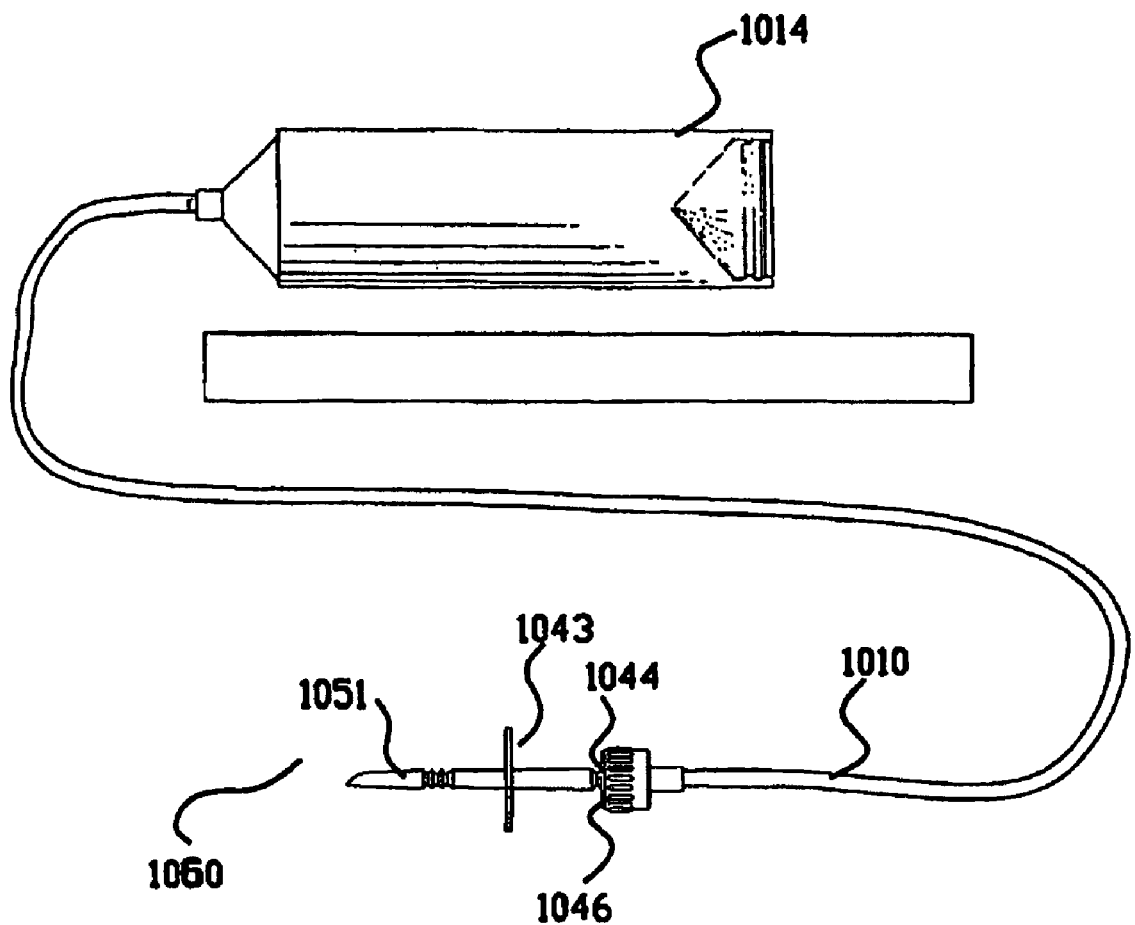
FIG. 28 shows a combination Luer Connector with frangible spike, permanently bonded to the associated Extension Tube and Syringe to form a non re-usable set for injecting patients.

The following variations to the system could enhance the invention under some circumstances:

- The Fill sequence program could be extended with an additional forward-retract cycle—particularly for volumes approaching the maximum capacity of the syringe. This is to ensure that all air has been expelled. When a syringe is to be filled to near capacity (>75%) there is insufficient travel on the piston to retract 130%. Hence additional strokes are required to expel all the air. This "130%" figure is a function of the volume of (air) the tube, and air space in the bottle—a greater tube volume (or less air space in the bottle) requires more over travel.
- During the fill sequence, the first compression stroke of the piston would preferably expel all the air from the syringe—particularly for x-ray contrast, where the bottles normally have a significant air space.
- Alternatively, to optimise performance even with bottles having relatively small air space, during the compression the injector could sense the pressure in the system (for example by sensing the load on the drive means) and retract prematurely if the pressure approached unsafe levels.
- The controlling electronics and associated displays and audible enunciators could prompt the operator as to what step or otherwise to take next in the filling routine.
- The injector tilt switches (or sensors) could be used to trigger or inhibit other functions of the injector, for example inhibit injection until the injector and syringe are oriented downward, or enable higher flow rates during fill (rates that would be unsafe for injecting into patients).
- The syringe 1014 could be supplied with the extension tube 1010 and spike 1014 already assembled (as shown in FIG. 24) during manufacture, further reducing operator time.
- The Syringe 1014 and Tube 1010 could be manufactured with the tube 1010 permanently attached and bonded directly to the syringe tip 1012, protecting the sterility of the syringe tip 1012, and reducing manufacturing & material costs by dispensing with connector 1013, which is normally used to adapt the tubing 1010 to the syringe tip 1012 (as illustrated in FIGS. 31 to 33, and described below). As well, safety is improved by ensuring the tube cannot be disconnected, possibly releasing contaminated fluids.
- An air detector (optical, ultrasonic, etc) could be fitted to the tubing, ensuring there is no air present after filling, and disallowing operation of the injector until the air is removed.
- The syringe 1014 and associated extension tube 1010 could be permanently bonded 1039 to a special combination patient connector with frangible spike (as shown in FIG. 27c.), and all supplied as one set 1060. This set could provide a reduced cost, as well as a non-reusable system which could prevent patient to patient cross-infection. This concept is described in detail as follows:

The complete set 1060 (as shown in FIG. 28) is used to fill the syringe much as described previously, however after filling is complete, instead of disconnecting the spike from the tube, spike 60 is then snapped off, and as before, leaves a male luer connector on the end of the tube for connection to the patient. Importantly however, with the spike removed the syringe is less likely to be inadvertently re-filled, and hence cannot be used with more than one patient, thus preventing cross-infection from one patient to the next.

It is understood that a conventional spike can still be attached after the frangible spike is removed and therefore used to re-fill, and possibly cause contamination. This could be overcome by adopting a non-standard connector (eg larger diameter Luer). This would require a non-standard mating connector on the needle. Also, if the contents of a bottle are used to fill more than one syringe (as is often the case) the bottle cannot be inadvertently contaminated by re-filling a used syringe.

FIGS. 26 and 27 show various examples 1040 and 1050 of combination male luer connector with frangible spikes and tube 1010. FIG. 28 shows the complete set 1060 having an extension tube 1010 bonded at each end to the syringe 1014 and frangible connector/spike 1050.

Figure 26A:
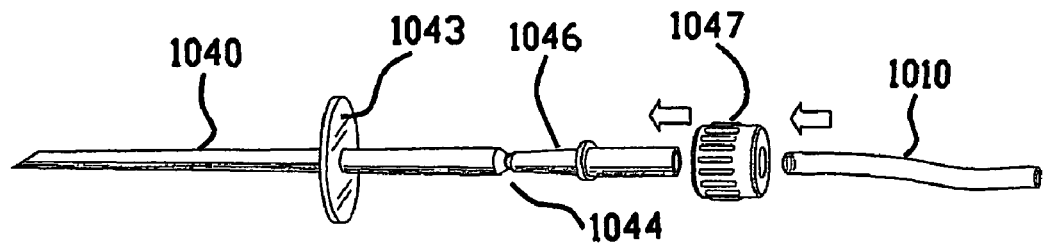
FIG. 26a is an oblique view of combination Luer connector with frangible spike, locking collar, and tube, before assembly.
Figure 26B:
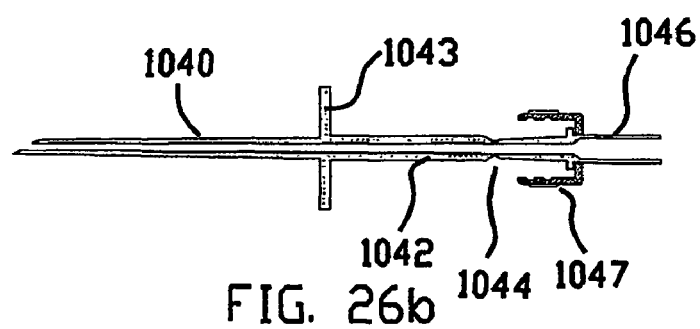
FIG. 26b is a longitudinal axial cross-section view of combination Luer connector with frangible spike, and locking collar, after assembly.

The alternative combination connector/spikes are illustrated and described as follows:

FIGS. 26a to 26d show various views of an example of a combination 1040 of male Luer connector 1046 with frangible spike 1042, and locking collar 1047. FIG. 26a is an oblique view of combination Luer connector 1046 with frangible spike 1042 and locking collar 1047 before assembly. Disc 1043 simply provides a grip for holding the spike. The frangible neck 1044 is seen clearly in FIG. 26b, which is a longitudinal axial cross-section view of a combination Luer connector 46 with frangible spike 1042 and locking collar 1047, after assembly. The locking collar has a conventional female luer locking thread for retaining the patient needle, which is connected after the spike is detached. Small raised nodules or barbs 1048 serve as detents to discourage the collar from sliding off the connector once assembled. The locking collar 1047 is not essential to the invention, however is advisable when used with pressure injectors.

Figure 26C:
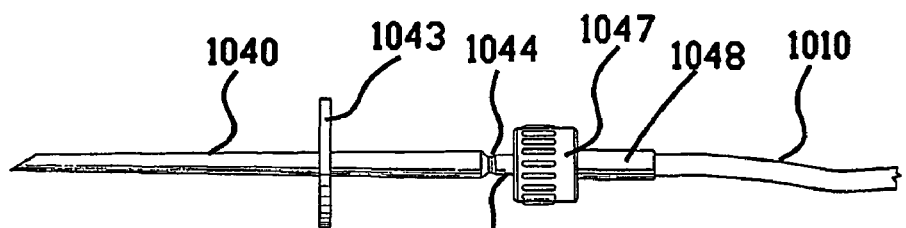
FIG. 26c shows a combination Luer connector with frangible spike, locking collar, and tube, after assembly and bonding.

FIG. 26c shows a side view of the combination connector/spike/collar 1040, after assembly and bonding to the tube 1010.

Figure 26D:
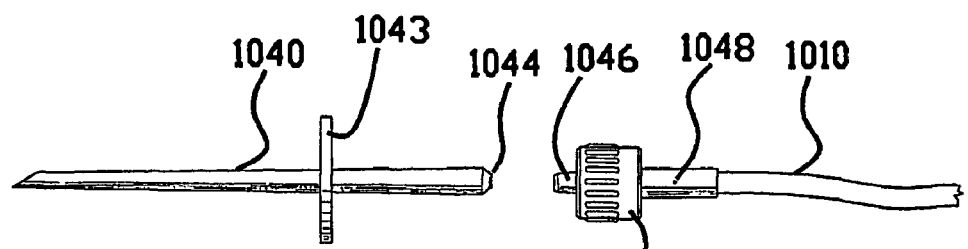
FIG. 26d is a combination Luer connector with frangible spike and locking collar, shown after the spike has been "snapped off" at the frangible neck.

FIG. 26d shows a combination connector/spike/collar 1040 after the spike has been detached at the frangible neck 1044, leaving a standard male luer lock connector 1046 on the end of the tube 1010.

Figure 27A:
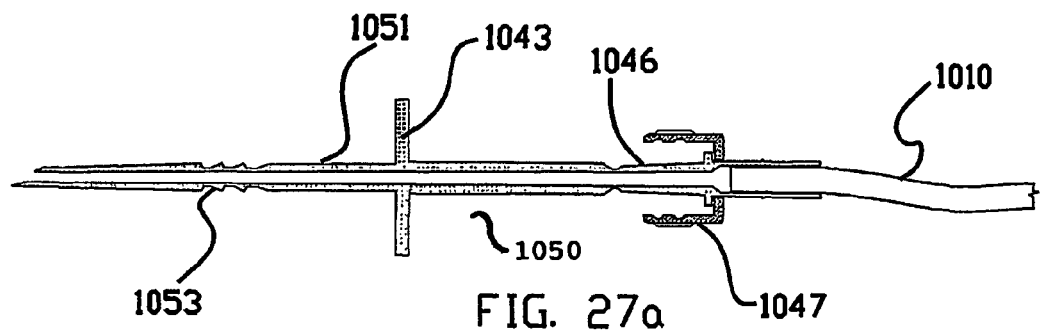
FIG. 27a shows a longitudinal axial cross-section view of a Luer Connector with barbed frangible spike, locking collar, and bonded tube.
Figure 27B:
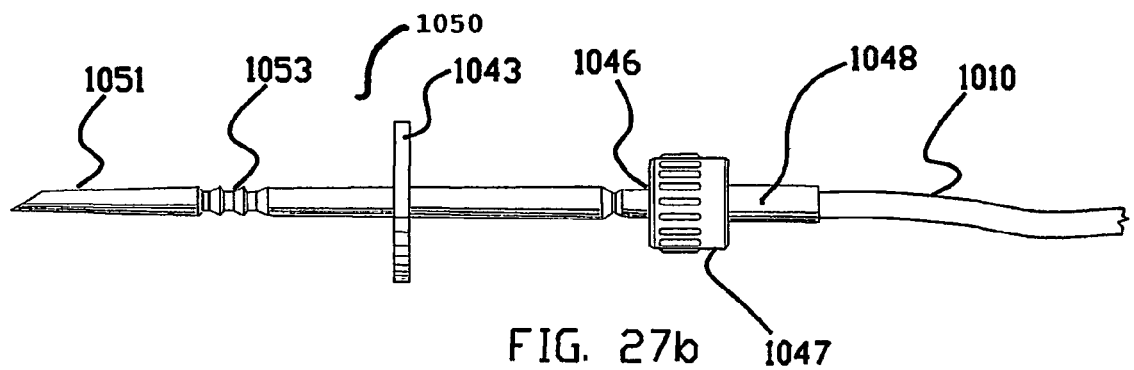
FIG. 27b shows an example of a Luer Connector with barbed frangible spike and locking collar, after assembly and bonding.
Figure 27C:
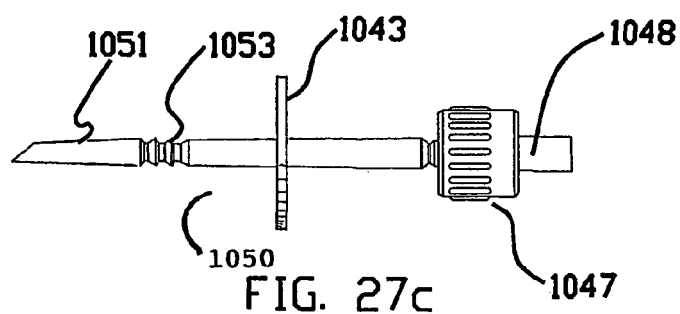
FIG. 27c shows a shorter example of a Luer Connector with barbed frangible spike, locking collar, and bonded tube.

FIGS. 27a to 27c show various views of an alternate example of a combination 1050 of male Luer connector 1046 with barbed frangible spike 1051, and locking collar 1047. The barbs 1053 are useful in discouraging the spike from being dislodged from the bung 1025 of the bottle 1026 during the pressurization phase of filling.

FIG. 27a shows a longitudinal axial cross-section view of combination 1050 connector/barbed frangible spike/collar.

FIG. 27b shows combination 1050 connector/barbed frangible spike/collar, after assembly and bonding to the tube 1010.

FIG. 27c shows a shorter example of combination 1050 connector/barbed frangible spike/collar. It will be appreciated by those familiar with the art that the spike may well be significantly shorter (in proportion) depending on the size of the bottle and bung.

FIG. 28 shows an example of combination 1060 connector/barbed frangible spike/collar permanently bonded to the associated Extension Tube 1010 and Syringe 1014, to form a non re-usable set 1060 for injecting patients.

The complete set 1060 is used as follows: Firstly the spike 1051 is inserted into the bung (not shown in FIG. 28), and the syringe 1014 is filled as previously described. After the spike 1051 is withdrawn from the bung, the spike end 1051 is "snapped off" at the frangible neck 1044 and discarded, leaving the conventional male luer lock tip 1046 for connection to the patient (not shown). It should be noted that the patient (not shown) cannot possibly be connected to the set 1041 until the spike 1051 is detached. Once separated however, the spike 1051 cannot ordinarily be reconnected, and hence associated tube 1010 and syringe 1014 cannot be re-filled, thus ensuring only one patient can be injected per set—ie this prevents any chance of inadvertent cross infection from one patient to the next.

It would be appreciated by those familiar with the art that a vented spike could also be combined frangibly with a male luer connector, however the syringe would be filled in a more conventional manner.

It should be noted that all cross-section views in FIGS. 29 to 33 are longitudinal, through the axis of the parts.

Figure 29A:
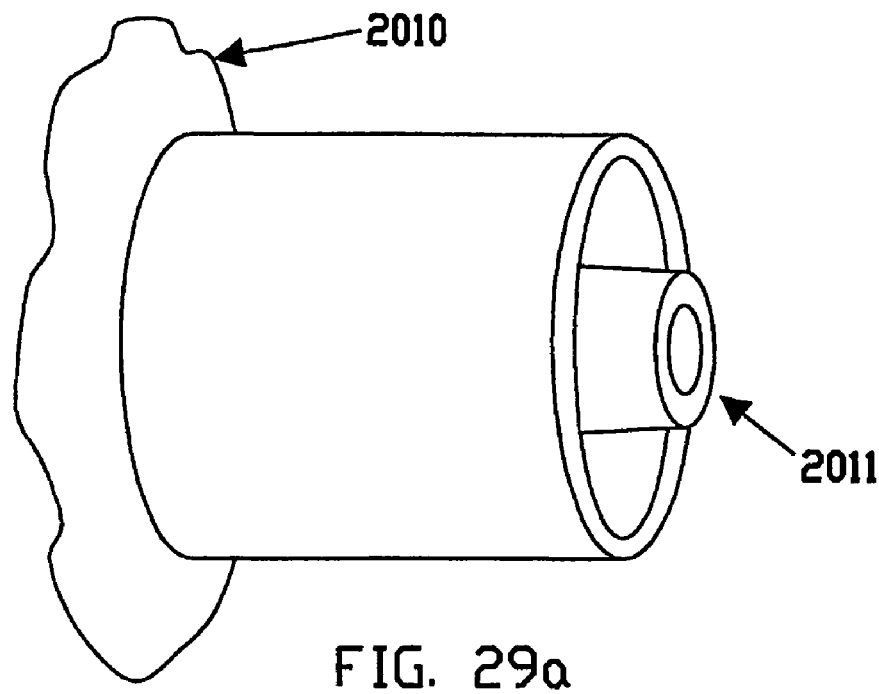
FIG. 29a shows an outer overall view of the luer lock of FIG. 30.
Figure 29B:
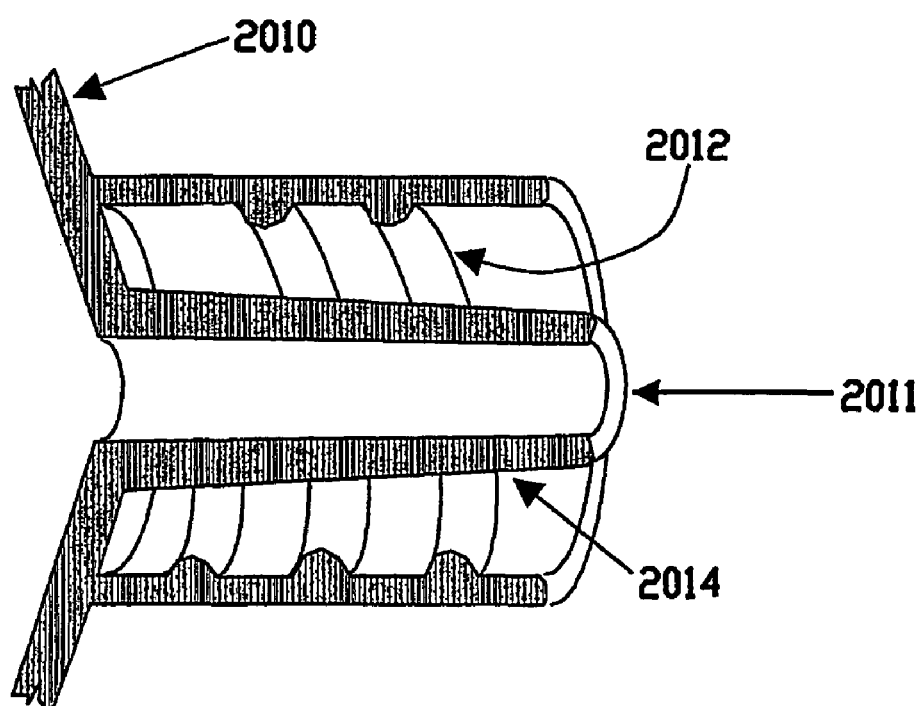
FIG. 29b Figure shows a longitudinal axial cross-sectional view of a typical syringe luer lock connector.

As required above and elsewhere in medicine, it is often desirable to connect or bond a flexible plastic tube directly to a rigid plastic spout or luer outlet. A typical male Luer Lock connection is illustrated in FIG. 29, before connection. FIG. 29a shows an overall view, and FIG. 29b shows a longitudinal axial cross-section view. The syringe body 2010 has an outlet connector tip 2011 which has a tapered male luer outer surface 2014, surrounded by a female locking thread 2012 of larger diameter, on the same axis but slightly forward of the thread. It should be noted that almost all luer tapers 2014 are made to a standard diameter, with a taper of approximately 6% as defined in International Standard IS0594. The outer luer taper 2014 is clearly evident in cross-section FIG. 29b. Syringes 2010 (including tip 2011 and thread 2012) are normally injection moulded from tough semi-rigid transparent polypropylene.

Figure 30:
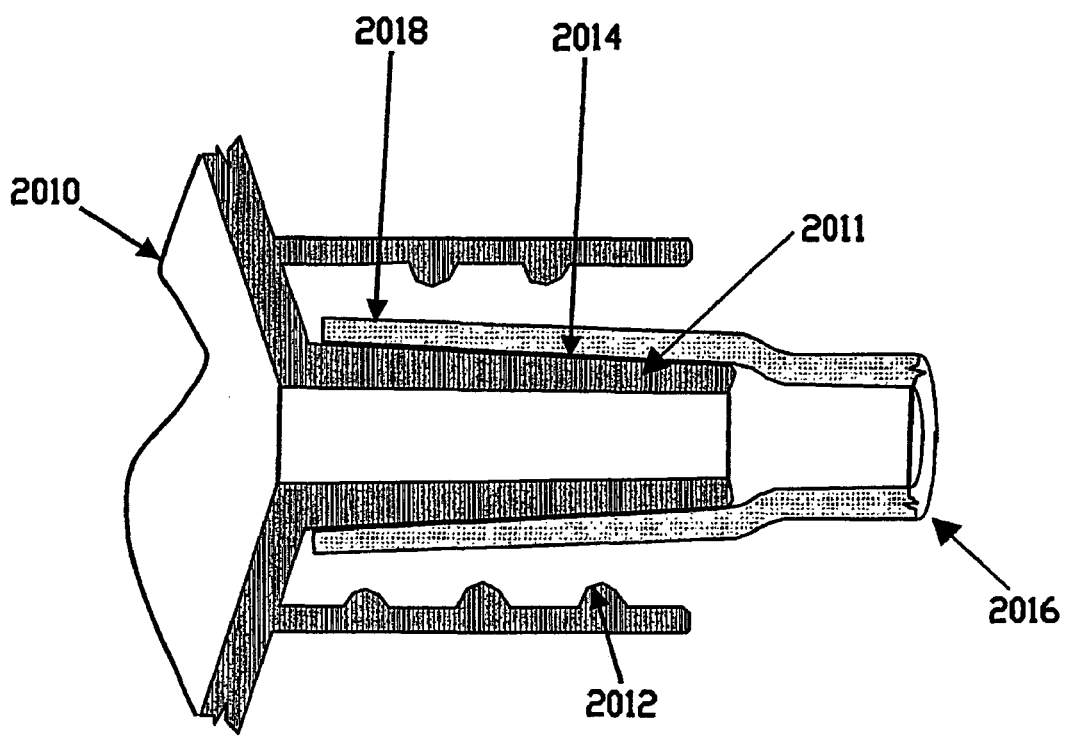
FIG. 30 illustrates a longitudinal axial cross-sectional view of an ordinary soft plastic tube pushed over the tip of a typical luer.

FIG. 30 illustrates a soft plastic tube 2016 pushed fully over the syringe tip 2011. The tip 2011 has a tapered outer 2014, and the tubing 2016 stretches and conforms to the taper 2014, and the resultant outer surface 2018 of the tubing forms an enlarged taper.

In FIG. 31 the basic form of clamp invention is shown before and after fitting.

The clamp 2020 is formed in a cylindrical shape with a hollow inner tapered diameter 2021 from semi rigid plastic, with a small chamfer 2022 on the leading edge to assist assembly.

The clamp 2020 is installed by simply pushing over the tapered outer surface 2018 of the tube, and inside the female thread 2012 of the syringe connection. It will be understood by those familiar with the art that the clamp 2020 has suitably precise dimensions for a firm interference fit on both its inner and outer diameters, as illustrated, to suit the wall thickness and compliance of both the tubing and the syringe.

When force fitted, the inner taper 2021 of clamp 2020 firmly squeezes the tubing 2016 onto the tip 2011 of the syringe 2010, as shown in FIG. 31. The syringe tip 2011 is also made from semi-rigid plastic, and all components deform slightly to exert even pressure on the luer tip/tube connection, ensuring it is sealed very effectively.

Alternate variations to the basic clamp design are illustrated in FIGS. 32 to 35.

In FIG. 32 small barbed annular rings 2032 have been added to the outer surface of the barbed clamp 2030 to improve retention inside the female locking thread of the connector. The clamp 2030 is pressed over the tube 2016 and into the syringe 2010 as above, and the barbs 2032 interfere with and grip the female thread 2012 ensuring it cannot be dislodged. As above, inner taper 2021 of clamp 2030 firmly squeezes the tubing 2016 onto the tip 2011 of the syringe 2010. This type of clamp would suit permanent and tamper-proof applications because the clamp would be almost impossible to remove without the use of tools.

In FIG. 33, male threads 2042 have been added to the outer surface of two similar styles of clamp 2040 and 2050, which mate with the female thread 2012 of the syringe 2010, and have a tapered inner surface 2021. The purpose of thread 2042 is to assist assembly, as well as firmly clamp the tube 2016 onto luer taper 2014. During assembly the clamps 2040 or 2050 are simultaneously pushed and screwed inside the syringe thread 2012 and over the tube 2016, squeezing the tube 2016 onto the luer taper 2014, resulting in a more secure, tighter fitting connection than those described above. As above, inner taper 2021 of clamps 2040 and 2050 firmly squeezes the tubing 2016 onto the tip 2011 of the syringe 2010.

Figure 33A:
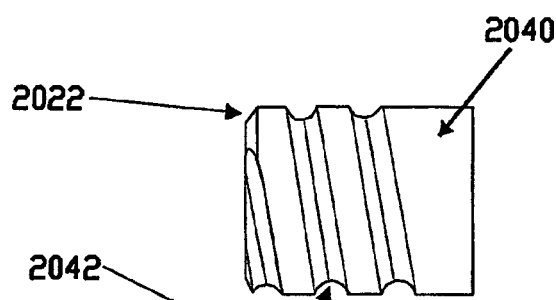
FIG. 33a depicts a plain clamp with male threads.
Figure 33B:
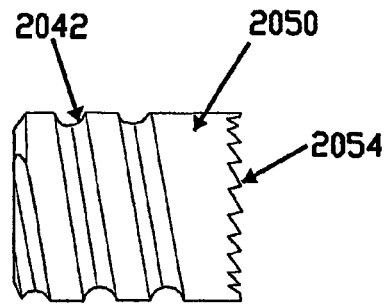
FIG. 33b depicts a plain clamp having male outer threads, with the addition of serrated grip to the rear end of the clamp.

FIG. 33b has additional barbed serrations 2054 to the rear end of the clamp, which assist in gripping and twisting the clamp during assembly.

It will be understood by those familiar with the art that the rear end or flange may take many forms to suit hand, machine, or tooled assembly, and/or to discourage disassembly.

Figure 33D:
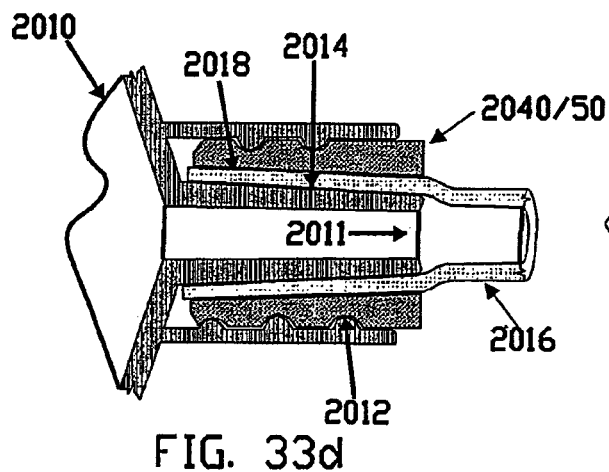
FIG. 33d depicts a longitudinal axial cross-sectional view of a clamp having male outer threads, screwed into the female locking thread of a luer locking syringe, and clamping a tube onto the associated male luer tip.
Figure 33C:
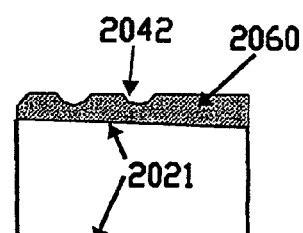
FIG. 33c depicts a longitudinal axial cross-sectional view of a plain clamp having male outer threads added to the outer surface.

FIG. 33c shows a longitudinal cross-section of either clamp 2040 or 2050, showing male threads 2042, and internal taper 2021 to mate with outer taper 2018 of tube 2016.

Figure 33F:
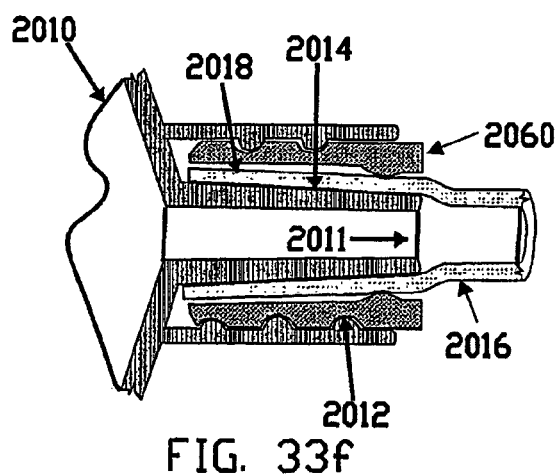
FIG. 33f depicts a longitudinal axial cross-sectional view of a clamp having male outer threads plus an annular internal ridge, screwed into the female locking thread of a luer locking syringe, and clamping a tube onto the associated male luer tip.
Figure 33E:
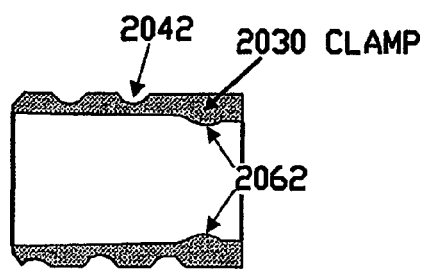
FIG. 33e depicts a longitudinal axial cross-sectional view of a clamp having male outer threads, with the addition of an annular ridge added to the inside surface of the clamp.

FIG. 33d shows a longitudinal cross-section of either clamp 2040 or 2050,

FIG. 33e shows a longitudinal cross-section of clamp 2060, showing male threads 2042, plus an internal annular ridge 2062 added to the inside surface of the ridged clamp 2060.

FIG. 33f shows clamp 2060 after being simultaneously pushed and screwed inside the syringe thread 2012 and over the tube 2016, squeezing the tube 2016 onto the luer taper 2014. The internal ridge 2062 of clamp 2060 concentrates the squeezing action to a short area 2064 [not seen in FIG. 33f] of the union with the tube 2016, providing a more concentrated pressure and improved sealing compared with those described above.

Alternately, it could be argued by those familiar with the art that clamp 2060 provides an equivalent seal to those above, with less assembly (and disassembly) force.

It will be understood by those familiar with the art that one or more annular rings may be included on the inner surface of any of the above clamp styles, and that the profile of the ridge may be varied to suit the hardness of the particular tubing employed (not illustrated).

Figures 34A, 34B:
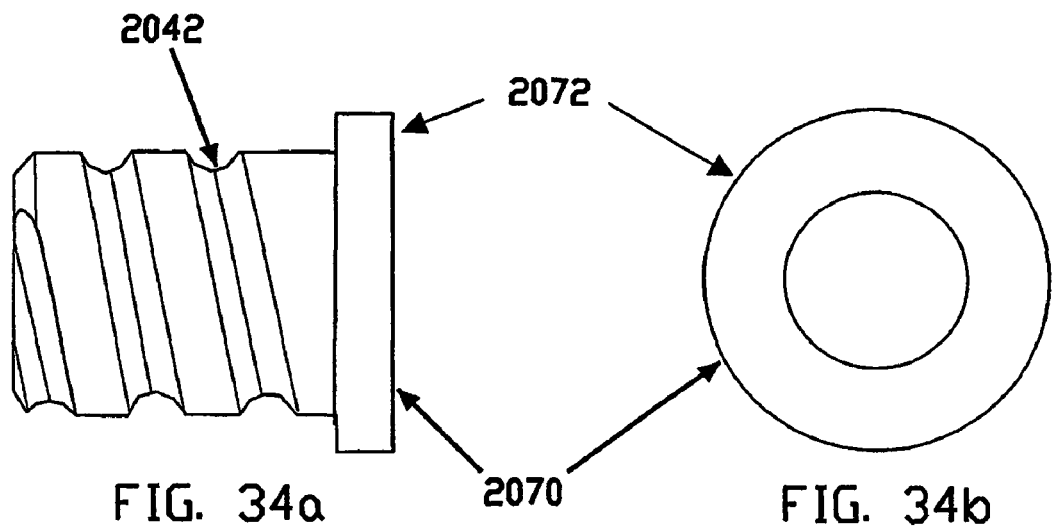
FIG. 34a illustrates a side view of a Threaded Clamp with a plain flange added to the rear end of the clamp.
FIG. 34b illustrates a rear view of a Threaded Clamp with a plain flange added to the rear end of the clamp.

FIGS. 34 and 35 illustrate various flanges 2072 and 2082 (respectively) added to the rear end of the threaded clamp style 2040 previously-shown in FIG. 33a. Both clamps 2070 and 2080 have male threads 2042 on their outer surface to mate with syringe female thread 2012, for the purpose of assisting assembly and firmly clamping the tube 2016. FIG. 35 has additional barbed teeth 2082 on the outer perimeter of the flange 2083 which assist clockwise tightening 2084 of the clamp 2080, but hinder anti-clockwise unscrewing, thereby making the connection virtually tamperproof. Both clamps 2070 and 2080 are inserted into the syringe (and clamp the tube) in the same manner as those described above, and may or may not have annular rings on their inner surface.

If a removable clamp is required, clamp 2070 in FIG. 34 would be preferred. Alternatively the flange of clamp 2070 could have non-directional serrations added to assist grip in either direction (not illustrated).

Figures 35A, 35B:
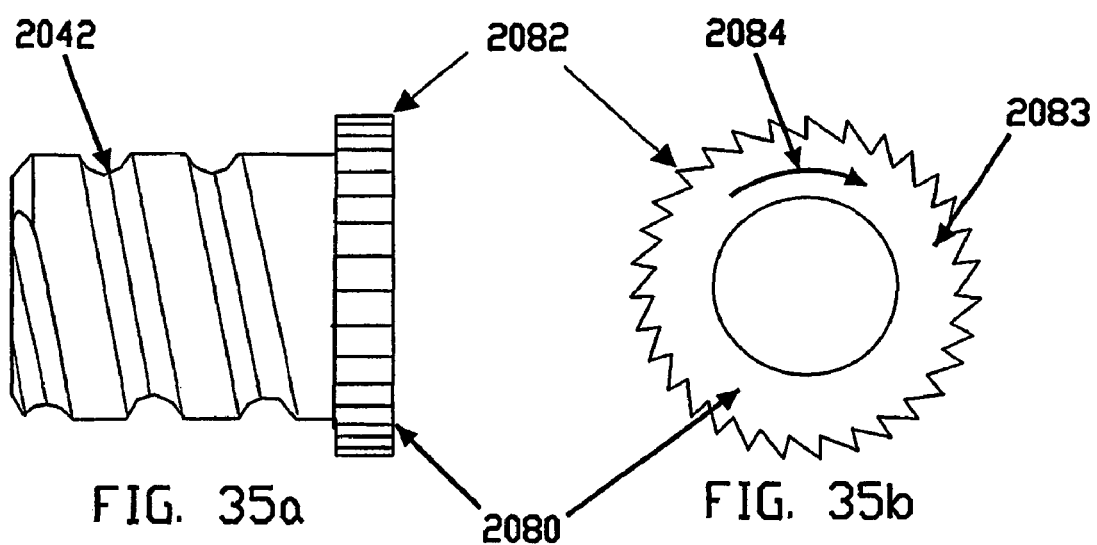
FIG. 35a illustrates a side view of a Tamperproof Threaded Clamp having barbed teeth added to the outer perimeter of the flange.
FIG. 35b illustrates a rear view of a Tamperproof Threaded Clamp having barbed teeth added to the outer perimeter of the flange.

Alternatively, a clamp of style 2080 in FIG. 35b, but having barbs oriented opposite to those on clamp 2080 would ensure the clamp is not over-tightened, as well as improve the likelihood that the clamp could always be removed (not illustrated).

Figure 36:
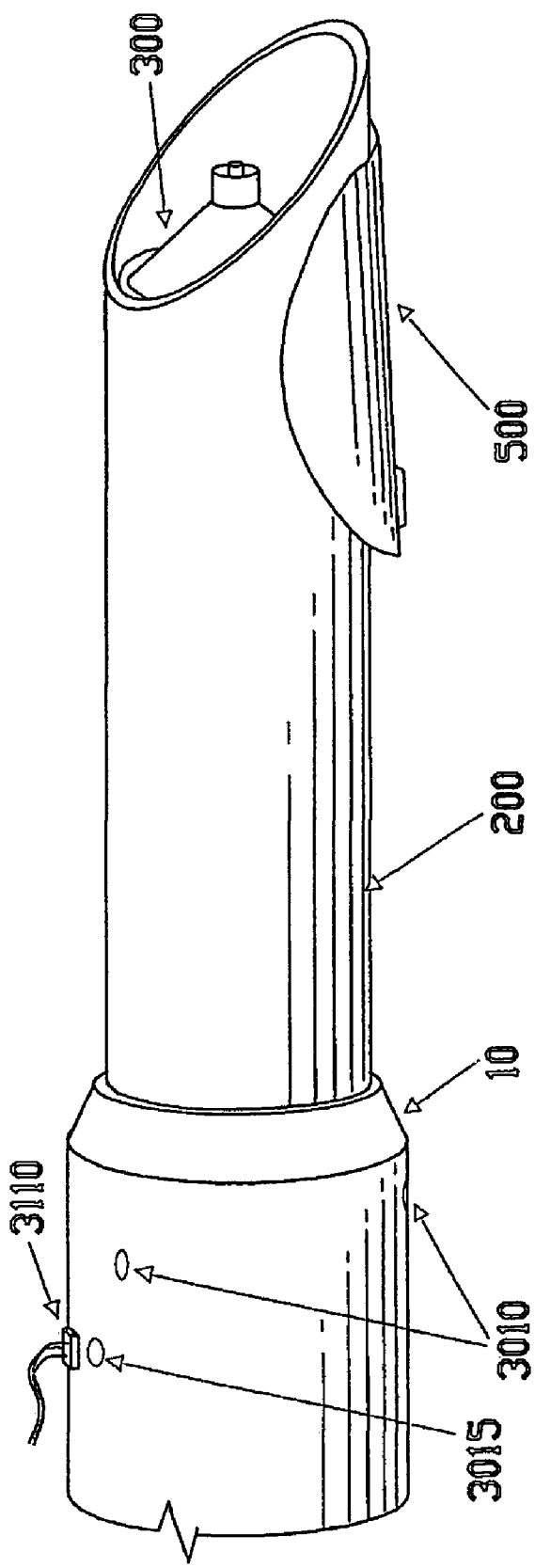
FIG. 36 illustrates a side perspective view of a syringe holder with an engagement portion to enable releasable engagement with a medical injector and sensing system to detect the presence of the syringe.

FIG. 36 illustrates a side perspective view of a syringe holder with an engagement portion to enable releasable engagement with a medical injector and sensing system to detect the presence of the syringe. Syringe holder 200 is engaged in injector nose 10 of the medical injector (not shown). Bayonet posts 3010 and a blocking member (holder lock post 3015) on injector nose 10 form part of the engagement mechanism between syringe holder 200 and the injector. Syringe 300 is loaded into holder 200 and retained by catch 500. The injector nose 10 has a sensor or switch 3110 for sensing the presence of a syringe in holder 200. According to the embodiment illustrated, it is an optical sensor.

Holder lock post 3015 is adjacent to syringe sensor 3110 and therefore syringe holder 200 cannot be removed whilst a syringe is installed, nor during an injection. Additionally, a syringe cannot be installed unless holder 200 is locked fully (in this case clockwise). This embodiment is particularly useful in the absence of a sensor to verify syringe presence. It will be appreciated that holder 200 could not be attached if a syringe were already installed.

To engage syringe holder 200 with injector nose 10, the holder is first inserted into the nose and with gentle inwards pressure, rotated until grooves 3020 (as shown in FIG. 37a) engage bayonet posts 3010. At this point holder 200 fully enters the nose 10, and the holder is rotated to lock it in place. Whilst 3 bayonet groove/post sets are illustrated spaced evenly around the circumference, they could also be oriented at matching odd angles so that the holder can only engage in a particular orientation. Seal 3145 could be a simple O-ring or wiper ring, and has 2 important roles:

(a) prevent fluids from entering the injector
(b) provide a friction means to decrease the possibility of inadvertent removal of the holder.

Figure 37D:
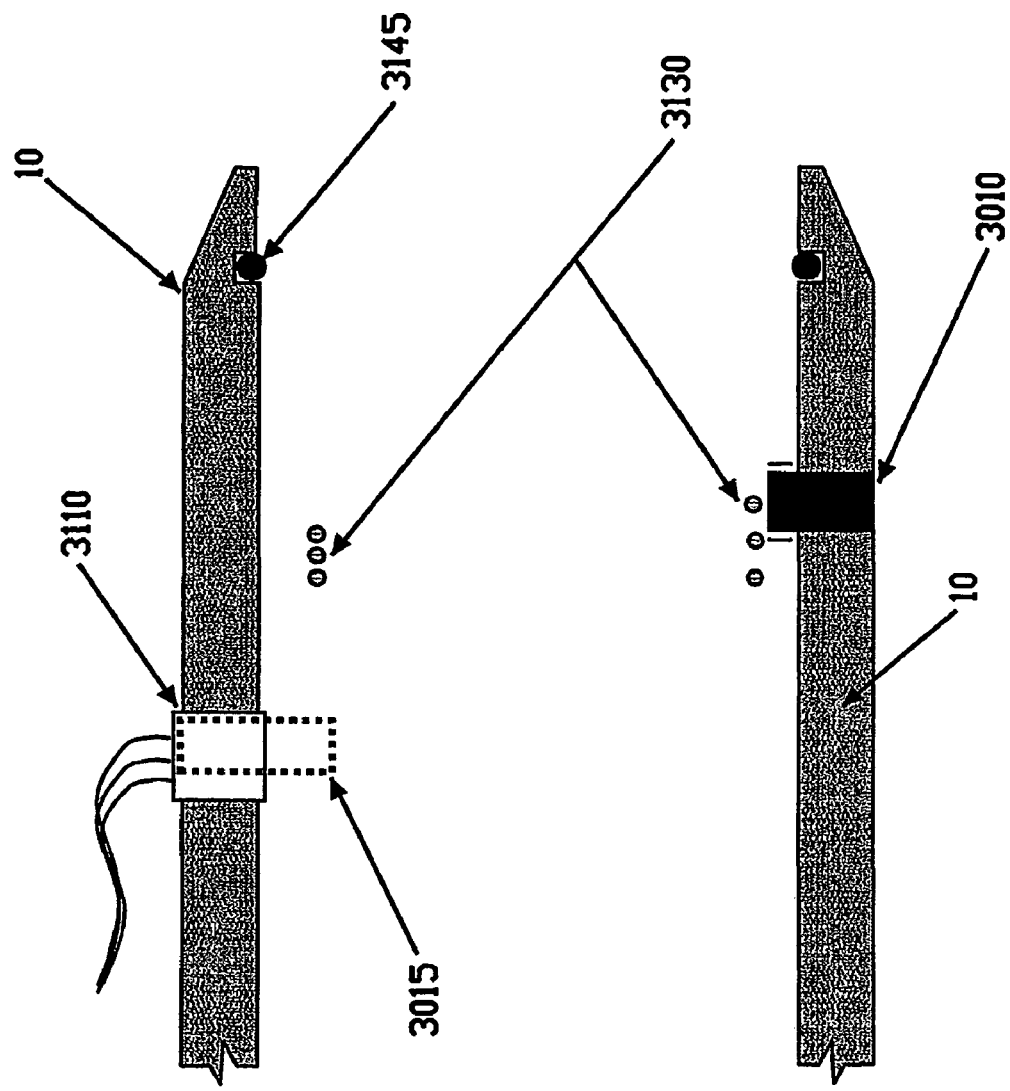
FIG. 37d illustrates a cross sectional view of the injector nose with holder lock post.

FIGS. 37a-d and 38a-e illustrate several views of a syringe holder with a bayonet attachment 3010, a blocking member (holder lock post 3015), loaded syringe and sensing system to detect the presence of a syringe. Injector nose 10 is fitted with a fluid seal 3145, a spring stop ring 3140 against which syringe flag spring 3130 abuts. A syringe stop and plunger bush 3135 sits within injector nose 10 and syringe 300 briefly engages bush 3135 to limit movement of the syringe 300 towards the medical injector. Bush 3135 has at least one groove 3150 in which tabs 3122 (as depicted in FIG. 37c), are slidingly engaged. Spring 3130 is compressed during assembly between stop ring 3140 and Tabs 3122 on Flag 3120, thereby biasing Flag 3120 forward (to the right). With no syringe installed Tabs 3122 rest against Bush 3135, and the pointed tip of Flag 3120 protrudes to the right of bush 3135.

Syringe holder 200 with grooves 3020 are introduced into injector nose 10 and the groove is engaged with pins 3010 and rotated to thereby lock it in place. When syringe barrel 300 is inserted into holder 200, it depresses syringe flag 3120 and thus pushes tabs 3122 of the flag against spring 3130. Biased catch 500 snaps shut and locks syringe 300 in place within the holder.

Holder lock post 3015 is of similar width to, and mounted on the same axis, as flag 3120. As holder 200 is attached, flag 200 almost touches it (the lock post?) when bayonet slots 3020 are fully engaged with posts 3010 (without rotating). In the mounted position, with a syringe installed and flag 3020 pushed back, holder 200 cannot be rotated the wrong way (in the present case anti-clockwise) because the flag 200 will engage the lock post 3015 and thereby prevent rotation of the holder 200 within the injector nose 10.

Flag 3120 has a beveled tip 3124 to engage syringe 300 and thereby grip it to minimize rotational movement. The movement of flag 3120 towards the injector triggers sensor 3110 which thereby creates a signal to the effect that a syringe is present in the holder. In the present case, sensor 3110 is a combination light emitter and detector sensing light reflected off the metallic surface of Flag 3120. The signal created may go to a controller which thereby integrates the information and controls the movement of the syringe plunger 130. For example, the controller may restrict movement of the plunger until after the sensor creates a signal that a syringe is present. When syringe 300 is removed from holder 200, spring 3130 pushes flag 3120 away from sensor 3110 and thereby eliminates the reflections.

During assembly of holder 200 onto injector nose 10, bush 3135 and spring stop 3140 are normally fixed in place inside the holder by means of cement, screws, or pins. Both stops have a small longitudinal groove 3150 in their outer surfaces to support slidable syringe flag 3120 which, together with flag spring 3130, are held in place by bush 3135 and stop 3140. Spring 3130 is lodged between spring stop 3140 and tabs 3122, thereby biasing the flag forward. With no syringe loaded, flag 3120 protrudes forward of the syringe stop 3135, and its tabs lodge against the rear of the syringe stop. A secondary function of the syringe stop is to bear and centre the plunger, and prevent stray fluid around the syringe from entering the injector.

In brief, the Syringe Flag device has 3 main functions:
1. Syringe ejector: Flag 3120 is slidably mounted in groove 3150, and is biased forward by flag spring 3130. As syringe 300 is loaded into holder 200 the rear rim strikes the flag, pushing it rearward and compressing the spring until the tip of the flag is flush with bush 3135. When catch 500 is opened, syringe 300 is partially ejected forward by the flag, making the syringe easier to grasp and remove.
2. When a tube is attached to the syringe (after it has been loaded), the operator needs to twist the connection to engage and lock the connection to the syringe thread. To restrain the syringe from rotating it would ordinarily need to be held with the other hand. However flag 3120 can perform this role. The forward tip 3124 of flag 3120 is beveled & sharp like a chisel, digging into the syringe a little, there by restraining rotation of the syringe.
3. The flag assists detection of the presence of a syringe in holder 200. Reflective infrared sensors such as Sharp GP2L24 are readily available types of sensors 3110. As the flag is pushed back by the syringe the reflective rear end of the flag is detected by the sensor, which in turn signals the controller. Those familiar with the art will appreciate that various other forms of detection or mechanical switching could be used to sense movement of the Flag 3120.

FIGS. 39a & b illustrate cross sectional views of a syringe in a syringe holder demonstrating a particularly preferred embodiment of the engagement mechanism between the hub and plunger.

Plunger 3600 is slidingly engaged with actuation member 3610 but with a limited free play between them due to space 3625. Note also that free sliding of plunger 3600 is somewhat subdued by the seal 3146. Whenever drive member 3500 and actuation member 3610 reverse direction, plunger 3600 does not move until space 3625 is traversed. Actuation member 3610 and its associated cone 3650 operate pins 3640 to automatically engage or disengage hub 310 at the appropriate time.

Holder 200 is engaged in injector nose 10. Syringe 300 has been fitted into holder 200. FIG. 39a demonstrates this embodiment in the situation where the plunger is expelling fluid from the syringe. Shoulder 3520 of plunger drive 3500 engages and pushes plunger 3600 and actuation member 3610 which is disposed within a bore in plunger 3600. Actuation member 3610 has a rod portion 3165 [not seen; labeled in FIG. 39] and a nose portion 3650 which is cone shaped. The forward movement of nose portion 3650 allows locking members in the form of pins 3640 which are biased by spring 3660 to retract from engagement with the engagement portion of hub 310. Thus hub 310 is automatically unlocked during and following forward movement of plunger 130. The purpose of unlocking the hub is to allow removal of the used syringe following an injection.

On retraction of plunger drive 3500, shoulder 3520 of plunger drive 3500 withdraws from the rear edge of plunger 3600 and thereby actuation member 3610 is drawn away from hub 310. Plunger 3600 is momentarily stationary, causing nose portion 3650 to slide along pins 3640 and thereby force them to extend from plunger 3600 and engage the engaging portion of the hub 310. Shoulder 3630 on actuation member 3610 traverses space 3625 and engages shoulder 3620 in the bore and enables nose portion 3650 to be positioned alongside pins 3640 by stopping actuation member 3610 from moving relatively further away from them. Thus hub 310 is automatically retained during and following retraction movement of plunger drive 3500, enabling retraction of the hub, and filing of the syringe.

Hence this system automatically ensures that the hub is either locked or unlocked at the appropriate time, avoiding inconvenience and enhancing safety of the injector—for the operator and the patient. Of course, the Controller must be programmed to allow for the inherent free play whenever the plunger reverses direction.

Figure 40:
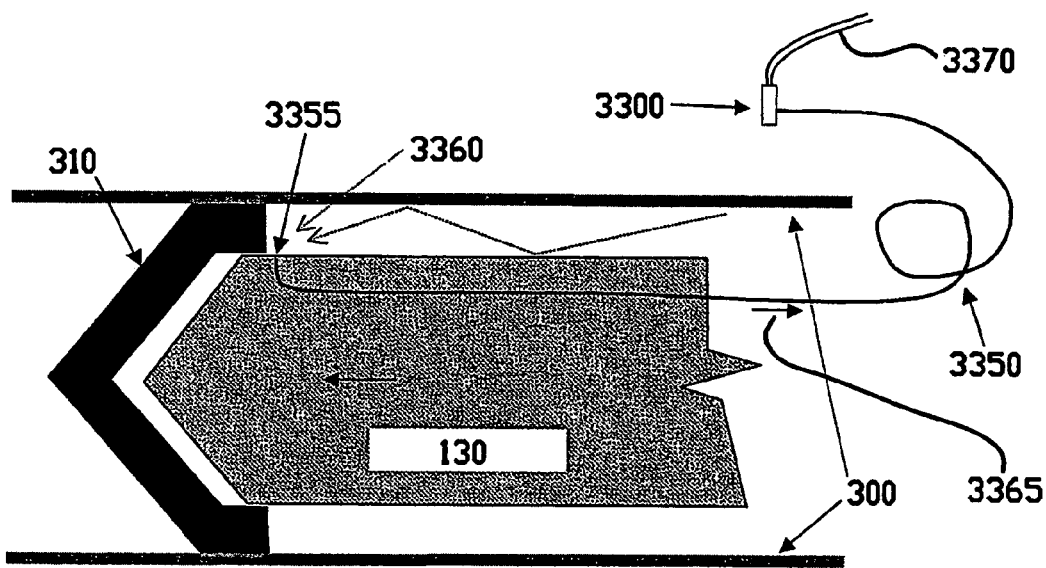
FIG. 40 illustrates a longitudinal cross sectional view of a plunger and hub demonstrating a preferred embodiment of the sensor to detect engagement between the hub and plunger.

FIG. 40 illustrates a longitudinal cross sectional view of a plunger and hub demonstrating a preferred embodiment of the sensor to detect engagement between the hub and plunger. Syringe 300 has a hub 310 slidingly disposed within it. Sensor 3300 is a light sensor with an optical fibre cable 3350 which is partially embedded in plunger 130. Optical fibre 3350 has an exposed end 3355 which is flush with the surface of plunger 130 and detects incident light 3360 which passes through transparent syringe 300. Incident light is then transmitted 3365 along optical cable 3350. When plunger 130 has fully engaged hub 310, which is opaque, incident light will not be able to hit the end of optical cable 3350. Therefore, the light sensor 3360 will detect the absence of light and create an appropriate signal. Of course, if the room lights are inadequate for the sensor to operate, the Plunger can be illuminated by the injector with visible or infrared light.

This signal may be sent to a controller via cable 3370 to enable further control over the movement of plunger 130. For example, it may allow plunger 130 to automatically stop upon full engagement with hub 310 without thereby causing hub 310 to be moved forward. According to this embodiment, since the aperture at the end of the optic fibre is small, then the ambient light is cut off abruptly as the plunger enters the hub, and so the accuracy and predictability of the system is enhanced. Similarly, because of the high contrast between the engaged and non-engaged states, the level of ambient or illuminated light is not critical.

Figure 41:
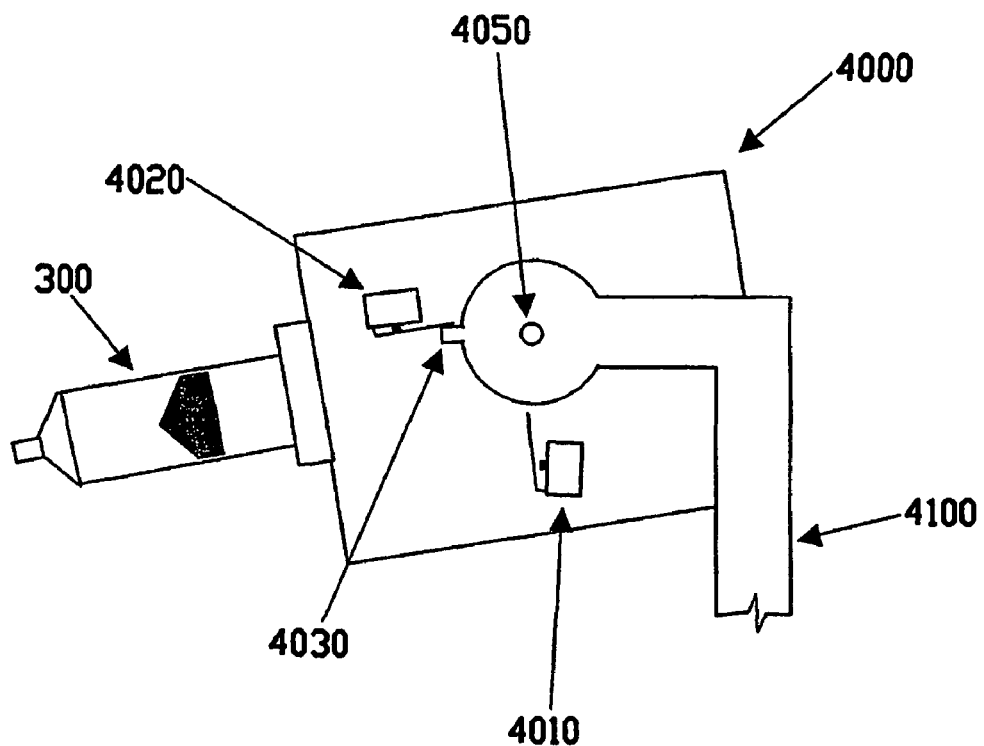
FIG. 41 illustrates an injector with tilt switches in the injecting (down) position.
Figure 42:
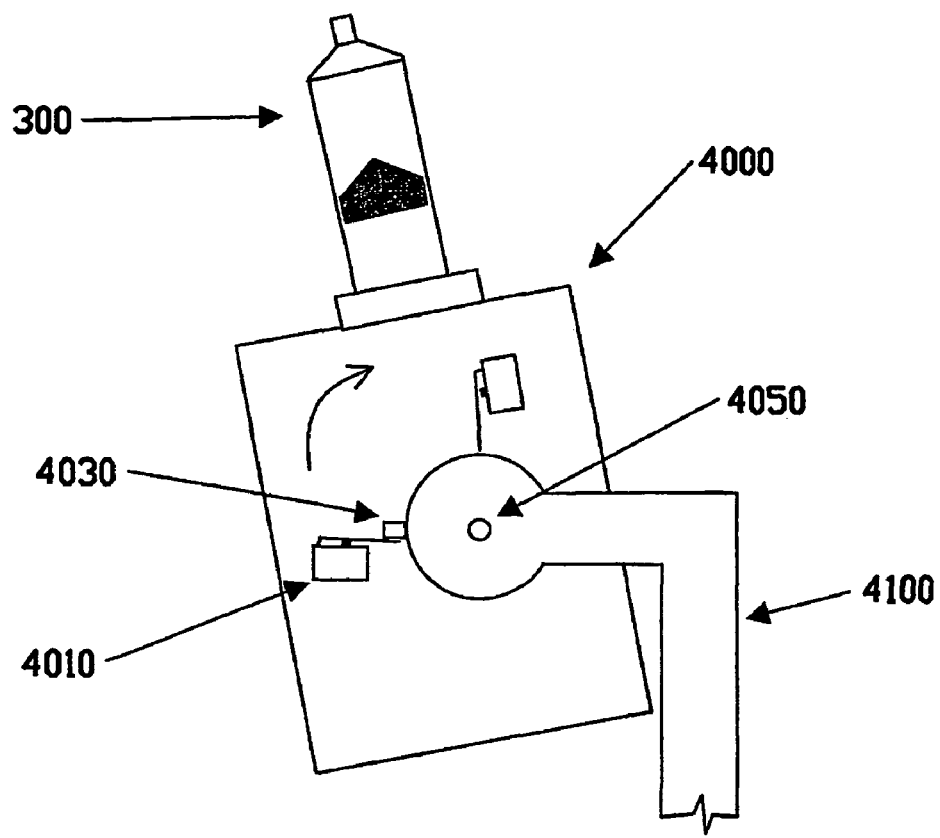
FIG. 42 illustrates an injector with tilt switches in the filing (up) position.

FIGS. 41 & 42 illustrate one embodiment of the medical injector with tilt switches in the injecting and filing positions. Injector Head 4000 contains the control and drive elements of the Injector and is mounted at Head Pivot 4050 to Injector Pedestal 4100, which preferably stands on a wheeled base (not shown). Head 4000 is able to tilt about the pivot by at least 90 degrees.

A small Switch Tab 4030 extends from Injector Pedestal 4030. Switches 4010 and 4020 are fixed to the head in such positions as to strike the Switch Tab at the opposing positions of DOWN (4020) and UP (4010), at which points the appropriate switch changes state, and communicates to the Control circuitry (not shown) the orientation of head 4000. These communications can be used to initiate or inhibit a plurality of functions, operations, displays, responses, and/or safeguards in the injector.

Those familiar with the art will appreciate that various alternate sensors could be used in place of Switches 4010 and 4020, such as magnetic, optical, or mechanical. It will also be noted that a plurality of Tabs and Switches may be used to sense multiple orientations of the head.

It should also be noted that the above concepts operate without regard to earth's gravitation.

It will be understood by those familiar with the art that the inventions described above could be applied to any standard male luer locking connector, as found on many medical and other devices. It will also be understood that various combinations of outer and inner surfaces, combined with any of the above mentioned rear ends or flanges are possible, depending on the application.

The word 'comprising' and forms of the word 'comprising' as used in this description do not limit the invention claimed to exclude any variants or additions.

Modifications and improvements to the invention will be readily apparent to those skilled in the art. Such modifications and improvements are intended to be within the scope of this invention.

The claims defining the invention are as follows:

1. A plunger for a syringe for use with a medical injector system, the syringe having a barrel and a hub slidingly engaging the barrel, the plunger comprising:
   an outer surface;
   an actuating member disposed at least partially within a longitudinal bore defined in the inside of the outer surface;
   a channel extending in a radial direction; and
   at least one retention member slideably disposed within the channel to retractably protrude from at least an inner surface to at least above the outer surface,
   wherein the at least one retention member terminates with an inwardly projection end formed as a curved contacting surface,
   wherein the retention member is adapted to releasably engage a substantially annular engaging portion on an inner surface of the hub upon retraction of the plunger to permit the hub to be selectively withdrawn along the barrel by the plunger.

2. A plunger according to claim 1 adapted for manual filling of the syringe.

3. A plunger according to claim 2 wherein the plunger is incapable of engaging the hub after the syringe has been used.

4. A plunger according to claim 3 wherein the plunger is sufficiently shorter than the barrel of the syringe such that it can not reach the hub when the hub is located at the front most portion of the syringe barrel.

5. The plunger of claim 1 wherein, for a syringe for use with a medical injector system, the syringe having a barrel and a hub slidingly engaging the barrel, the plunger further including a sensor to detect a level of engagement between the plunger and the hub.

6. A plunger according to claim 5 comprising a mechanical sensor.

7. A plunger according to claim 5 comprising an electromagnetic sensor.

8. A plunger according to claim 1 wherein the retention member is mechanically and/or electrically releasably engaged with the hub.

9. A plunger according to claim 8 wherein the releasable engagement is at least partly actuated by a weight mechanism.

10. A plunger according to claim 5 comprising a light sensor.

11. A plunger according to claim 10 wherein the light sensor comprises a fibre optic cable.

12. A plunger according to claim 1 wherein the retention member comprises a cam.

13. A plunger according to claim 1 wherein the retention member comprises a cone.

14. A plunger according to claim 1 wherein the actuation member is movable longitudinally along the bore in the plunger.

15. A plunger according to claim 1 wherein the retention member comprises a pin.

16. A plunger according to claim 5 wherein the sensor detects full engagement between the plunger and hub.

17. The plunger of claim 1 further including an outer portion shaped to have a form fit with the hub.

18. The plunger of claim 1 further including a tip portion engaging with an inner surface of the hub.

19. A plunger for a syringe for use with a medical injector system, the syringe having a barrel and a hub disposed externally to and slidingly engaging the barrel, the plunger comprising:
   an outer surface;
   a channel extending in a radial direction;
   an actuating member disposed at least partially within a longitudinal bore defined in the inside of the outer surface; and
   a retention member formed as a cam and connected to a distal end of the actuating member, wherein the retention member retractably protrudes in the radial direction from above the outer surface to below the outer surface,
   wherein the retention member is adapted to maintain an outwardly projecting position above the outer surface and releasably engage a substantially annular engaging portion on an inner surface of the hub upon retraction of the plunger to permit the hub to be selectively withdrawn along the barrel by the plunger, and
   wherein the actuating member is disposed in a bore offset from the center of the barrel.

* * * * *

UNITED STATES PATENT AND TRADEMARK OFFICE
CERTIFICATE OF CORRECTION

PATENT NO.         : 7,682,345 B2                                           Page 1 of 2
APPLICATION NO.    : 10/380188
DATED              : March 23, 2010
INVENTOR(S)        : Savage It is certified that error appears in the above-identified patent and that said Letters Patent is hereby corrected as shown below:

IN THE SPECIFICATION

In Column 8, Line 44, delete "filing" and insert -- filling --, therefor.

In Column 11, Line 32, delete "fling" and insert -- filling --, therefor.

In Column 12, Line 52, delete "sch" and insert -- such --, therefor.

In Column 13, Line 55, delete "present" and insert -- present. --, therefor.

In Column 14, Line 6, delete "all" and insert -- an --, therefor.

In Column 14, Line 16, delete "member" and insert -- member. --, therefor.

In Column 16, Line 13, delete "filing" and insert -- filling --, therefor.

In Column 19, Line 29, delete "catch," and insert -- catch; --, therefor.

In Column 20, Line 42, delete "haying" and insert -- having --, therefor.

In Column 21, Line 14, delete "and syringe of" and insert -- through the line MM; --, therefor.

In Column 21, Line 15, delete "Fig. 38a through the line MM;", therefor.

In Column 21, Line 37, delete "position;" and insert -- position. --, therefor.

In Column 21, Line 39, delete "OF PREFERRED" and insert -- OF THE PREFERRED --, therefor.

In Column 22, Line 12, delete "pre-filed" and insert -- pre-filled --, therefor.

Signed and Sealed this
Eleventh Day of September, 2012

David J. Kappos
*Director of the United States Patent and Trademark Office*

IN THE SPECIFICATION

In Column 22, Line 26, delete "Kraiburg etc." and insert -- Kraiburg, etc. --, therefor.

In Column 22, Lines 60-67, delete "However, empty new........such a mechanism." and insert the same at Line 59, after "pre-filled syringe." as a continuation of the paragraph, therefor.

In Column 25, Line 39, delete "fill" and insert -- full --, therefor.

In Column 26, Line 29, delete "is air" and insert -- if air --, therefor.

In Column 26, Line 65, delete "This reduces the risk of spilling contaminated blood." and insert the same at Line 64, after "after use." as a continuation of the paragraph, therefor.

In Column 27, Line 47, delete "springs" and insert -- spring --, therefor.

In Column 28, Line 20, delete "and," and insert -- and --, therefor.

In Column 29, Line 54, delete "air)" and insert -- air). --, therefor.

In Column 30, Line 43, delete "FIG. 27c.)," and insert -- FIG. 27c), --, therefor.

In Column 32, Lines 29-35, delete "The clamp 2020 is installed......the syringe." and insert the same at Line 27 after "assembly.", as a continuation of the paragraph, therefor.

In Column 33, Line 11, delete "2050," and insert -- 2050. --, therefor.

In Column 33, Lines 23-25, delete "Alternately......force." and insert the same at Line 22, after "above." as a continuation of the paragraph, therefor.

In Column 36, Line 8, delete "filing" and insert -- filling --, therefor.

IN THE CLAIMS

In Column 37, Line 27, in Claim 1, delete "the retention member" and insert -- the at least one retention member --, therefor.

In Column 38, Lines 11-12, in Claim 12, delete "the retention member comprises a cam" and insert -- the actuating member comprises a cam --, therefor.

In Column 38, Lines 15-16, Claim 14, delete "the actuation member" and insert -- the actuating member --, therefor.

In Column 38, Lines 18-19, in Claim 15, delete "wherein the retention member" and insert -- wherein the at least one retention member --, therefor.